US012790616B2

(12) United States Patent
Zandanel et al.

(10) Patent No.: US 12,790,616 B2
(45) Date of Patent: Nov. 10, 2026

(54) CONJUGATED NUCLEIC ACID MOLECULES AND THEIR USES

(71) Applicant: VALERIO THERAPEUTICS, Paris (FR)

(72) Inventors: Christelle Zandanel, Fontenay-Aux-Roses (FR); Marc Lemaitre, Cincinnati, OH (US); Loïc Roux, Hailey (GB)

(73) Assignee: VALERIO THERAPEUTICS, Paris (FR)

( * ) Notice: Subject to any disclaimer, the term of this patent is extended or adjusted under 35 U.S.C. 154(b) by 672 days.

(21) Appl. No.: 18/251,720

(22) PCT Filed: Dec. 15, 2022

(86) PCT No.: PCT/EP2022/086199

§ 371 (c)(1), (2) Date: May 4, 2023

(87) PCT Pub. No.: WO2023/111203

PCT Pub. Date: Jun. 22, 2023

(65) Prior Publication Data

US 2024/0294926 A1 Sep. 5, 2024

(30) Foreign Application Priority Data

Dec. 16, 2021 (EP) .................................... 21306798

(51) Int. Cl.

| | |
|---|---|
| ***C07H 21/02*** | (2006.01) |
| ***A61K 45/06*** | (2006.01) |
| ***A61K 47/54*** | (2017.01) |
| ***A61P 35/00*** | (2006.01) |
| ***C07H 21/04*** | (2006.01) |
| ***C12N 15/117*** | (2010.01) |

(52) U.S. Cl.

CPC ............ *C12N 15/117* (2013.01); *A61K 45/06* (2013.01); *A61K 47/554* (2017.08); *A61P 35/00* (2018.01); *C12N 2310/17* (2013.01); *C12N 2310/315* (2013.01); *C12N 2310/3515* (2013.01); *C12N 2310/531* (2013.01); *C12N 2320/31* (2013.01); *C12N 2320/32* (2013.01)

(58) Field of Classification Search

CPC ............................ C12N 15/117; C12N 15/113

See application file for complete search history.

(56) References Cited

U.S. PATENT DOCUMENTS

| | | | |
|---|---|---|---|
| 10,563,197 | B2 | 2/2020 | Dutreix et al. |
| 11,162,095 | B2 | 11/2021 | Dutreix et al. |
| 2022/0054524 | A1 | 2/2022 | Sproat et al. |

FOREIGN PATENT DOCUMENTS

| | | | | |
|---|---|---|---|---|
| WO | WO-0220773 | A2 * | 3/2002 | .............. A61P 43/00 |
| WO | WO-2007048244 | A2 * | 5/2007 | .............. A61P 31/14 |
| WO | WO 2014/170441 | | 10/2014 | |
| WO | WO 2017/013237 | | 1/2017 | |
| WO | WO 2020/127965 | | 6/2020 | |
| WO | WO-2020127965 | A1 * | 6/2020 | ........... C12N 15/113 |

OTHER PUBLICATIONS

Chen (Chinese Anti-Cancer Association, 2011, 30, 7, 463-471).*
Chalmers et al. (British Medical Bulletin 2009; 89: 23-40).*
European Search Report for European Application No. 21306798.6, May 17, 2022, pp. 1-7.
Jdey, W. et al. "Abstract 527: A new generation of PARP interfering drug candidates for cancer treatment" *Cancer Res*, Jul. 1, 2021, pp. 1-4, vol. 81, No. 13 supplement.
Jdey, W. et al. "OX401, a new generation of PARP-interfering drug for cancer treatment" Abstract No. 21P, *Annals of Oncology*, 2020, p. S8, vol. 31, Issue S1.
Jdey, W. et al. "OX401, a new generation of PARP-interfering drug for cancer treatment" Mar. 2, 2020, Poster 21P, p. 1, retrieved from the Internet: URL:https://www.onxeo.com/wp-content/uploads/2020/02/poster-tat-2020-ox401-final.pdf [retrieved on Nov. 16, 2020].

* cited by examiner

*Primary Examiner* — Amy Rose Hudson
(74) *Attorney, Agent, or Firm* — SALIWANCHIK, LLOYD & EISENSCHENK

(57) ABSTRACT

The present invention relates to new nucleic acid molecules of therapeutic interest, in particular for use in the treatment of cancer.

16 Claims, 22 Drawing Sheets

Specification includes a Sequence Listing.

| | OX401 | OX413 |
| --- | --- | --- |
| IC50 | 6.140 | 0.2019 |

| | UWB1.289 | UWB1.289 BRCA1 |
|---|---|---|
| IC50 | 0.7015 | 11.42 |

| | UWB1.289 | UWB1.289 BRCA1 |
|---|---|---|
| IC50 | 0.02653 | 0.03637 |

CONJUGATED NUCLEIC ACID MOLECULES AND THEIR USES

CROSS-REFERENCE TO RELATED APPLICATION

This application is the U.S. national stage application of International Patent Application No. PCT/EP2022/086199, filed Dec. 15, 2022.

REFERENCE TO SEQUENCE LISTING

The Sequence Listing for this application is labeled "Seq-List-replace.xml" which was created on Jan. 29, 2024 and is 75,435 bytes. The entire content of the sequence listing is incorporated herein by reference in its entirety.

FIELD OF THE INVENTION

The present invention relates to the field of medicine, in particular of oncology.

BACKGROUND OF THE INVENTION

DNA-damage response (DDR) detects DNA lesions and promotes their repair. The wide diversity of DNA-lesion types necessitates multiple, largely distinct DNA-repair mechanisms such as mismatch repair (MMR), base-excision repair (BER), nucleotide excision repair (NER), single-strand break repair (SSB) and double-strand break repair (DSB). For example, the polyadenyl-ribose polymerase (PARP) is involved essentially in repairing SSBs while two principal mechanisms are used for repairing DSBs in DNA: non-homologous end-joining (NHEJ) and homologous recombination (HR). PARP-1 acts as a first responder that detects DNA damage and then facilitates choice of repair pathway. In NHEJ, DSBs are recognized by the Ku proteins that then binds and activates the protein kinase DNA-PKcs, leading to recruitment and activation of end-processing enzymes. It has been demonstrated that the ability of cancer cells to repair therapeutically induced DNA damage impacts therapeutic efficacy.

This has led to targeting DNA repair pathways and proteins to develop anti-cancer agents that will increase sensitivity to traditional genotoxic treatments (chemotherapeutics, radiotherapy). Synthetic lethal approaches to cancer therapy have provided novel mechanisms to specifically target cancer cells while sparing non-cancer cells and thereby reducing toxicity associated with treatment.

Amongst these synthetic lethal approaches, Dbait molecules are nucleic acid molecules that mimic double-stranded DNA lesions. They act as a bait for DNA damage signaling enzymes, PARP and DNA-PK, inducing a "false" DNA damage signal and ultimately inhibiting recruitment at the damage site of many proteins involved in DSB and SSB pathways.

Dbait molecules have been extensively described in PCT patent applications WO2005/040378, WO2008/034866 WO2008/084087, WO2011/161075, WO2017/013237, WO2017/148976, and WO2019/175132. Dbait molecules may be defined by a number of characteristics necessary for their therapeutic activity, such as their minimal length which may be variable, as long as it is sufficient to allow appropriate binding of Ku protein complex comprising Ku and DNA-PKcs proteins. It has thus been showed that the length of Dbait molecules must be greater than 20 bp, preferably about 32 bp, to ensure binding to such a Ku complex and enabling DNA-PKcs activation.

Potential predictive biomarkers for treatment with such Dbait molecules were characterized. Sensitivity to Dbait molecules was indeed associated with a high spontaneous frequency of cells with micronuclei (MN) as described in PCT patent application WO2018/162439. A high basal level of MN was proposed as a predictive biomarker for treatment with Dbait molecules consecutive to a validation in 43 solid tumor cell lines from various tissues and 16 models of cell- and patient-derived xenografts.

Moreover, it has been recently proposed that micronuclei (MN) would provide a key platform as part of DNA damage-induced immune response (Gekara J Cell Biol. 2017 Oct. 2; 216(10):2999-3001). Recent studies demonstrate a role for MN formation in DNA damage-induced immune activation. Interestingly, a cytosolic DNA sensing pathway has indeed emerged as the major link between DNA damage and innate immunity. DNA normally resides in the nucleus and mitochondria; hence, its presence in the cytoplasm serves as a danger-associated molecular pattern (DAMP) to trigger immune responses. Cyclic guanosine monophosphate (GMP)-adenosine monophosphate (AMP) synthase (cGAS) is the sensor that detects DNA as a DAMP and induces type I IFNs and other cytokines. DNA binds to cGAS in a sequence-independent manner; this binding induces a conformational change of the catalytic center of cGAS such that this enzyme can convert guanosine triphosphate (GTP) and ATP into the second messenger cyclic GMP-AMP (cGAMP). This cGAMP molecule is an endogenous high-affinity ligand for the adaptor protein Stimulator of IFN Gene STING. Activation of the STING pathway may then include, for example, stimulation of inflammatory cytokines, IP-10 (also known as CXCL10), and CCL5 or receptors NGK2 and PD-L1.

Recent evidence indicates involvement of the STING (stimulator of interferon genes) pathway in the induction of antitumor immune response. Therefore, STING agonists are now being extensively developed as a new class of cancer therapeutics. It has been shown that activation of the STING-dependent pathway in cancer cells can result in tumor infiltration with immune cells and modulation of the anticancer immune response.

STING is an endoplasmic reticulum adaptor that facilitates innate immune signaling (a rapid nonspecific immune response that fights against environmental insults including, but not limited to, pathogens such as bacteria or viruses). It was reported that STING is able to activate NF-kB, STAT6, and IRF3 transcription pathways to induce expression of type I interferon (e.g., IFN-α and IFN-β) and exerts a potent anti-viral state following expression. However, STING agonists developed so far are able to activate the STING pathway in all cell types and could trigger dramatic side effects linked to their activation in dendritic cells. In consequence, STING agonists are locally administrated.

Cancer cells have a unique energy metabolism for sustaining rapid proliferation. The preference for anaerobic glycolysis under normal oxygen conditions is a unique trait of cancer metabolism and is designated as the Warburg effect. Enhanced glycolysis also supports the generation of nucleotides, amino acids, lipids, and folic acid as the building blocks for cancer cell division. Nicotinamide adenine dinucleotide (NAD) is a co-enzyme that mediates redox reactions in a number of metabolic pathways, including glycolysis. Increased NAD levels enhance glycolysis and fuel cancer cells. In this context NAD levels depletion subsequently suppress cancer cell proliferation through inhibition of energy production pathways, such as glycolysis, tricarboxylic acid (TCA) cycle, and oxidative phosphorylation. NAD also serves as a substrate for several enzymes thus regulating DNA repair, gene expression, and stress response through these enzymes. Thus, NAD metabolism is implicated in cancer pathogenesis beyond energy metabolism and considered a promising therapeutic target for cancer treatment in particular on cancer cells that displays NAD deficiency due to DNA repair genes deficiency (for example ERCC1 and ATM deficiency) or IDHs (Isocitrate dehydrogenase) mutations.

New generation products OX400 designed using the proprietary PlatON™ platform of oligonucleotides developed to trap PARP proteins have been generated. OX400 compounds have been shown to specifically activate the STING pathway in tumor cells. OX400 compounds, in particular OX401 compound, have been extensively described in PCT patent application WO 2020/127965.

There remains a need for therapies for cancer treatment, especially drugs which rely on several mechanisms, especially DNA repair pathways and STING pathway activators, and for drugs that may help checkpoint inhibitors to work in more patients and across a wider range of cancers.

There also remains a need for new treatment methods to successfully address cancer cell populations without the emergence of cancer cells resistant to therapies.

SUMMARY OF THE INVENTION

The present invention provides new conjugated nucleic acid molecules which target DNA repair pathways and stimulate the STING pathway specifically in cancer cells. More specifically, the nucleic acid molecule is able to activate PARP without any activation of DNA-PK.

The present invention relates to a conjugated nucleic acid molecule comprising a 16 to 17-base pairs (bp) double-stranded nucleic acid moiety, the 5' end of the first strand and the 3' end of the complementary strand being linked together by a loop, and optionally a molecule facilitating the endocytosis which is linked to the loop, wherein:

the 16 to 17-base pairs (bp) double-stranded nucleic acid has the following sequence SEQ ID NOs: 1 and 2

5'idNCCCAGCAAsAsCsAsAsGCCN
3'idNGsGGNCGsTsTsTsGNNCGGA Loop, respectively, wherein each occurrence of N is independently T or U;

wherein idN is an inverted nucleotides and is present or absent;

wherein internucleotide linkages "s" refer to phosphorothioate internucleotide linkages; and wherein the underlined nucleotides are 2'-modified nucleotides, the loop has a structure selected from one of the following formulae:

$$—O—P(X)OH—O—\{[(CH_2)_2—O]_g—P(X)OH—O\}_r—K—O—P(X)OH—O—\{[(CH_2)_2—O]_h—P(X)OH—O—\}_s \quad (I)$$

with r and s being independently an integer 0 or 1; g and h being independently an integer from 1 to 7 and the sum g+h being from 4 to 7;

with K being

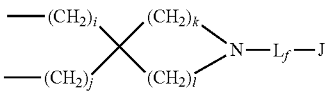

with i, j, k and l being independently an integer from 0 to 6, preferably from 1 to 3, L being a linker, f being an integer being 0 or 1, and J being a molecule facilitating the endocytosis or being H;

or $$—O—P(X)OH—O—[(CH_2)_d—C(O)—NH]_b—CHR—[C(O)—NH—(CH_2)_e]_c—O—P(X)OH—O— \quad (II)$$

with b and c being independently an integer from 0 to 4, and the sum b+c is from 3 to 7; d and e being independently an integer from 1 to 3, preferably from 1 to 2; and with R being -$L_f$-J, X being O or S at each occurrence of —O—P(X)OH—O—, L being a linker and f being an integer being 0 or 1, and J being a molecule facilitating the endocytosis or being H; and wherein the molecule has 1) at least one N which is U, and/or 2) at least one idN which is present; and/or 3) the loop being $$—O—P(X)OH—O—\{[(CH_2)_2—O]_g—P(X)OH—O\}_r—K—O—P(X)OH—O—\{[(CH_2)_2—O]_h—P(X)OH—O—\}_s \quad (I)$$

and K being $—CH_2—CH(L_f$-J)-

In a particular aspect, J is a molecule facilitating the endocytosis and the molecule facilitating the endocytosis can be selected from the group consisting of a cholesterol, single or double chain fatty acids, ligand which targets a cell receptor enabling receptor mediated endocytosis, or a transferrin. More specifically, the molecule facilitating the endocytosis is a cholesterol.

Optionally, the loop has the formula (I) and r is 1, s is 0 and g is an integer from 5 to 7, preferably 6.

The loop can have the formula (I) and when i and j are 1 and k and l are both 1 or 2, K is

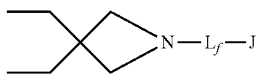

or

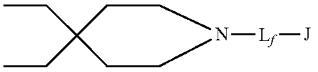

Optionally, f is 1 and L-J is $—C(O)—(CH_2)_m—NH—[(CH_2)_2—O]_n—(CH_2)_p—C(O)$-J, or $—C(O)—(CH_2)_m—NH—[C(O)—CH_2—O]t-[(CH_2)_2—O]_n—(CH_2)_p—[C(O)]_v$-J or $—CH_2—O—[(CH_2)_2—O]_n—(CH_2)_m—NH—(CH_2)_p—C(O)$-J with m being an integer from 0 to 10; n being an integer from 0 to 6; and p being an integer from 0 to 2; t and v being an integer 0 or 1 with at least one among t and v being 1.

Optionally, f is 1 and L-J is selected in the group consisting of $—C(O)—(CH_2)_m—NH—[(CH_2)_2—O]_n—(CH_2)_p—C(O)$-J, $—C(O)—(CH_2)_m—NH—C(O)—[(CH_2)_2—O]_n—(CH_2)_p$-J, $—C(O)—(CH_2)_m—NH—C(O)—CH_2—O—[(CH_2)_2—O]_n—(CH_2)_p$-J, $—C(O)—(CH_2)_m—NH—C(O)—[(CH_2)_2—O]_n—(CH_2)_p—C(O)$-J $—C(O)—(CH_2)_m—NH—C(O)—CH_2—O—[(CH_2)_2—O]_n—(CH_2)_p—C(O)$-J, and $—CH_2—O—[(CH_2)_2$ $—O]_n—(CH_2)_m—NH—(CH_2)_p—C(O)$-J with m being an integer from 0 to 10; n being an integer from 0 to 15; and p being an integer from 0 to 3.

Optionally, m is an integer between 4 and 6, preferably 5.

Optionally, the loop has the formula (I)

$$—O—P(X)OH—O—\{[(CH_2)_2—O]_g—P(X)OH—O\}_r—K—O—P(X)OH—O—\{[(CH_2)_2—O]_h—P(X)OH—O—\}_s \quad (I)$$

with X being S, r being 1, g being 6, s being 0, and when i and j are 1 and k and l are 2, K is

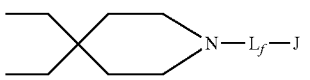

with f being 1 and L-J being $C(O)—(CH_2)_5—NH—[(CH_2)_2—O]_3—(CH_2)_2—C(O)$-J, $—C(O)—(CH_2)_5—NH—C(O)—[(CH_2)_2—O]_3—(CH_2)_3$-J, $—C(O)—(CH_2)_5—NH—C(O)—CH_2—O—[(CH_2)_2—O]_5—CH_2—C(O)$-J, $—C(O)—(CH_2)_5—NH—C(O)—CH_2—O—[(CH_2)_2—O]_9—CH_2—C(O)$-J, $—C(O)—(CH_2)_5—NH—C(O)—CH_2—O—[(CH_2)_2—O]_{13}—CH_2—C(O)$-J, $—C(O)—(CH_2)_5—NH—C(O)$-J or $—CH_2—O—[(CH_2)_2—O]_n—(CH_2)_m—NH—(CH_2)_p—C(O)$-J.

Optionally, f is 1 and L-J is $—C(O)—(CH_2)_m—NH—[(CH_2)_2—O]_n—(CH_2)_p—C(O)$-J, $—C(O)—(CH_2)_m—NH—[C(O)—CH_2—O]_t—[(CH_2)_2—O]_n—(CH_2)_p—[C(O)]_v$-J or $—CH_2—O—[(CH_2)_2—O]_n—(CH_2)_m—NH—(CH_2)_p—C(O)$-J with m being an integer from 0 to 10; n being an integer from 0 to 6; and p being an integer from 0 to 2; t and v being an integer 0 or 1 with at least one among t and v being 1. In an aspect, m is an integer between 4 and 6, preferably 5.

Optionally, f is 1 and L-J is selected in the group consisting of $—C(O)—(CH_2)_m—NH—[(CH_2)_2—O]_n—(CH_2)_p—C(O)$-J, $—C(O)—(CH_2)_m—NH—C(O)—[(CH_2)_2—O]_n—(CH_2)_p$-J, $—C(O)—(CH_2)_m—NH—C(O)—CH_2—O—[(CH_2)_2—O]_n—(CH_2)_p$-J, $—C(O)—(CH_2)_m—NH—C(O)—[(CH_2)_2—O]_n—(CH_2)_p—C(O)$-J $—C(O)—(CH_2)_m—NH—C(O)—CH_2—O—[(CH_2)_2—O]_n—(CH_2)_p—C(O)$-J, and $—CH_2—O—[(CH_2)_2—O]_n—(CH_2)_m—NH—(CH_2)_p—C(O)$-J with m being an integer from 0 to 10; n being an integer from 0 to 15; and p being an integer from 0 to 3. In an aspect, m is an integer between 4 and 6, preferably 5.

In a very specific aspect, L-J can be selected in the group consisting of $—C(O)—(CH_2)_5—NH—[(CH_2)_2—O]_3—(CH_2)_2—C(O)$-J, $—C(O)—(CH_2)_5—NH—C(O)—[(CH_2)_2—O]_3—(CH_2)_3$-J, $—C(O)—(CH_2)_5—NH—C(O)—CH_2—O—[(CH_2)_2—O]_5—CH_2—C(O)$-J, $—C(O)—(CH_2)_5—NH—C(O)—CH_2—O—[(CH_2)_2—O]_9—CH_2—C(O)$-J, $—C(O)—(CH_2)_5—NH—C(O)—CH_2—O—[(CH_2)_2—O]_{13}—CH_2—C(O)$-J, $—C(O)—(CH_2)_5—NH—C(O)$-J, or $—CH_2—O—[(CH_2)_2—O]_3—(CH_2)_3—NH—C(O)$-J.

In another particular aspect, the loop has the formula (I)

$$—O—P(X)OH—O—\{[(CH_2)_2—O]_g—P(X)OH—O\}_r—K—O—P(X)OH—O—\{[(CH_2)_2—O]_h—P(X)OH—O—\}_s \quad (I)$$

with X being S, r being 1, g being 6, s being 0, i and j being 1 and k and l being 2, with f being 1 and L-J being $C(O)—(CH_2)_5—NH—[(CH_2)_2—O]_3—(CH_2)_2—C(O)$-J, $—C(O)—(CH_2)_5—NH—C(O)—[(CH_2)_2—O]_3—(CH_2)_3$-J, $—C(O)—(CH_2)_5—NH—C(O)—CH_2—O—[(CH_2)_2—O]_5—CH_2—C(O)$-J, $—C(O)—(CH_2)_5—NH—C(O)—CH_2—O—[(CH_2)_2—O]_9—CH_2—C(O)$-J, $—C(O)—(CH_2)_5—NH—C(O)—CH_2—O—[(CH_2)_2—O]_{13}—CH_2—C(O)$-J, $—C(O)—(CH_2)_5—NH—C(O)$-J or $—CH_2—O—[(CH_2)_2—O]_3—(CH_2)_3—NH—C(O)$-J.

Optionally, the loop has the formula (I)

$$—O—P(X)OH—O—\{[(CH_2)_2—O]_g—P(X)OH—O\}_r—K—O—P(S)OH—O—\{[(CH_2)_2—O]_h—P(X)OH—O—\}_s,$$

X being O or S at each occurrence of —O—P(X)OH—O—, r being 1, g being 6, s being 0, and K being $CH_2—CH-(L_f$-J).

In a preferred object, the loop is $—O—P(S)OH—O—[(CH_2)_2—O]_6—P(O)OH—O—K—(O—P(S)OH—O)—$, K being $—CH_2—CH-(L_f$-J).

In another preferred object, the loop is $—O—P(S)OH—O—[(CH_2)_2—O]_6—P(S)OH—O—K—(O—P(S)OH—O)—$, K being $—CH_2—CH-(L_f$-J).

In another particular aspect, the loop has the formula (I)

$$—O—P(X)OH—O—\{[(CH_2)_2—O]_g—P(X)OH—O\}_r—K—O—P(X)OH—O—\{[(CH_2)_2—O]_h—P(X)OH—O—\}_s \quad (I)$$

and K is $—CH_2—CH(L_f$-J)-, f is 1 and L-J is $—CH_2—O—[(CH_2)_2—O]_n—(CH_2)_m—NH—(CH_2)_p—C(O)$-J, with m being 3; n being 3; and p being 0.

Optionally, the 2' modified nucleotides are independently selected from the group consisting of 2'-deoxy-2'-fluoro, 2'-O-methyl (2'-OMe), 2'-O-methoxyethyl (2'-O-MOE), 2'-O-aminopropyl (2'-O-AP), 2'-O-dimethylaminoethyl (2'-O-DMAE), 2'-O-dimethylaminopropyl (2'-O-DMAP), 2'-O-dimethylaminoethyloxyethyl (2'-O-DMAEOE), 2'-O—N-methylacetamido (2'-O-NMA) modification, 2'-deoxy-2'-fluoroarabinonucleotide (FANA), and 2' bridged nucleotides (LNA).

In a particular aspect, the 2' modified nucleotide is a 2'-deoxy-2'-fluoroarabinonucleotide (FANA). In another aspect, the 2'-modified nucleotides are 2'-O-methyl nucleotides (2'-OMe).

In a particular aspect, the conjugated nucleic acid molecule is:

SEQ ID NOs: 1 and 2

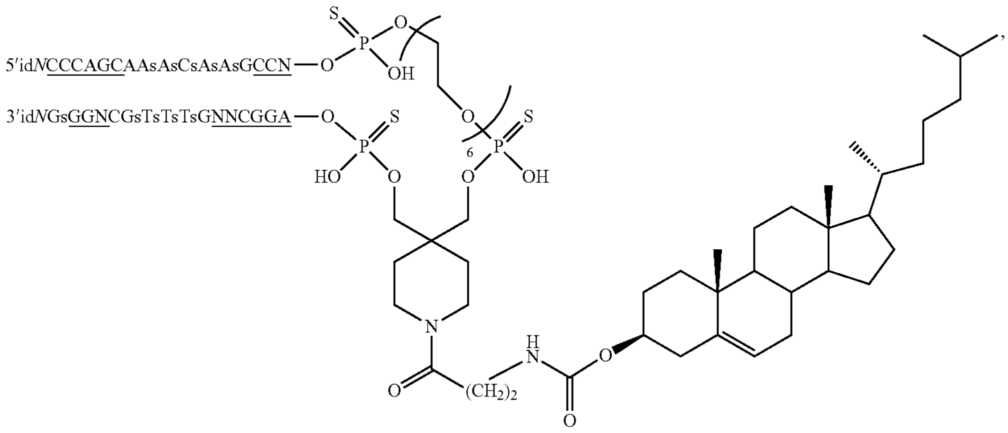

, respectively, wherein each occurrence of N is independently T or U, wherein idN is an inverted nucleotide and is present or absent, wherein internucleotide linkages “s” refer to phosphorothioate internucleotide linkages;

wherein the underlined nucleotides are 2'-modified nucleotides, preferably 2'-deoxy-2'-fluoroarabinonucleotides (F-ANA) or 2'O-Methyl nucleotides (2'-OMe); and wherein the molecule has 1) at least one N which is U, and/or 2) at least one idN which is present;

or the pharmaceutically acceptable salts thereof.

Optionally, when idN is present, idN is preferably an inverted thymidine, idT.

In a very particular aspect, the conjugated nucleic acid molecule is:

SEQ ID NOs: 3 and 4

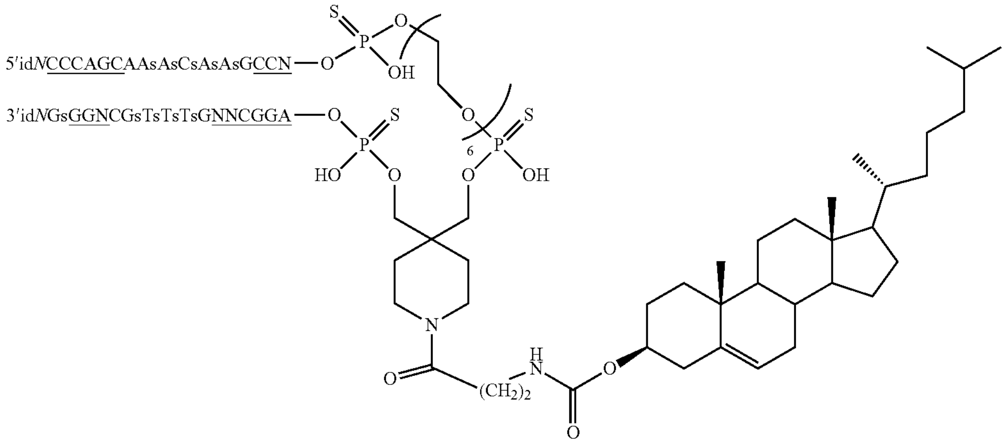

, respectively, wherein idN is an inverted nucleotide, preferably an inverted thymidine, idT, wherein N is T, wherein internucleotide linkages “s” refer to phosphorothioate internucleotide linkages; and wherein the underlined nucleotides are 2'-modified nucleotides, preferably 2'-deoxy-2'-fluoroarabinonucleotides (F-ANA) or 2'O-Methyl nucleotides (2'-OMe), or the pharmaceutically acceptable salts thereof.

In a very particular aspect, the conjugated nucleic acid molecule is:

SEQ ID NOs: 5 and 6

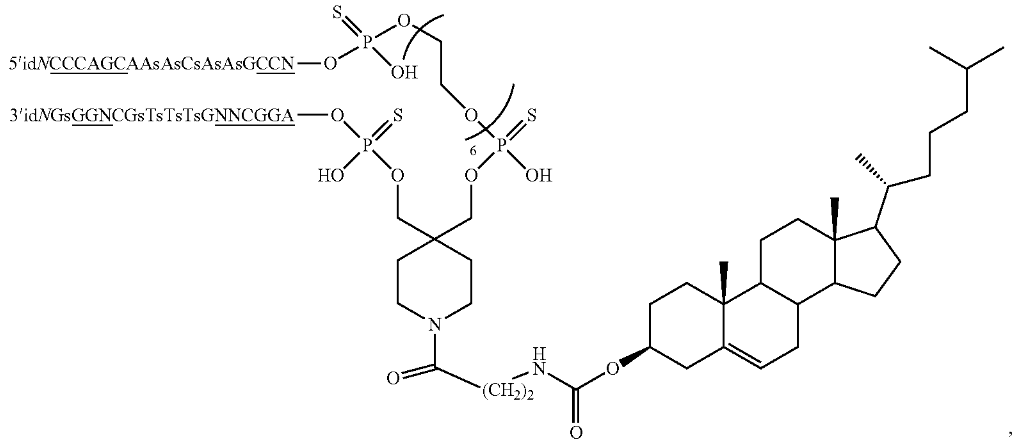

, respectively, wherein idN is an inverted nucleotide and is present or absent, and when idN is present, it is preferably an inverted thymidine, idT, wherein N is U, wherein internucleotide linkages “s” refer to phosphorothioate internucleotide linkages; and wherein the underlined nucleotides are 2'-modified nucleotides, preferably 2'-deoxy-2'-fluoroarabinonucleotides (F-ANA) or 2'O-Methyl nucleotides (2'-OMe), or the pharmaceutically acceptable salts thereof In one aspect, when the idN is absent, N is U and the underlined 2'-modified nucleotides are 2'-O-methyl nucleotides (2'-OMe), the molecule is OX416:

SEQ ID NOs: 7 and 8

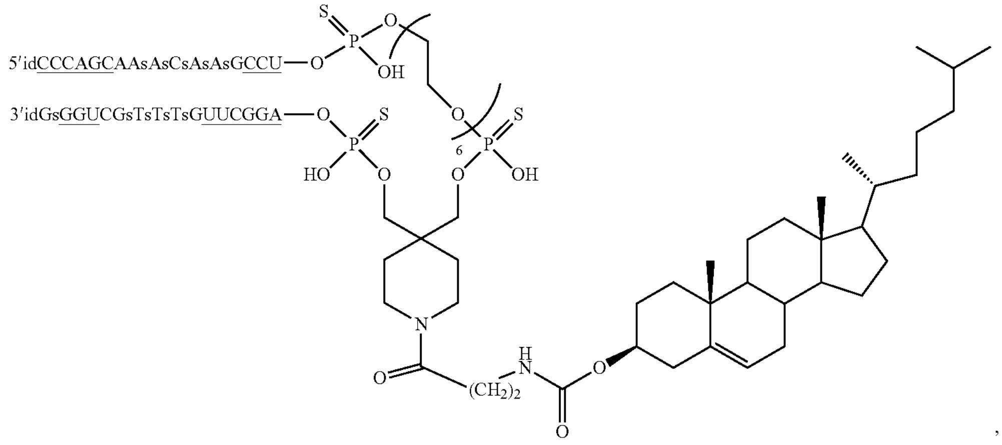

, respectively.

In another aspect, the idN are present and:

when idN is present and is idT at the 5' end and the 3' end, N is T, and the underlined 2'-modified nucleotides are 2'-deoxy-2'-fluoroarabinonucleotides (F-ANA), the molecule is OX421:

SEQ ID NOs: 9 and 10

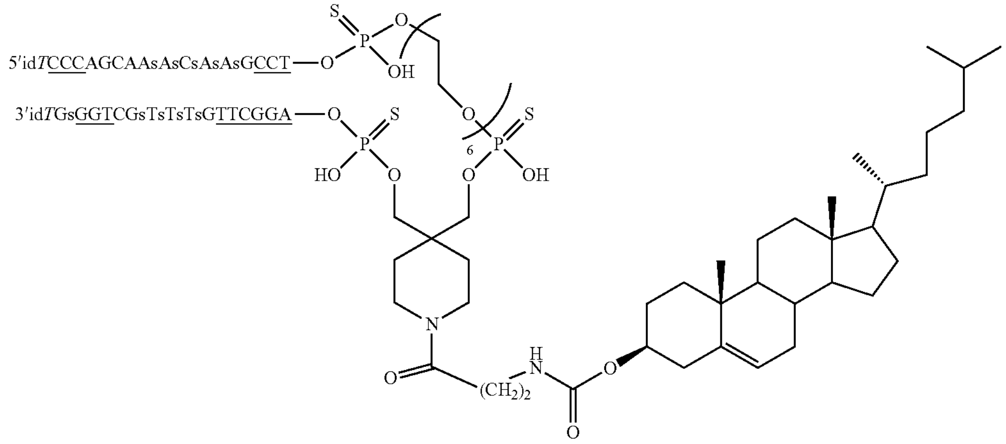

, respectively, when idN is present and is idT at the 5' end and the 3' end, N is U, and the underlined 2'-modified nucleotides are 2'-O-methyl nucleotides (2'-OMe), the molecule is OX422:

SEQ ID NOs: 11 and 12

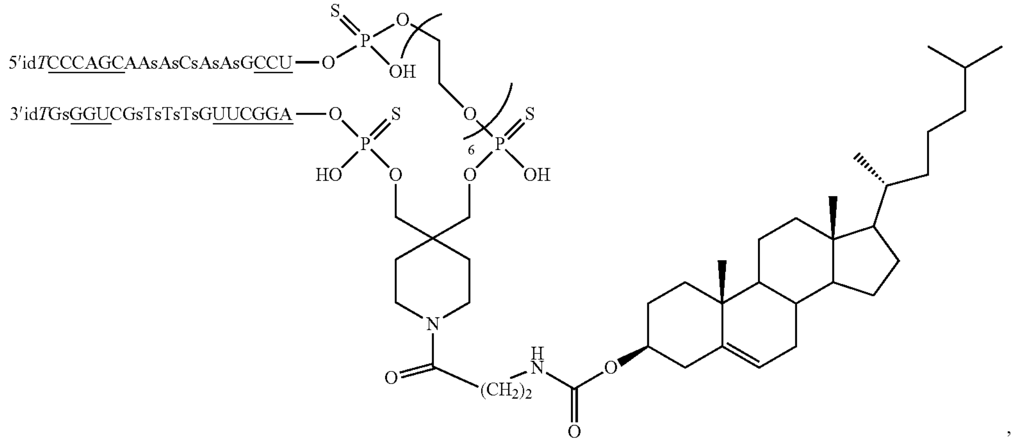

, respectively,

In another particular aspect, the conjugated nucleic acid molecule is:

SEQ ID NOs: 1 and 2

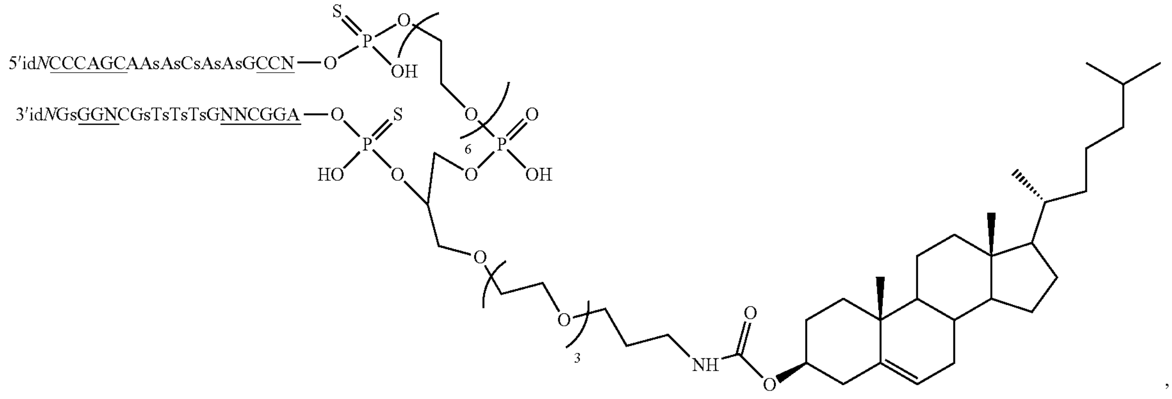

, respectively, wherein each occurrence of N is independently T or U, wherein idN is an inverted nucleotide and is present or absent, and when idN is present, it is preferably an inverted thymidine, idT, wherein internucleotide linkages "s" refer to phosphorothioate internucleotide linkages; and wherein the underlined nucleotides are 2'-modified nucleotides, preferably 2'-deoxy-2'-fluoroarabinonucleotides (F-ANA) or 2'O-Methyl nucleotides (2'-OMe), or the pharmaceutically acceptable salts thereof.

In a very particular aspect, the conjugated nucleic acid molecule is:

SEQ ID NOs: 3 and 4

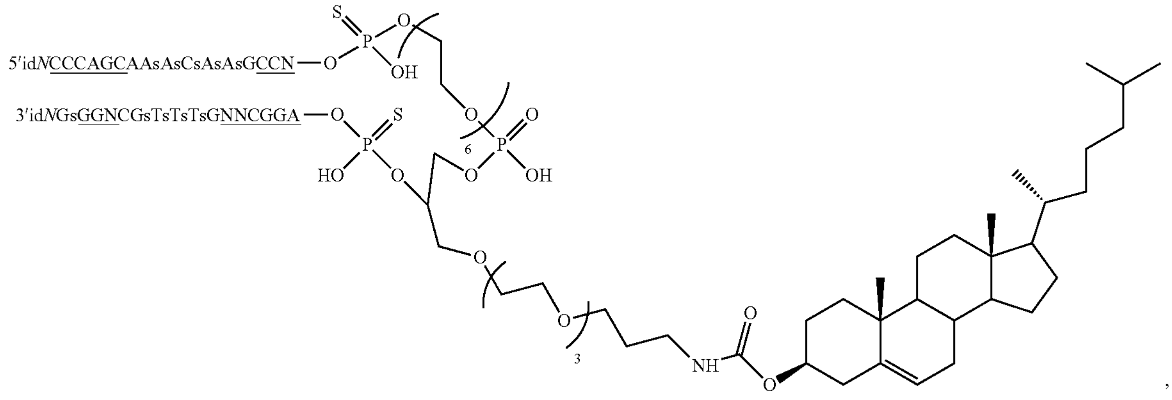

, respectively, wherein idN is an inverted nucleotide and is present or absent, and when idN is present, it is preferably an inverted thymidine idT, wherein N is T, wherein internucleotide linkages "s" refer to phosphorothioate internucleotide linkages; and wherein the underlined nucleotides are 2'-modified nucleotides, preferably 2'-deoxy-2'-fluoroarabinonucleotides (F-ANA) or 2'O-Methyl nucleotides (2'-OMe), or the pharmaceutically acceptable salts thereof.

In a very particular aspect, the conjugated nucleic acid molecule is:

SEQ ID NOs: 5 and 6

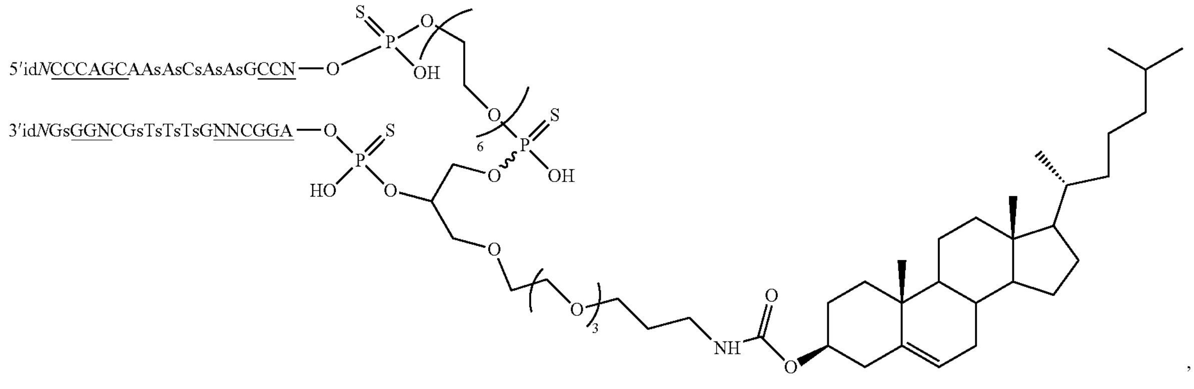

, respectively, wherein idN is an inverted nucleotide and is present or absent, and when idN is present, it is preferably an inverted thymidine idT, wherein N is U, wherein internucleotide linkages "s" refer to phosphorothioate internucleotide linkages; and wherein the underlined nucleotides are 2'-modified nucleotides, preferably 2'-deoxy-2'-fluoroarabinonucleotides (F-ANA) or 2'O-Methyl nucleotides (2'-OMe), or the pharmaceutically acceptable salts thereof.

In a preferred aspect, when the idN are absent, N is U and the underlined 2'-modified nucleotides are 2'-O-methyl nucleotides (2'-OMe), the molecule is OX423:

SEQ ID NOs: 7 and 8

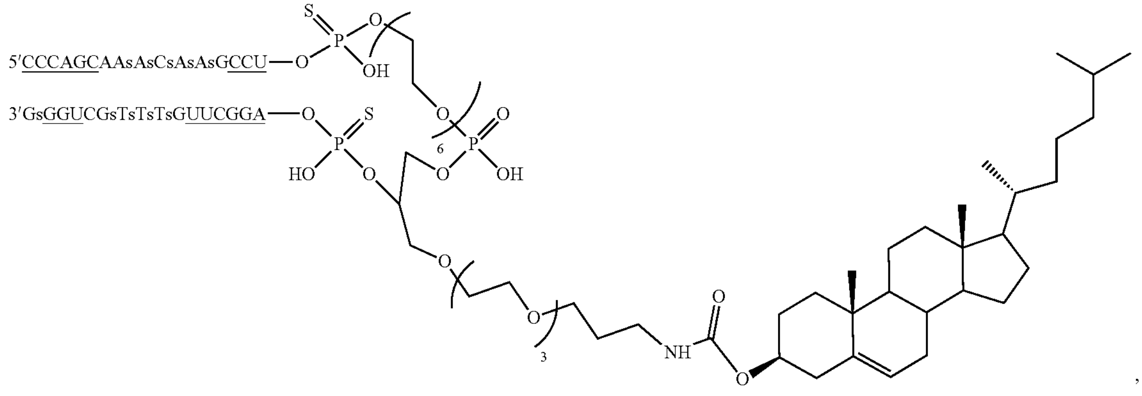

, respectively.

In another particular aspect, the conjugated nucleic acid molecule is:

SEQ ID Nos: 1 and 2

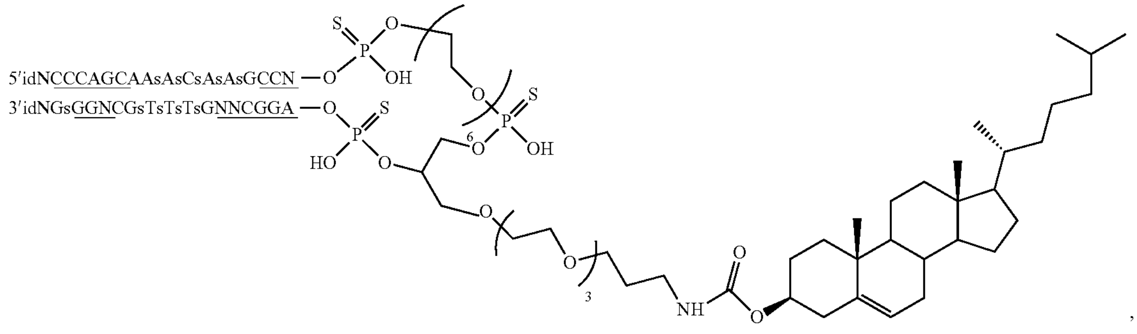

, respectively, wherein each occurrence of N is independently T or U wherein idN is an inverted nucleotide and is present or absent, and when idN is present, it is preferably an inverted thymidine idT, wherein internucleotide linkages "s" refer to phosphorothioate internucleotide linkages; and wherein the underlined nucleotides are 2'-modified nucleotides, preferably 2'-deoxy-2'-fluoroarabinonucleotides (F-ANA) or 2'O-Methyl nucleotides (2'-OMe), or the pharmaceutically acceptable salts thereof.

In a very particular aspect, the conjugated nucleic acid molecule is:

SEQ ID NOs: 3 and 4

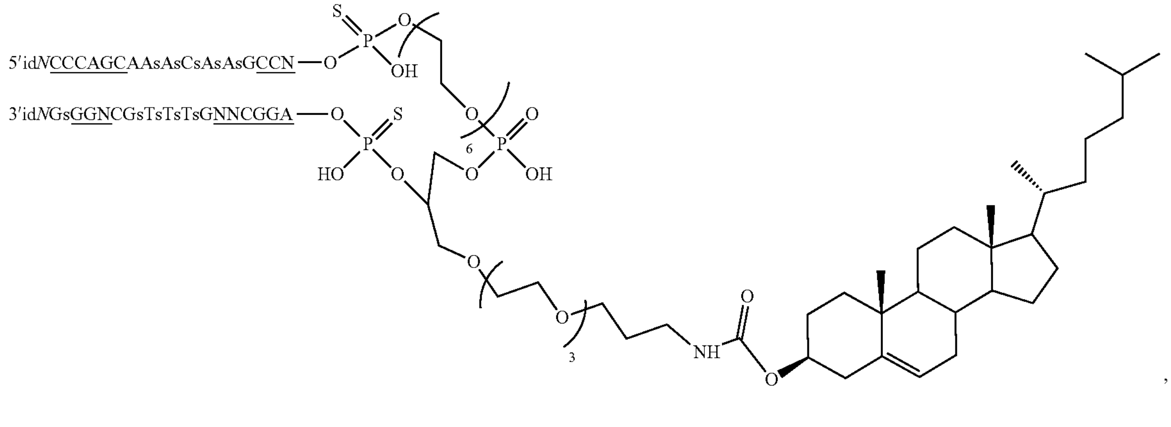

, respectively, wherein idN is an inverted nucleotide and is present or absent, and when idN is present, it is preferably an inverted thymidine idT, wherein N is T, wherein internucleotide linkages "s" refer to phosphorothioate internucleotide linkages; and wherein the underlined nucleotides are 2'-modified nucleotides, preferably 2'-deoxy-2'-fluoroarabinonucleotides (F-ANA) or 2'O-Methyl nucleotides (2'-OMe), or the pharmaceutically acceptable salts thereof.

In another particular aspect, the conjugated nucleic acid molecule is:

SEQ ID NOs: 5 and 6

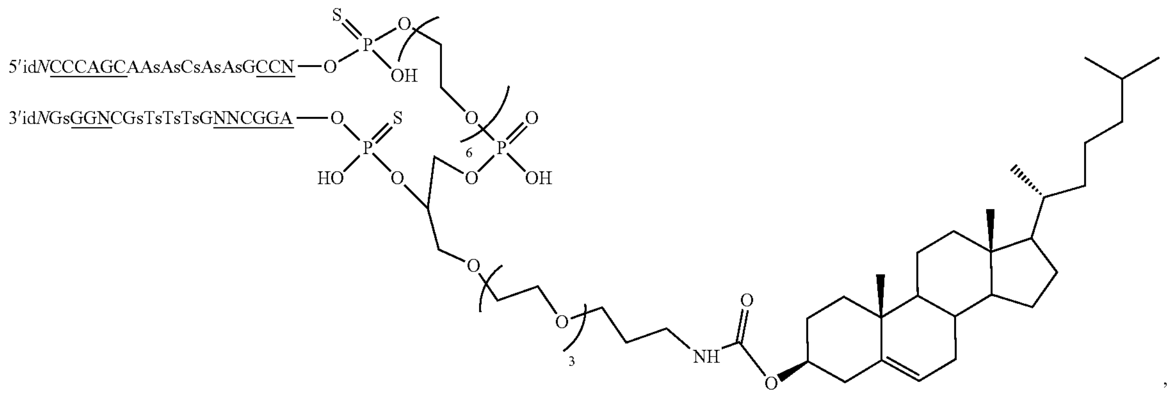

, respectively, wherein idN is an inverted nucleotide and is present or absent, and when idN is present, it is preferably an inverted thymidine idT, wherein N is U, wherein internucleotide linkages “s” refer to phosphorothioate internucleotide linkages; and wherein the underlined nucleotides are 2'-modified nucleotides, preferably 2'-deoxy-2'-fluoroarabinonucleotides (F-ANA) or 2'O-Methyl nucleotides (2'-OMe), or the pharmaceutically acceptable salts thereof.

In a preferred aspect, when the idN are absent, N is U and the underlined 2'-modified nucleotides are 2'-O-methyl nucleotides (2'-OMe), the molecule is OX424:

SEQ ID NOs: 7 and 8

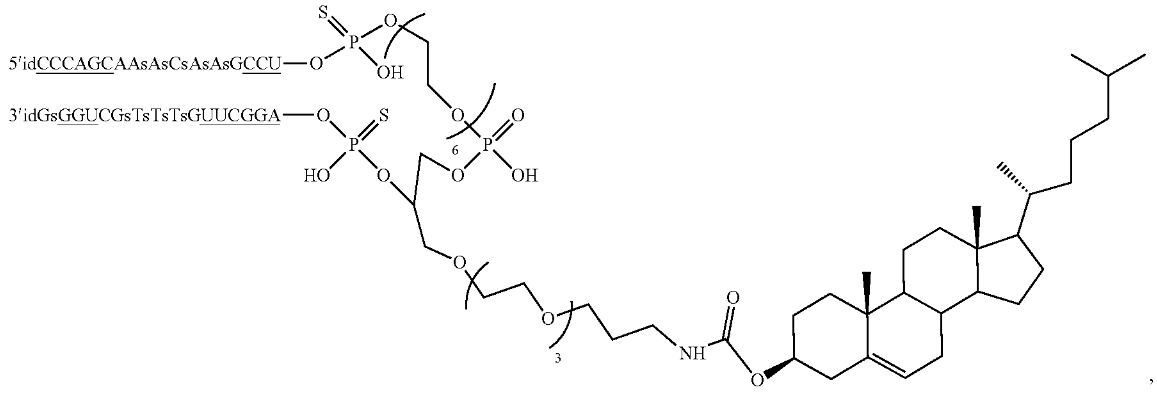

, respectively.

In a very particular aspect, the conjugated nucleic acid molecule is OX425:

SEQ ID NOs: 19 and 20

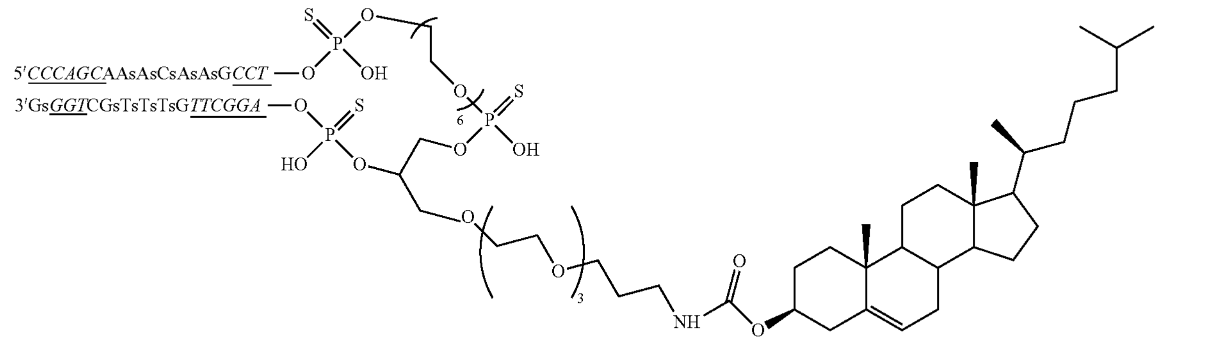

respectively, wherein internucleotide linkages “s” refer to phosphorothioate internucleotide linkages; and wherein the underlined 2'-modified nucleotides are 2'-deoxy-2'-fluoroarabinonucleotides (FANA).

The present invention also relates to a pharmaceutical composition comprising a conjugated nucleic acid molecule according to the present disclosure. Optionally, the pharmaceutical composition further comprises or can be combined with an additional therapeutic agent, preferably selected from an immunomodulator such as an immune checkpoint inhibitor (ICI), a T-cell-based cancer immunotherapy such as adoptive cell transfer (ACT), genetically modified T-cells or engineered T-cells such as chimeric antigen receptor cells (CAR-T cells), or a conventional chemotherapeutic, radiotherapeutic or anti-angiogenic agent, or targeted immunotoxin. In a particular aspect, the additional therapeutic agent is an immune checkpoint inhibitor (ICI), preferably an inhibitor of the PD-1/PD-L1 pathway, more preferably an anti-PD-1 antibody such as PDR001 (Novartis), Nivolumab (Bristol-Myers Squibb), Pembrolizumab (Merck & Co), Pidilizumab (CureTech), MEDIO680 (Medimmune), REGN2810 (Regeneron), TSR-042 (Tesaro), PF-06801591 (Pfizer), BGB-A317 (Beigene), BGB-108 (Beigene), INCSHR1210 (Incyte), AMP-224 (Amplimmune), IBI308 (Innovent and Eli Lilly), JS001, JTX-4014 (Jounce Therapeutics), PDR001 (Novartis) or MGA012 (Incyte and MacroGenics).

The present invention also relates to a conjugated nucleic acid molecule or a pharmaceutical composition or veterinary composition according to the present disclosure for use as a drug, in particular for use for the treatment of cancer. It further relates to a method of treating a cancer in a subject in need thereof, comprising administering a therapeutically efficient amount of a conjugated nucleic acid molecule or a pharmaceutical composition according to the present invention, repeatedly or chronically. Optionally, the method comprises administering repeated cycles of treatment, preferably for at least two cycles of administration, even more preferably at least three or four cycles of administration.

Repeated or chronic administrations of a conjugated nucleic acid molecule according to the invention does not lead cancer cells to develop resistance to the therapy. It can be used in combination with an immunomodulator, such as an immune checkpoint inhibitor (ICI), or in combination with T-cell-based cancer immunotherapy including adoptive cell transfer (ACT), genetically modified T-cells or engineered T-cells such as chimeric antigen receptor cells (CAR-T cells). In a particular aspect, the immune checkpoint inhibitor (ICI), preferably an inhibitor of the PD-1/PD-L1 pathway, more preferably an anti-PD-1 antibody such as PDR001 (Novartis), Nivolumab (Bristol-Myers Squibb), Pembrolizumab (Merck & Co), Pidilizumab (CureTech), MEDI0680 (Medimmune), REGN2810 (Regeneron), TSR-042 (Tesaro), PF-06801591 (Pfizer), BGB-A317 (Beigene), BGB-108 (Beigene), INCSHR1210 (Incyte), AMP-224 (Amplimmune), IBI308 (Innovent and Eli Lilly), JS001, JTX-4014 (Jounce Therapeutics), PDR001 (Novartis) or MGA012 (Incyte and MacroGenics). Indeed, a synergistic effect has been observed when the conjugated nucleic acid molecule according to the invention is combined with immune checkpoint inhibitor (ICI), preferably an inhibitor of the PD-1/PD-L1 pathway, more preferably an anti-PD-1 antibody.

Accordingly, the conjugated nucleic acid molecule or the pharmaceutical composition is for use in the treatment of cancer, in combination with an additional therapeutic agent, preferably selected from an immunomodulator such as an immune checkpoint inhibitor (ICI), a T-cell-based cancer immunotherapy such as adoptive cell transfer (ACT), genetically modified T-cells or engineered T-cells such as chimeric antigen receptor cells (CAR-T cells), or a conventional chemotherapeutic, radiotherapeutic or anti-angiogenic agent, or targeted immunotoxin. In a particular aspect, the additional therapeutic agent is an immune checkpoint inhibitor (ICI), preferably an inhibitor of the PD-1/PD-L1 pathway, more preferably an anti-PD-1 antibody such as PDR001 (Novartis), Nivolumab (Bristol-Myers Squibb), Pembrolizumab (Merck & Co), Pidilizumab (CureTech), MEDIO680 (Medimmune), REGN2810 (Regeneron), TSR-042 (Tesaro), PF-06801591 (Pfizer), BGB-A317 (Beigene), BGB-108 (Beigene), INCSHR1210 (Incyte), AMP-224 (Amplimmune), IBI308 (Innovent and Eli Lilly), JS001, JTX-4014 (Jounce Therapeutics), PDR001 (Novartis) or MGA012 (Incyte and MacroGenics).

In a particular aspect, the cancer is selected from leukemia, lymphoma, sarcoma, melanoma, and cancers of the head and neck, kidney, ovary, pancreas, prostate, thyroid, lung, esophagus, breast, bladder, brain, colorectum, liver, endometrium and cervix. Optionally, the cancer is a homologous recombination deficient tumor. Alternatively, the cancer is a homologous recombination proficient tumor.

In a particular aspect, the present invention also relates to a way for a possible selection strategy or a clinical stratification strategy for patients with tumors carrying deficiencies in the $NAD^+$ synthesis. These patients could be better responders for the drug treatment according to the present invention, in particular patients with tumors carrying both DNA repair pathways deficiencies (for example ERCC1 and ATM deficiency) or IDHs mutations.

In a particular aspect, the conjugated nucleic acid molecule or the pharmaceutical composition is for use for a targeted effect against tumor cells carrying deficiencies in the $NAD^+$ synthesis in the treatment of cancer. More particularly, the tumor cells further carry DNA repair pathways deficiencies selected from ERCC1 or ATM deficiency or IDHs mutations.

BRIEF DESCRIPTION OF THE DRAWINGS

(FIG. 1A) Representative images of PARylation 48 hours after OX401 or OX413 treatment; (FIG. 1B) Quantification of % positive cells with PARylation signal (PAR+ cells).

(FIG. 3A) Representative images of PARylation 48 hours after OX413 treatment (200 nM). (FIGS. 3B, 3C) Levels of cells with micronuclei (MN) (FIG. 3B) or cytoplasmic chromatin fragments (CCFs) (FIG. 3C) were analyzed by immunofluorescence 48 hours after OX413 (50 and 100 nM) treatment. (FIGS. 3D, 3F, 3G) Flow cytometry analysis of (FIG. 3D) pSTING, (FIG. 3F) PD-L1, and (FIG. 3G) MIC-A biomarkers. (FIG. 3E) Secreted CCL5 was analyzed in cell supernatant by ELISA 48 hours after OX413 (200 nM) treatment.

(FIG. 4E) Tumor-infiltrating leucocytes (TILs) percentages (CD45+, CD3+, DCs cell, NKs cells) were determined by flow cytometry analysis.

(FIG. 8A) Interaction of OX425 with PARP1 was assessed using recombinant PARP1 proteins (rPARP1) and gel shift assay. (FIG. 8B) Representative images of PARylation in MDA-MB-231 and MDA-MB-436 cells non-treated (Control) or treated with OX425 (100 to 500 nM) for 24 hours. Mean Fluorescence Intensity (MFI) was evaluated to assess the level of PARylation.

(FIG. 9A) Sensitivity to increasing doses of OX425 (up to 2 μM) of different tumor cell lines with different homologous recombination (HR) repair status (HR deficient, HRD, or HR proficient, HRP) was assessed using XTT assay at day 6 after treatment. $IC_{50}$s were calculated using GraphPad-Prism software. (FIG. 9B) Sensitivity of PBMCs to different DNA repair inhibitors was assessed by cell counting on day 3 after treatment.

(FIG. 10A) Sensitivity to OX425 of UWB1.289 BRCA1 mutated ovarian cancer cells (UWB1.289) compared to their BRCA1 complemented counterparts (UWB1.289 BRCA1) was assessed using XTT assay 6 days after treatment. $IC_{50}$s were calculated using GraphPadPrism software. (FIG. 10B) Cancer cell lines with different mutational status were grouped in homologous recombination deficient (HRD) or proficient (HRP) cells and compared analysis of these two groups regarding their sensitivity to OX425 or olaparib performed using unpaired student t test. ns, not significant; *, $p<0.05$.

(FIG. 11A) changes of MDA-MB-436 CDXs tumor size after olaparib continuous treatment alone at 100 mg/kg—5 days/week (green curve—mean of 10 independent mice) or olaparib+OX425 10 mg/kg 1×/week, introduced at day 30 after olaparib start (red curve—mean of 10 independent mice). (FIG. 11B) % of tumor size change at day 74 (end of treatment) compared to day 0 (treatment start) by mice (n=10). Tumors that progressed to more than +20% compared to day 0 are considered progressing, between +20% and −30%, are considered stable, between −30% and −99%, partial response, and 100% as complete response, analogous to RECIST criteria. (FIG. 11C) % of body weight change compared to day 0. (FIG. 11D) Homologous recombination repair functionality in the MDA-MB-436 cell-derived xenograft has been analyzed during olaparib treatment initiation and at early and late resistance emergence, using the RAD51 IHC staining assay. HRD, homologous recombination deficient; HRP, Homologous recombination proficient.

(FIG. 12F) PARP activation was also assessed in PAN02-derived xenografts, as well as (FIG. 12G) tumor-infiltrating lymphocytes (TILs, CD45+ cells) and (FIG. 12H) effects of tumor growth delay in tumors treated with OX425 at 25 mg/kg, 2×/week during three weeks.

(FIG. 13A) % of CD45+ and CD3+ normalized by the total number of cells obtained after tumor dissociation. (FIG. 13B) Tumor Infiltration Lymphocytes (TILs) CD3+, CD4+ and CD8+ % were quantified. (FIG. 13C) Infiltration of a specific Treg like population (CD45+CD4+CD49b+) in tumor (n=6).

DETAILED DESCRIPTION OF THE INVENTION

Figure 1A:
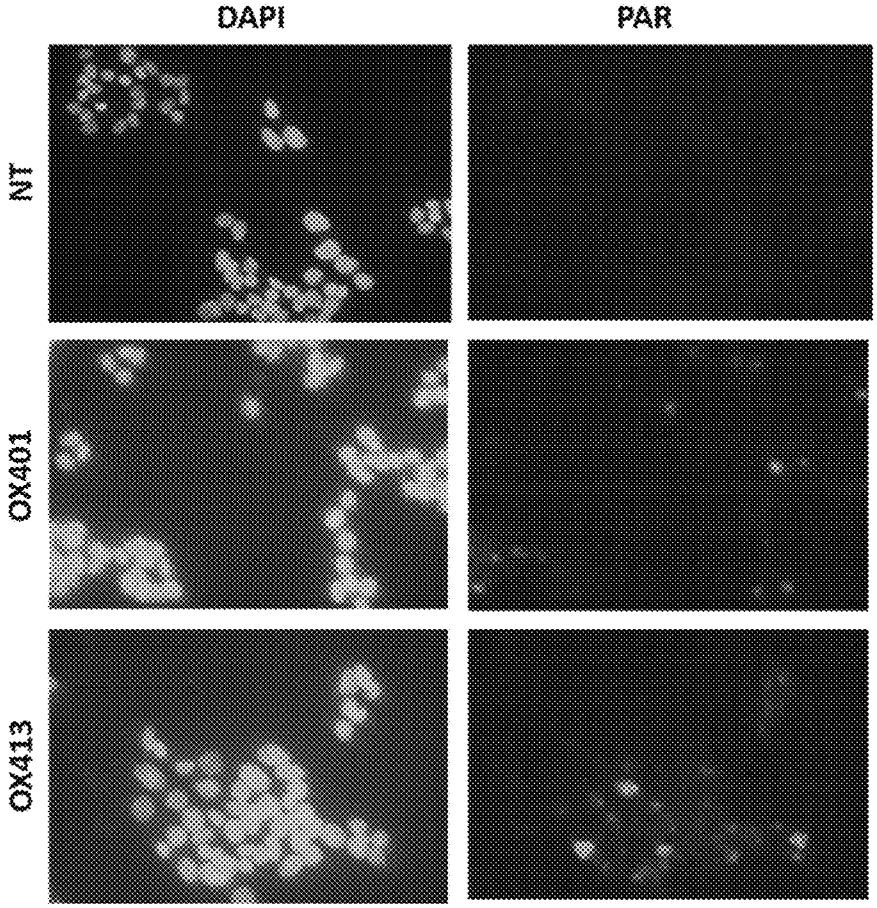
FIGS. 1A and 1B. OX413-induced target engagement. Cells were treated with OX413 (5 μM) or OX401 (5 μM), and PARP activation was assessed by measuring cellular PARylation.
Figure 1B:
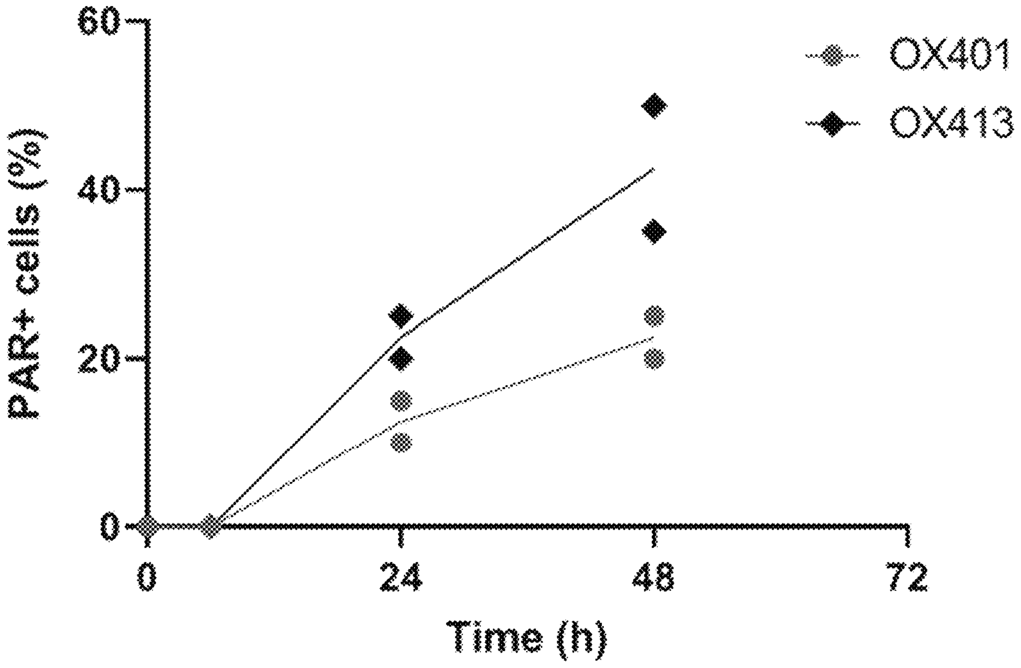

The present invention relates to new nucleic acid molecules conjugated to a molecule facilitating the endocytosis such as cholesterol-nucleic acid conjugates, which target and activate specifically PARPs, inducing a profound down regulation of cellular NAD and therefore particularly dedicated for cancer treatment, in particular on cancer cells that display NAD deficiency due to DNA repair genes deficiency (for example ERCC1 and ATM deficiency) or IDHs (Isocitrate dehydrogenase) mutations.

The present invention relates to new nucleic acid molecules conjugated to a molecule facilitating the endocytosis such as cholesterol-nucleic acid conjugates, which target DDR mechanisms and are also STING agonists allowing their combination with immune checkpoint therapy (ICT) for an optimal treatment of cancer.

New conjugated nucleic acid molecules according to the invention provide:

1) The activation of PARP without activation of DNA-PK by the conjugated nucleic acid molecules of the present invention leads to an increase of cancer cells with micronuclei, cytoplasmic chromatin fragments (CCF) and cytotoxicity by standalone use in comparison with Dbait molecules.
2) The specific increase of micronuclei (MN) and cytoplasmic chromatin fragments (CCF) in cancer cells leads to an early increase of STING pathway activation as shown by the increase of inflammatory cytokines (CCL5) release and PD-L1 and NKG2D ligands (MIC-A) expression on cancer cells. These effects are specific to cancer cells. Such a cancer cell specificity precludes general and extensive inflammation with subsequent deleterious possible side effects.
3) The activation of the STING pathway through DNA repair pathway inhibition and generation of either micronuclei and CCFs represent a very attractive way to specifically activate the STING pathway in tumor cells, in particular by innate immunity activation.
4) The conjugated nucleic acid molecules according to the invention provide a high antitumor activity in both homologous recombination deficient and proficient tumors, on the contrary of current PARP inhibitors.
5) The conjugated nucleic acid molecules according to the invention mediate multiple immunostimulatory effects, making it an interesting therapeutic strategy in combination with immunotherapy, especially in "cold" tumors. A synergistic effect has been observed when the conjugated nucleic acid molecules are used in combination with immune checkpoint inhibitors.

Based on these observations, the present invention relates to:

- a conjugated nucleic acid molecule as described herein;
- a pharmaceutical composition comprising a conjugated nucleic acid molecule as described herein and a pharmaceutically acceptable carrier, in particular for use in the treatment of cancer;
- a conjugated nucleic acid molecule as described herein for use as a drug, in particular for use in the treatment of cancer;
- the use of a conjugated nucleic acid molecule as described herein for the manufacture of a drug, in particular for use in the treatment of cancer;
- a method for treating a cancer in a patient in need thereof, comprising administering an effective amount of a conjugated nucleic acid molecule as disclosed herein;
- a pharmaceutical composition comprising a conjugated nucleic acid molecule as described herein, an additional therapeutic agent and a pharmaceutically acceptable carrier, in particular for use in the treatment of cancer:
- a product or kit containing (a) a conjugated nucleic acid molecule as disclosed herein, and optionally b) an additional therapeutic agent, as a combined preparation for simultaneous, separate or sequential use, in particular in the treatment of cancer;
- a combined preparation which comprises (a) a hairpin nucleic acid molecule as disclosed below, b) an additional therapeutic agent as described herein for simultaneous, separate or sequential use, in particular in the treatment of cancer;
- a pharmaceutical composition comprising a conjugated nucleic acid molecule as disclosed herein, for the use in the treatment of cancer in combination with an additional therapeutic agent;
- the use of a pharmaceutical composition comprising a conjugated nucleic acid molecule as disclosed herein for the manufacture of a medicament for the treatment of cancer in combination with an additional therapeutic agent;
- a method for treating a cancer in a patient in need thereof, comprising administering an effective amount of a) a conjugated nucleic acid molecule as disclosed herein, and b) an effective amount of an additional therapeutic agent;
- a method for treating a cancer in a patient in need thereof, comprising administering an effective amount of a pharmaceutical composition comprising a conjugated nucleic acid molecule as disclosed herein, and an effective amount of an additional therapeutic agent;
- a method for increasing the efficiency of a treatment of a cancer with a therapeutic antitumor agent, or for enhancing tumor sensitivity to treatment with a therapeutic antitumor agent in a patient in need thereof, comprising administering an effective amount of a conjugated nucleic acid molecule as disclosed herein;

- a method for treating cancer comprising administering a conjugated nucleic acid molecule as disclosed herein, repeatedly or chronically, by repeated cycles of treatment, preferably for at least two cycles of administration, even more preferably at least three or four cycles of administration;
- a method of treating cancer in patients with tumor cells carrying deficiencies in the NAD+ synthesis, and optionally DNA repair pathways deficiencies selected from ERCC1 or ATM deficiency or IDHs mutations.

Definitions

Whenever within this whole specification "treatment of a cancer" or the like is mentioned with reference to the pharmaceutical composition, kit, product and combined preparation of the invention, there is meant: a) a method for treating a cancer, said method comprising administering a pharmaceutical composition, kit, product and combined preparation of the invention to a patient in need of such treatment; b) a pharmaceutical composition, kit, product and combined preparation of the invention for use in the treatment of a cancer; c) the use of a pharmaceutical composition, kit, product and combined preparation of the invention for the manufacture of a medicament for the treatment of a cancer; and/or d) a pharmaceutical composition, kit, product and combined preparation of the invention for use in the treatment a cancer.

Within the context of the invention, the term "treatment" denotes curative, symptomatic, and preventive treatment. Pharmaceutical compositions, kits, products and combined preparations of the invention can be used in humans with existing cancer or tumor, including at early or late stages of progression of the cancer. The pharmaceutical compositions, kits, products and combined preparations of the invention will not necessarily cure the patient who has the cancer but will delay or slow the progression or prevent further progression of the disease, improving thereby the patients' condition. In particular, the pharmaceutical compositions, kits, products and combined preparations of the invention reduce the development of tumors, reduce tumor burden, produce tumor regression in a mammalian host and/or prevent metastasis occurrence and cancer relapse. In treating the cancer, the pharmaceutical composition, kit, product and combined preparation of the invention is administered in a therapeutically effective amount.

The terms "kit", "product" or "combined preparation", as used herein, define especially a "kit-of-parts" in the sense that the combination partners (a) and (b), as defined above can be dosed independently or by use of different fixed combinations with distinct amounts of the combination partners (a) and (b), i.e. simultaneously or at different time points. The components of the kit-of-parts can then, e.g., be administered simultaneously or chronologically staggered, that is at different time points and with equal or different time intervals for any part of the kit-of-parts. The ratio of the total amounts of the combination partner (a) to the combination partner (b), to be administered in the combined preparation can be varied. The combination partners (a) and (b) can be administered by the same route or by different routes.

By "effective amount" it is meant the quantity of the pharmaceutical composition, kit, product and combined preparation of the invention which prevents, removes or reduces the deleterious effects of cancer in mammals, including humans, alone or in combination with the other active ingredients of the pharmaceutical composition, kit, product or combined preparation. It is understood that the administered dose may be adapted by those skilled in the art according to the patient, the pathology, the mode of administration, etc.

The term "STING" refers to STtimulator of INterferon Genes receptor, also known as TMEM173, ERIS, MITA, MPYS, SAVI, or NET23). As used herein, the terms "STING" and "STING receptor" are used interchangeably, and include different isoforms and variants of STING. The mRNA and protein sequences for human STING isoform 1, the longest isoform, have the NCBI Reference Sequence [NM_198282.3] and [NP_938023.1]. The mRNA and protein sequences for human STING isoform 2, a shorter isoform have the NCBI Reference Sequence [NM_001301738.1] and [NP_001288667.1].

The term "STING activator", as used herein, refers to a molecule capable of activating the STING pathway. Activation of the STING pathway may include, for example, stimulation of inflammatory cytokines, including interferons, such as type 1 interferons, including IFN-α, IFN-β, type 3 interferons, e.g., IFN-λ, IP-10 (interferon-7-inducible protein also known as CXCL10), PD-L1, TNF, IL-6, CXCL9, CCL4, CXCL11, NKG2D ligand (MICA/B), CCL5, CCL3, or CCL8. Activation of the STING pathway may also include stimulation of TANK binding kinase (TBK) 1 phosphorylation, interferon regulatory factor (IRF) activation (e.g., IRF3 activation), secretion of IP-10, or other inflammatory proteins and cytokines. Activation of the STING pathway may be determined, for example, by the ability of a compound to stimulate activation of the STING pathway as detected using an interferon stimulation assay, a reporter gene assay (e.g., a hSTING wt assay, or a THP-1 Dual assay), a TBK1 activation assay, IP-10 assay, or other assays known to persons skilled in the art. Activation of the STING pathway may also be determined by the ability of a compound to increase the level of transcription of genes that encode proteins activated by STING or the STING pathway. Such activation may be detected, for example, using an RNAseq assay.

Activation of the STING pathway can be determined by one or more "STING assays" selected from: an interferon stimulation assay, a hSTING wt assay, a THP1-Dual assay, a TANK binding kinase 1 (TBK1) assay, an interferon-γ-inducible protein 10 (IP-10) secretion assay or a PD-L1 assay.

More specifically, a molecule is a STING activator if it is able to stimulate production of one or more STING-dependent cytokines in a STING-expressing cell at least 1.1-fold, 1.2-fold, 1.3-fold, 1.4-fold, 1.5-fold, 1.6-fold, 1.7-fold, 1.8-fold, 1.9-fold, 2-fold or greater than an untreated STING-expressing cell. Preferably, the STING-dependent cytokine is selected from interferon, type 1 interferon, IFN-α, IFN-β, type 3 interferon, IFN-λ, CXCL10 (IP-10), PD-L1 TNF, IL-6, CXCL9, CCL4, CXCL11, NKG2D ligand (MICA/B), CCL5, CCL3, or CCL8, more preferably CCL5 or CXCL10.

Conjugated Nucleic acid Molecules

An additional advantage of some of the conjugated nucleic acid molecules according to the present invention is based on the fact that they can be synthesized as one molecule by only using oligonucleotide solid phase synthesis, thereby allowing low costs and a high manufacturing scale.

The conjugated nucleic acid molecule of the present invention comprises a 16 to 17-base pairs double-stranded nucleic acid moiety, the 5' end of the first strand and the 3' end of the complementary strand being linked together by a loop, and optionally a molecule facilitating the endocytosis which is linked to the loop. The other end of the double-stranded nucleic acid moiety is free.

Conjugated nucleic acid molecules according to the present invention may be defined by a number of characteristics necessary for their therapeutic activity, such as their 16 to 17-bp length, the presence of at least one free end, and the presence of a double stranded portion, preferably a double-stranded DNA portion with the presence of phosphorothioate internucleotide linkages and, nucleotide modifications corresponding to position 2' of the ribose of the nucleotides. The particular combination of phosphorothioate internucleotide linkages and 2'-modified nucleotides is surprisingly associated with an improved activity and pharmacokinetic.

The conjugated nucleic acid molecule is capable of activating PARP-1 protein. On the other hand, the conjugated nucleic acid molecule does not activate DNA-PK.

The present invention also relates to a pharmaceutically acceptable salt of the conjugated nucleic acid molecule of the present invention.

Nucleic Acid Molecules

The nucleic acid molecules of the present invention comprise a double-stranded nucleic acid moiety, the 5' end of the first strand and the 3' end of the complementary strand, being linked together by a loop, the length of the conjugated nucleic acid molecules is of 16 to 17-base pairs (bp), allowing appropriate binding and activation of PARP (PARP-1) protein and being insufficient to allow appropriate binding of Ku protein complex comprising Ku and DNA-PKcs proteins. By "bp" is intended that the molecules comprise a double stranded portion of the indicated length.

The conjugated nucleic acid molecules do not hybridize, under stringent conditions, with human genomic DNA.

In one aspect, thymidines can be replaced by 2'-deoxy-2'-fluoroarabinothymidine, guanosines can be replaced by 2'-deoxy-2'-fluoroarabinoguanosine; cytidines can be replaced by 2'-deoxy-2'-fluoroarabinocytidine; or adenines can be replaced by 2'-deoxy-2'-fluoroarabinoadenine.

In another embodiment, uridine can be replaced by 2'-O-methyl-uridine (2'-OMe-uridine), guanosine can be replaced by 2'-O-methyl-guanosine (2'-OMe-guanosine); cytidine can be replaced by 2'-O-methyl-cytidine (2'-OMe-cytidine); adenine can be replaced by 2'-O-methyl-adenine (2'-OMe-adenine); or thymidine can be replaced by 2'-O-methyl-thymidine (2'-OMe-thymidine).

When an interaction between the 2' position of the nucleotide and PARP-1 is identified, the nucleotide is let without any modification at the 2' position. When an interaction between inter-junction of the nucleotides and PARP-1 is identified, the modifications on the nucleotides are 2' modifications. When the nucleotides are without any known interaction with PARP-1, the internucleotide linkage of these nucleotides were chemically modified by the introduction of phosphorothioates ("s") in order to protect them from degradation. As the double-stranded nucleic acid molecules have 16 to 17 base pairs, symmetrical chemical modifications have been done, namely there are 6 2'-modified nucleotides at the 5' end of each strand and 3 2'-modified nucleotides at the 3' end of each strand and most of the nucleotides between these stretches of 2'-modified nucleotides have a phosphorothioate linkage.

According to one embodiment, the conjugated nucleic acid molecules comprise a modification corresponding to position 2' of the ribose. For instance, the conjugated nucleic acid molecules may comprise at least one 2'-modified nucleotide, e.g., having a 2'-deoxy, 2'-deoxy-2'-fluoro, 2'-O-methyl (2'-OMe), 2'-O-methoxyethyl (2'-O-MOE), 2'-O-aminopropyl (2'-O-AP), 2'-O-dimethylaminoethyl (2'-O-DMAE), 2'-O-dimethylaminopropyl (2'-O-DMAP), 2'-O-dimethylaminoethyloxyethyl (2'-O-DMAEOE) or 2'-O—N-methylacetamido (2'-O-NMA) modification or e.g. a 2'-deoxy-2'-fluoroarabinonucleotide (FANA). In another embodiment, the conjugated nucleic acid molecules comprise a modification at the 2' position corresponding to 2'-deoxy-2'-fluoroarabinonucleotides (FANA), and 2'-O-methyl (2'-OMe).

In a particular aspect, the conjugated nucleic acid molecules have 2'-deoxy-2'-fluoroarabinonucleotides (F-ANA). In another aspect, the 2'-modified nucleotides are 2'-O-methyl- nucleotides (2'-OMe).

Optionally, the double-stranded nucleic acid molecules can have at their 5' free end and/or 3' free end an inverted nucleotide (idN). Optionally, the double-stranded nucleic acid molecules can have at their 5' free end and 3' free end an inverted nucleotide (idN). The inverted nucleotide (idN) can be an inverted guanidine, adenine, cytidine or thymidine. Preferably, the inverted nucleotide (idN) is an inverted thymidine (idT). More particularly, an inverted nucleotide (idN) at the 5' free end is bound by a 5'-5' linkage and an inverted nucleotide (idN) at the 3' free end is bound by a 3'-3' linkage.

In a particular aspect, the double-stranded nucleic acid moiety has the following sequence SEQ ID NOs: 1 and 2

5'*idN*<u>CCCAGC</u>AAsAsCsAsAsG<u>CCN</u>
3'*idN*Gs<u>GGN</u>CGsTsTsTsG<u>NNCGGA</u>
Loop, respectively wherein each occurrence of N is independently T or U, wherein idN is an inverted nucleotide and is present or absent, wherein internucleotide linkages "s" refer to phosphorothioate internucleotide linkages; and, wherein the underlined nucleotides are 2'-modified nucleotides.

Optionally, all N are T. Optionally, all N are U.

Optionally, idN is absent. Optionally, idN is present. Optionally, idN is present at the 5' end. Optionally, idN is present at the 3' end. Optionally, idN is present at the 5' end and at the 3' end.

Optionally, the 2' modified nucleotide is independently selected from the group consisting of 2'-deoxy-2'-fluoro, 2'-O-methyl (2'-OMe), 2'-O-methoxyethyl (2'-O-MOE), 2'-O-aminopropyl (2'-O-AP), 2'-O-dimethylaminoethyl (2'-O-DMAE), 2'-O-dimethylaminopropyl (2'-O-DMAP), 2'-O-dimethylaminoethyloxyethyl (2'-O-DMAEOE), 2'-O—N-methylacetamido (2'-O-NMA) modification, 2'-deoxy-2'-fluoroarabinonucleotide (FANA), and 2' bridged nucleotides, preferably 2'-deoxy-2'-fluoroarabinonucleotides (FANA) and 2'-O-methyl (2'-OMe).

In a particular aspect, the 2' modified nucleotide is a 2'-deoxy-2'-fluoroarabinonucleotide (FANA). FANA adopts a DNA-like structure resulting in an unaltered recognition of the conjugated nucleic acid molecules by the proteins of interest. FANA include the following pyrimidine 2'-fluoroarabinonucleosides and purine 2'-fluoroarabinonucleosides:

9-(2-Deoxy-2-fluoro-ß-D-arabinofuranosyl)adenine (2'-FANA-A);

9-(2-Deoxy-2-fluoro-ß-D-arabinofuranosyl)guanine (2'-FANA-G);

1-(2-Deoxy-2-fluoro-ß-D-arabinofuranosyl)cytosine (2'-FANA-C);

1-(2-Deoxy-2-fluoro-ß-D-arabinofuranosyl)uracil (2'-FANA-U); and 1-(2-Deoxy-2-fluoro-ß-D-arabinofuranosyl)thymidine (2'-FANA-T).

In another aspect, the 2' modified nucleotide is a 2'-O-methyl-nucleotide (2'-OMe).

More specifically, uridine can be replaced by 2'-O-methyl-uridine (2'-OMe-uridine), guanosine can be replaced by 2'-O-methyl-guanosine (2'-OMe-guanosine); cytidine can be replaced by 2'-O-methyl-cytidine (2'-OMe-cytidine); adenine can be replaced by 2'-O-methyl-adenine (2'-OMe-adenine); or thymidine can be replaced by 2'-O-methyl-thymidine (2'-OMe-thymidine).

Loops

The loop is linked to the 5' end of the first strand and the 3' end of the complementary strand of the double-stranded moiety, and optionally to a molecule facilitating the endocytosis.

The loop preferably comprises a chain from 10 to 100 atoms, preferably from 15 to 25 atoms.

The molecules facilitating endocytosis are conjugated to the loop, optionally through a linker. Any linker known in the art may be used to covalently attach the molecule facilitating endocytosis to the loop. For instance, WO09/126933 provides a broad review of convenient linkers pages 38-45. The linker can be non-exhaustively, aliphatic chain, polyether, polyamine, polyamide, peptide, carbohydrate, lipid, polyhydrocarbon, or other polymeric compounds (e. g. oligoethylene glycols such as those having between 2 and 10 ethylene glycol units, preferably 3, 4, 5, 6, 7 or 8 ethylene glycol units, still more preferably 6 ethylene glycol units), as well as incorporating any bonds that may be break down by chemical or enzymatical way, such as a disulfide linkage, a protected disulfide linkage, an acid labile linkage (e.g., hydrazone linkage), an ester linkage, an ortho ester linkage, a phosphonamide linkage, a biocleavable peptide linkage, an azo linkage or an aldehyde linkage. Such cleavable linkers are detailed in WO2007/040469 pages 12-14, in WO2008/022309 pages 22-28.

The molecule facilitating the endocytosis is bound to the loop by any mean known by the person skilled in the art, optionally through an oligoethylene glycol spacer.

In a specific embodiment, the linker between the molecule facilitating endocytosis and the loop comprises C(O)—NH—$(CH_2—CH_2—O)_n$ or NH—C(O)—$(CH_2—CH_2—O)_n$, wherein n is an integer from 1 to 10, preferably n being selected from the group consisting of 3, 4, 5 and 6. In a very particular embodiment, the linker is CO—NH—$(CH_2—CH_2—O)_4$ (carboxamido tetraethylene glycol or also 13-O—[1-propyl-3-N-carbamoylcholesteryl]-tetraethyleneglycol radical).

In another specific embodiment, the linker between the molecule facilitating endocytosis and the loop molecule is dialkyl-disulfide {e.g., $(CH_2)_p$—S—S—$(CH_2)_q$ with p and q being integer from 1 to 10, preferably from 3 to 8, for instance 6}.

In a particular embodiment, the loop has been developed so as to be compatible with oligonucleotide solid phase synthesis. Accordingly, it is possible to incorporate the loop during the synthesis of the nucleic acid molecule, thereby facilitating the synthesis and reducing its cost.

The loop can have a structure selected from one of the following formulae:

$$—O—P(X)OH—O—\{[(CH_2)_2—O]_g—P(X)OH—O\}_r—K—O—P(X)OH—O—\{[(CH_2)_2—O]_h—P(X)OH—O—\}_s \quad (I)$$

with r and s being independently an integer 0 or 1; g and h being independently an integer from 1 to 7 and the sum g+h being from 4 to 7;

with K being

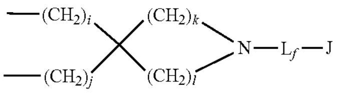

with i, j, k and l being independently an integer from 0 to 6, preferably from 1 to 3, L being a linker, f being an integer being 0 or 1, and J being a molecule facilitating the endocytosis or being H;

or $$—O—P(X)OH—O—[(CH_2)_d—C(O)—NH]_b—CHR—[C(O)—NH—(CH_2)_e]_d—O—P(X)OH—O— \quad (II)$$

with b and c being independently an integer from 0 to 4, and the sum b+c is from 3 to 7;

d and e being independently an integer from 1 to 3, preferably from 1 to 2;

with R being -$L_f$-J, wherein X is O or S at each occurrence of —O—P(X)OH—O—, L being a linker, preferably a linear alkylene and/or an oligoethylene glycol optionally interrupted by one or several groups selected from amino, amide, and oxo, and f being an integer being 0 or 1, and J being a molecule facilitating the endocytosis or being H.

When J is H, the molecule can be used as a synthon in order to prepare the molecule conjugated to a molecule facilitating the endocytosis. Alternatively, the molecule could also be used as a drug, without any conjugation to a molecule facilitating the endocytosis.

In a first aspect, the loop has a structure according to formula (I):

$$—O—P(X)OH—O—\{[(CH_2)_2—O]_g—P(X)OH—\}_r—K—O—P(X)OH—O—\{[(CH_2)_2—O]_h—P(X)OH—O—\}_s \quad (I)$$

X is O or S. X can vary among O and S at each occurrence of —O—P(X)OH—O— in formula (I). Preferably, X is S.

The sum g+h is preferably from 5 to 7, especially is 6. Accordingly, if r is 0, h can be from 5 to 7 (with s being 1); if g is 1, h can be from 4 to 6 (with r and s being 1); if g is 2, h can be from 3 to 5 (with r and s being 1); if g is 3, h can be from 2 to 4 (with r and s being 1); if g is 4, h can be from 1 to 3 (with r and s being 1); if g is 5, h can be from 1 to 2 (with r being 1 and s being 0 or 1); or if g is 6 or 7, s is 0 (with r being 1).

Preferably, i and j can be the same integer or can be different. i and j can be selected from the integer 0, 1, 2, 3, 4, 5 or 6, preferable 1, 2 or 3, still more particularly 1 or 2, especially 1.

Preferably, k and l are the same integer. In one aspect, k and l are an integer selected from 1, 2 or 3, preferably 1 or 2, more preferably 2.

Accordingly, K can be

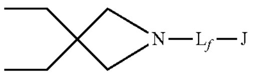

or

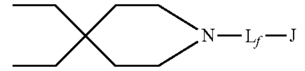

or $CH_2$—CH-($L_f$-J).

In a preferred aspect, K is

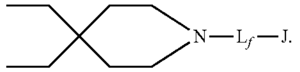

In one specific aspect, the loop has the formula (I)

$$—O—P(X)OH—O—\{[(CH_2)_2—O]_g—P(X)OH—O\}_r—K—O—P(X)OH—O—\{[(CH_2)_2—O]_h—P(X)OH—O—\}_s \quad (I)$$

with X being S, r being 1, g being 6, s being 0, and K being

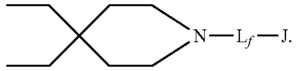

In another aspect, K can be —$CH_2$—CH($L_f$-J)-.

In a particular aspect, f is 1 and L-J is —C(O)—$(CH_2)_m$—NH—$[C(O)]_t$—$[(CH_2)_2—O]_n$—$(CH_2)_p$—$[C(O)]_v$-J, —C(O)—$(CH_2)_m$—NH—$[C(O)—CH_2—O]_t$—$[(CH_2)_2—O]_n$—$(CH_2)_p$—$[C(O)]_v$-J or —$CH_2$—O—$[(CH_2)_2—O]_n$—$(CH_2)_m$—NH—$(CH_2)_p$—C(O)-J with m being an integer from 0 to 10; n being an integer from 0 to 15; p being an integer from 0 to 4; t and v being an integer 0 or 1 with at least one among t and v being 1.

More particularly, f is 1 and L-J is selected in the group consisting of —C(O)—$(CH_2)_m$—NH—$[(CH_2)_2—O]_n$—$(CH_2)_p$—C(O)-J, —C(O)—$(CH_2)_m$—NH—C(O)—$[(CH_2)_2—O]_n$—$(CH_2)_p$-J, C(O)—$(CH_2)_m$—NH—C(O)—$CH_2$—O—$[(CH_2)_2—O]_n$—$(CH_2)_p$-J, —C(O)—$(CH_2)_m$—NH—C(O)—$[(CH_2)_2—O]_n$—$(CH_2)_p$—C(O)-J, —C(O)—$(CH_2)_m$—NH—C(O)—$CH_2$—O—$[(CH_2)_2—O]_n$—$(CH_2)_p$—C(O)-J and —$CH_2$—O—$[(CH_2)_2—O]_n$—$(CH_2)_m$—NH—$(CH_2)_p$—C(O)-J, with m being an integer from 0 to 10; n being an integer from 0 to 15; and p being an integer from 0 to 3.

Optionally, f is 1 and L-J is selected in the group consisting of —C(O)—$(CH_2)_5$—NH—$[(CH_2)_2—O]_{3-13}$—$CH_2$—C(O)-J, —C(O)—$(CH_2)_5$—NH—C(O)—$[(CH_2)_2—O]_{3-13}$—$CH_2$-J, C(O)—$(CH_2)_5$—NH—C(O)—$CH_2$—O—$[(CH_2)_2—O]_{3-13}$—$CH_2$-J, —C(O)—$(CH_2)_5$—NH—C(O)—$[(CH_2)_2—O]_{3-13}$—$CH_2$—C(O)-J and —C(O)—$(CH_2)_5$—NH—C(O)—$CH_2$—O—$[(CH_2)_2—O]_{3-13}$—$CH_2$—C(O)-J, —C(O)—$(CH_2)_5$—NH—C(O)-J or —$CH_2$—O—$[(CH_2)_2—O]_{3-13}$—$(CH_2)_{3-5}$—NH—$CH_2$—C(O)-J.

For instance, f can be 1 and L-J is selected from the group consisting of —C(O)—$(CH_2)_5$—NH—$[(CH_2)_2—O]_3$—$(CH_2)_2$—C(O)-J, —C(O)—$(CH_2)_5$—NH—C(O)—$[(CH_2)_2—O]_3$—$(CH_2)_3$-J, —C(O)—$(CH_2)_5$—NH—C(O)—$CH_2$—O—$[(CH_2)_2—O]_5$—$CH_2$—C(O)-J, —C(O)—$(CH_2)_5$—NH—C(O)—$CH_2$—O—$[(CH_2)_2—O]_9$—$CH_2$—C(O)-J, —C(O)—$(CH_2)_5$—NH—C(O)—$CH_2$—O—$[(CH_2)_2—O]_{13}$—$CH_2$—C(O)-J, —C(O)—$(CH_2)_5$—NH—C(O)-J or —$CH_2$—O—$[(CH_2)_2—O]_3$—$(CH_2)_3$—NH—$CH_2$—C(O)-J.

In a very particular aspect, f is 1 and L-J is —C(O)—$(CH_2)_m$—NH—$[(CH_2)_2—O]_n$—$(CH_2)_p$—C(O)-J with m being an integer from 0 to 10, preferably from 4 to 6, especially 5; n being an integer from 0 to 6; and p being an integer from 0 to 2. In a particular aspect, m is 5 and, n and p are 0. In another particular aspect, m is 5, n is 3 and p is 2.

In another specific aspect, the loop has the formula (I) In an aspect the loop is —O—P(S)OH—O—$\{[(CH_2)_2—O]_g—P(O)OH—O\}_r$—K—O—P(S)OH—O—$\{[(CH_2)_2—O]_h—P(X)OH—O—\}_s$, with X being O or S at each occurrence of —O—P(X)OH—O—, r being 1, g being 6, s being 0, and K being —$CH_2$—CH-($L_f$-J).

In a preferred object, the loop is —O—P(S)OH—O—$[(CH_2)_2—O]_6$—P(O)OH—O—K—(O—P(S)OH—O)—, K being —$CH_2$—CH($L_f$-J)-. In another preferred object, the loop is —O—P(S)OH—O—$[(CH_2)_2—O]_6$—P(S)OH—O—K—(O—P(S)OH—O)—, K being —$CH_2$—CH($L_f$-J)-. In a particular aspect, f is 1 and L-J is —$CH_2$—O—$[(CH_2)_2—O]_n$—$(CH_2)_m$—NH—$(CH_2)_p$—C(O)-J, with m being 3; n being 3; and p being 0.

In a specific embodiment, the linker between the molecule facilitating endocytosis and the loop comprises J being C(O)—NH—$(CH_2)_3$—$(CH_2—CH_2—O)_n$ or NH—C(O)—$(CH_2)_3$—$(CH_2—CH_2—O)_n$, wherein n is an integer from 1 to 10, preferably n being selected from the group consisting of 3, 4, 5 and 6. In a very particular embodiment, the linker is CO—NH—$(CH_2)_3$—$(CH_2—CH_2—O)_4$ (carboxamido tetraethylene glycol or also 13—O—[1-propyl-3-N-carbamoylcholesteryl]-tetraethyleneglycol radical).

In another specific embodiment, the linker between the molecule facilitating endocytosis and the loop molecule is dialkyl-disulfide {e.g., $(CH_2)_p$—S—S—$(CH_2)_q$ with p and q being integer from 1 to 10, preferably from 3 to 8, for instance 6}.

In a second aspect of the disclosure, the loop has a structure according to formula (II):

$$—O—P(X)OH—O—[(CH_2)_d—C(O)—NH]_b—CHR—[C(O)—NH—(CH_2)_e]_c—O—P(X)OH—O— \quad (II)$$

with X being O or S;

b and c being independently an integer from 0 to 4, and the sum b+c is from 3 to 7;

d and e being independently an integer from 1 to 3, preferably from 1 to 2;

with R being —$(CH_2)_{1-5}$—C(O)—NH-$L_f$-J or —$(CH_2)_{1-5}$—NH—C(O)-$L_f$-J, and with L being a linker, preferably a linear alkylene or an oligoethylene glycol, f being an integer being 0 or 1, and J being a molecule facilitating the endocytosis.

If b and/or c are 2 or more, d and e can be different in each occurrence of $[(CH_2)_d$—C(O)—NH] or —[C(O)—NH—$(CH_2)_e]$.

In one aspect, when d and e are 2, the sum b+c is from 3 to 5, in particular 4. For instance, b can be 0 and c is from 3 to 5; b can be 1 and c is from 2 to 4; b can be 2 and c is from 1 to 3; or b can be from 3 to 5 and c is 0.

In one aspect, when d and e are 1, the sum b+c is from 4 to 7, in particular 5 or 6. For instance, b can be 0 and c is from 3 to 6; b can be 1 and c is from 2 to 5; b can be 2 and c is from 1 to 4; or b can be from 3 to 6 and c is 0.

In one aspect, b, c, d and e are selected so as the loop comprises a chain from 10 to 100 atoms, preferably from 15 to 25 atoms.

In a non-exhaustive list of examples, the loop could be one of the following:

—O—P(X)OH—O—$(CH_2)_2$—C(O)—NH—$(CH_2)_2$—C(O)—NH—CHR—C(O)—NH—$(CH_2)_2$—C(O)—NH—$(CH_2)_2$—O—P(X)OH—O—;

—O—P(X)OH—O—$(CH_2)_2$—C(O)—NH—CHR—C(O)—NH—$(CH_2)_2$—C(O)—NH—$(CH_2)_2$—C(O)—NH—$(CH_2)_2$—O—P(X)OH—O—;

—O—P(X)OH—O—CHR—C(O)—NH—$(CH_2)_2$—C(O)—NH—$(CH_2)_2$—C(O)—NH—$(CH_2)_2$—C(O)—NH—$(CH_2)_2$—O—P(X)OH—O—;

—O—P(X)OH—O—$(CH_2)_2$—C(O)—NH—$(CH_2)_2$—C(O)—NH—$(CH_2)_2$—C(O)—NH—CHR—C(O)—NH—$(CH_2)_2$—O—P(X)OH—O—;

—O—P(X)OH—O—$(CH_2)_2$—C(O)—NH—$(CH_2)_2$—C(O)—NH—$(CH_2)_2$—C(O)—NH—$(CH_2)_2$—C(O)—NH—CHR—O—P(X)OH—O—;

—O—P(X)OH—O—$(CH_2)_2$—C(O)—NH—$(CH_2)$—C(O)—NH—CHR—C(O)—NH—$(CH_2)$—C(O)—NH—$(CH_2)_2$—O—P(X)OH—O—;

—O—P(X)OH—O—$(CH_2)$—C(O)—NH—$(CH_2)_2$—C(O)—NH—CHR—C(O)—NH—$(CH_2)_2$—C(O)—NH—$(CH_2)$—O—P(X)OH—O—; or

—O—P(X)OH—O—$(CH_2)$—C(O)—NH—$(CH_2)$—C(O)—NH—CHR—C(O)—NH—$(CH_2)$—C(O)—NH—$(CH_2)$—O—P(X)OH—O—.

In a particular aspect, the loop can be the following:

—O—P(X)OH—O—$(CH_2)_2$—C(O)—NH—$(CH_2)_2$—C(O)—NH—CHR—C(O)—NH—$(CH_2)_2$—C(O)—NH—$(CH_2)_2$—O—P(X)OH—O—.

with R being -$L_f$-J; and with L being a linker, preferably a linear alkylene and/or an oligoethylene glycol optionally interrupted by one or several groups selected from amino, amide, and oxo, and f being an integer being 0 or 1.

Preferably, X is S.

L can be —$(CH_2)_{1-5}$—C(O)-J, preferably —$CH_2$—C(O)-J or —$(CH_2)_2$—C(O)-J.

Alternatively, L-J can be —$(CH_2)_4$—NH—[$(CH_2)_2$—O]$_n$—$(CH_2)_p$—C(O)-J with n being an integer from 0 to 6; and p being an integer from 0 to 2. In a particular aspect, n is 3 and p is 2.

Molecules Facilitating Endocytosis

The nucleic acid molecules of the present invention are optionally conjugated to a molecule facilitating endocytosis, referred as J in the above formulae. Therefore, in a first aspect, J is a molecule facilitating endocytosis. In an alternative aspect, J is a hydrogen.

The molecules facilitating endocytosis may be lipophilic molecules such as cholesterol, single or double chain fatty acids, or ligands which target cell receptors enabling receptor mediated endocytosis, such as folic acid and folate derivatives or transferrin (Goldstein et al. Ann. Rev. Cell Biol. 1985 1:1-39; Leamon & Lowe, Proc Natl Acad Sci USA. 1991, 88: 5572-5576.). Fatty acids may be saturated or unsaturated and be in $C_4$-$C_{28}$, preferably in $C_{14}$-$C_{22}$, still more preferably being in $C_{18}$ such as oleic acid or stearic acid. In particular, fatty acids may be octadecyl or dioleoyl. Fatty acids may be found as double chain form linked with an appropriate linker such as a glycerol, a phosphatidylcholine or ethanolamine and the like or linked together by the linkers used to attach on the conjugated nucleic acid molecule. As used herein, the term "folate" is meant to refer to folate and folate derivatives, including pteroic acid derivatives and analogs. The analogs and derivatives of folic acid suitable for use in the present invention include, but are not limited to, antifolates, dihydrofolates, tetrahydrofolates, folinic acid, pteropolyglutamic acid, 1-deaza, 3-deaza, 5-deaza, 8-deaza, 10-deaza, 1,5-deaza, 5,10-dideaza, 8,10-dideaza, and 5,8-dideaza folates, antifolates, and pteroic acid derivatives. Additional folate analogs are described in US2004/242582.

Accordingly, the molecule facilitating endocytosis may be selected from the group consisting of single or double chain fatty acids, folates and cholesterol. More preferably, the molecule facilitating endocytosis is selected from the group consisting of dioleoyl, octadecyl, folic acid, and cholesterol. In a most preferred embodiment, the molecule facilitating endocytosis is a cholesterol.

Accordingly, in one preferred embodiment, the conjugated nucleic acid molecule has the following formula:

SEQ IS NOs: 1 and 2

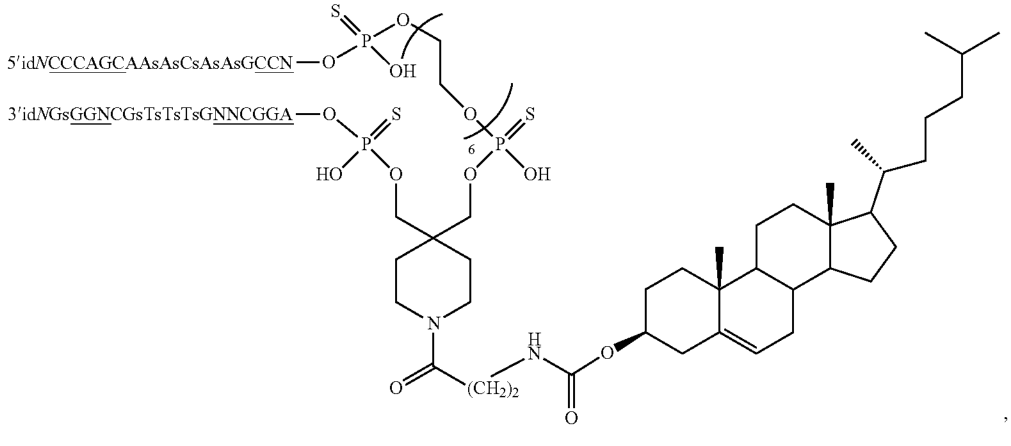

, respectively, wherein each occurrence of N is T or U, wherein idN is an inverted nucleotide and is present or absent, wherein internucleotide linkages "s" refer to phosphorothioate internucleotide linkages; and wherein the underlined nucleotides are 2'-modified nucleotides;

or the pharmaceutically acceptable salts thereof.

Preferably, the molecule has 1) at least one N which is U, and/or 2) at least one idN which is present. Alternatively, the molecule is not OX413.

In a particular aspect, when idN is present, it is preferably an inverted thymidine idT.

In a very particular aspect, the conjugated nucleic acid molecule is:

SEQ IS NOs: 3 and 4

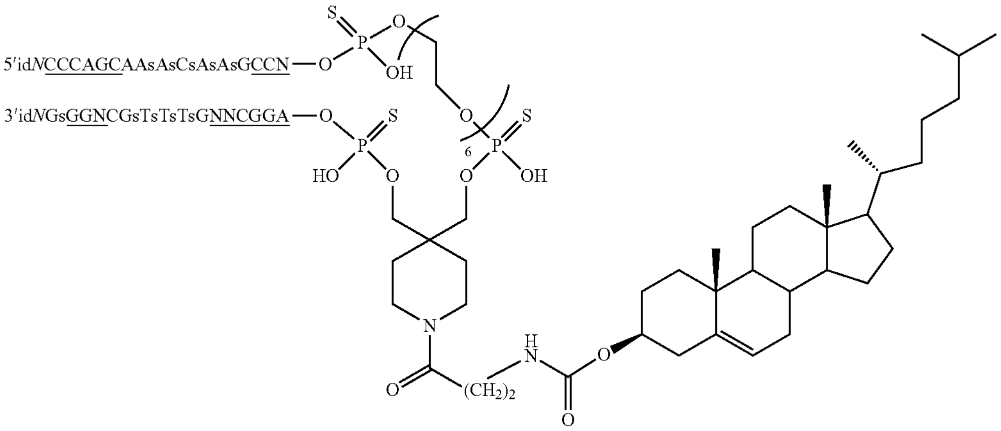

, respectively, wherein idN is an inverted nucleotide and is present or absent, wherein Nis T, wherein internucleotide linkages "s" refer to phosphorothioate internucleotide linkages; and wherein the underlined nucleotides are 2-modified nucleotides, preferably 2'-deoxy-2'-fluoroarabinonucleotides (F-ANA) or 2'O-Methyl nucleotides (2'-OMe), or the pharmaceutically acceptable salts thereof.

Preferably, idN is present in the molecule. Alternatively, the molecule is not OX413.

In a particular aspect, when idN is present, it is preferably an inverted thymidine idT.

In another particular aspect, the conjugated nucleic acid molecule is:

SEQ ID NOs: 5 and 6

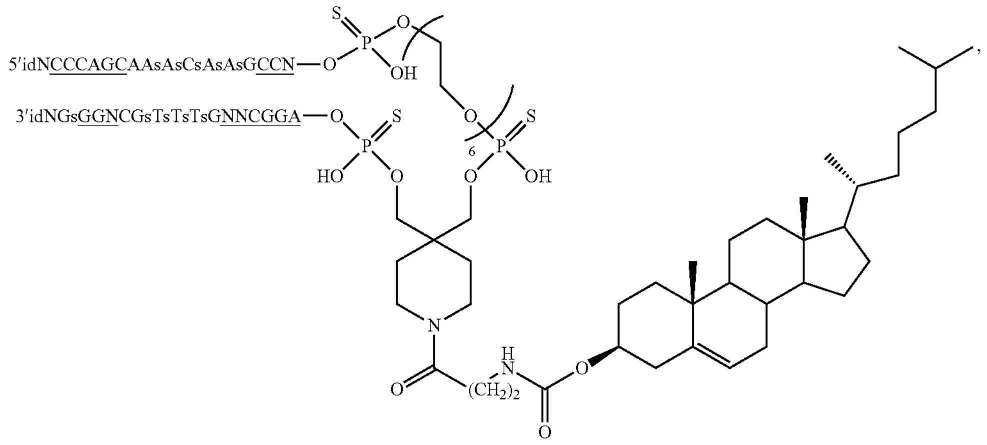

respectively, wherein idN is an inverted nucleotide and is present or absent, wherein N is U, wherein internucleotide linkages “s” refer to phosphorothioate internucleotide linkages; and wherein the underlined nucleotides are 2'-modified nucleotides, preferably 2'-deoxy-2'-fluoroarabinonucleotides (F-ANA) or 2'O-Methyl nucleotides (2'-OMe), or the pharmaceutically acceptable salts thereof.

In a particular aspect, when idN is present, it is preferably an inverted thymidine idT.

When the idN are absent, N is T and the underlined 2'-modified nucleotides are 2'-deoxy-2'-fluoroarabinonucleotides (F-ANA), the molecule is OX413:

SEQ ID NOs: 13 and 14

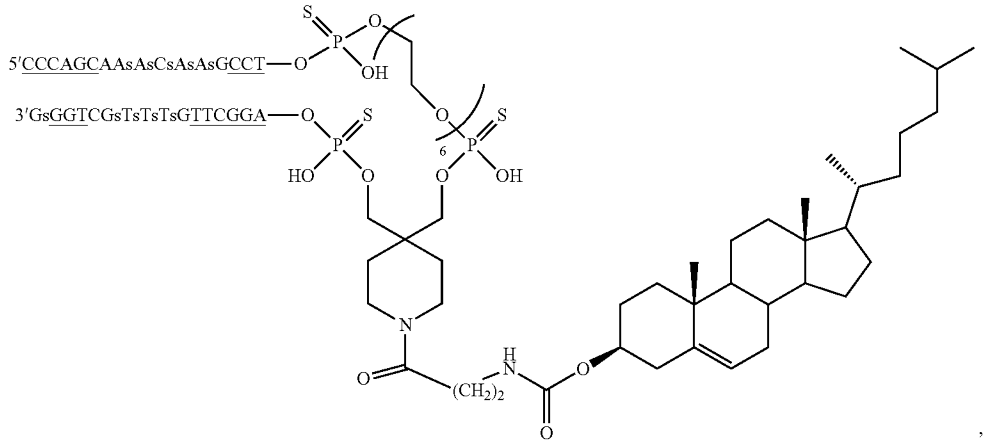

, respectively.

In one aspect, when the idN is absent, N is U and the underlined 2'-modified nucleotides are 2'-O-methyl nucleotides (2'-OMe), the molecule is OX416:

SEQ ID NOs: 7 and 8

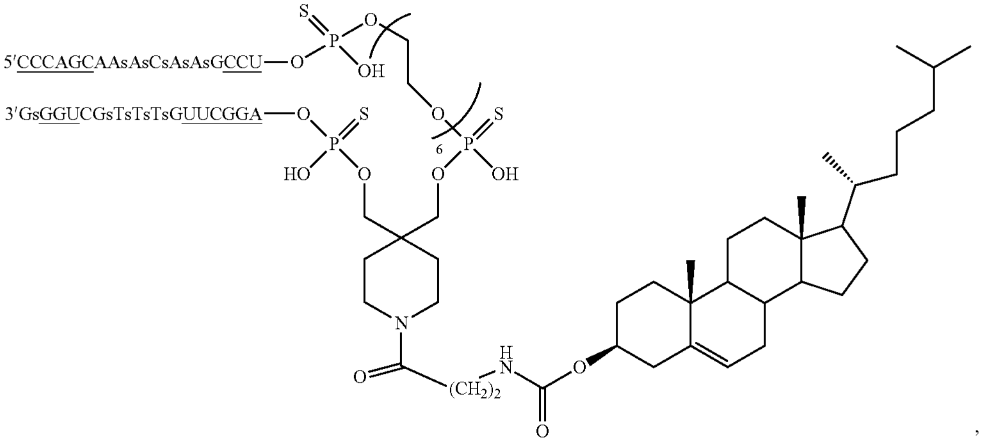

, respectively,

In another aspect, the idN are present and when idN is idT and present at the 5' end and at the 3' end, N is T, and the underlined 2'-modified nucleotides are 2'-deoxy-2'-fluoroarabinonucleotides (F-ANA), the molecule is OX421:

SEQ ID NOs: 9 and 10

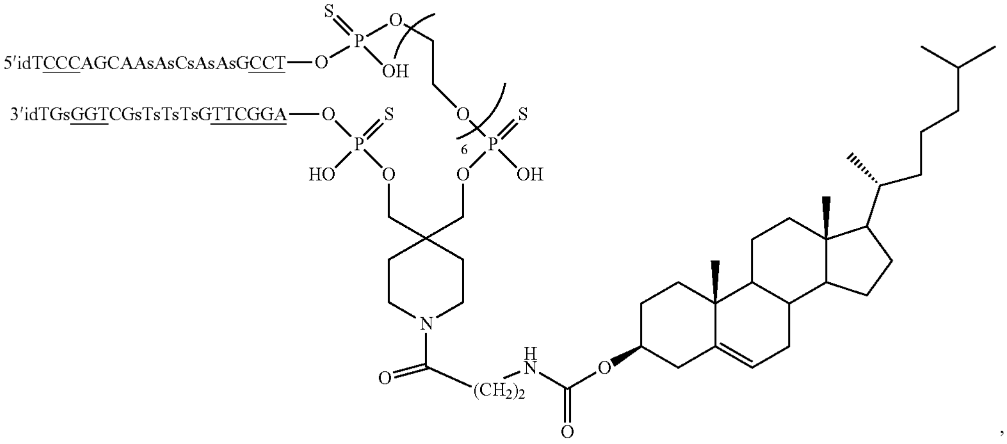

, respectively, when idN is idT and present at the 5' end and at the 3' end, N is U, and the underlined 2'-modified nucleotides are 2'-O-methyl nucleotides (2'-OMe), the molecule is OX422:

SEQ ID NOs: 11 and 12

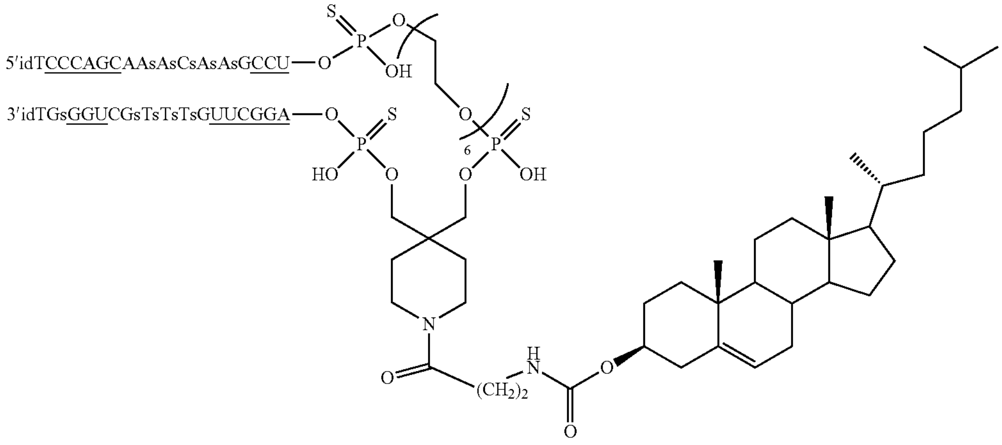

, respectively.

In another particular aspect, the conjugated nucleic acid molecule is:

SEQ ID NOs: 1 and 2

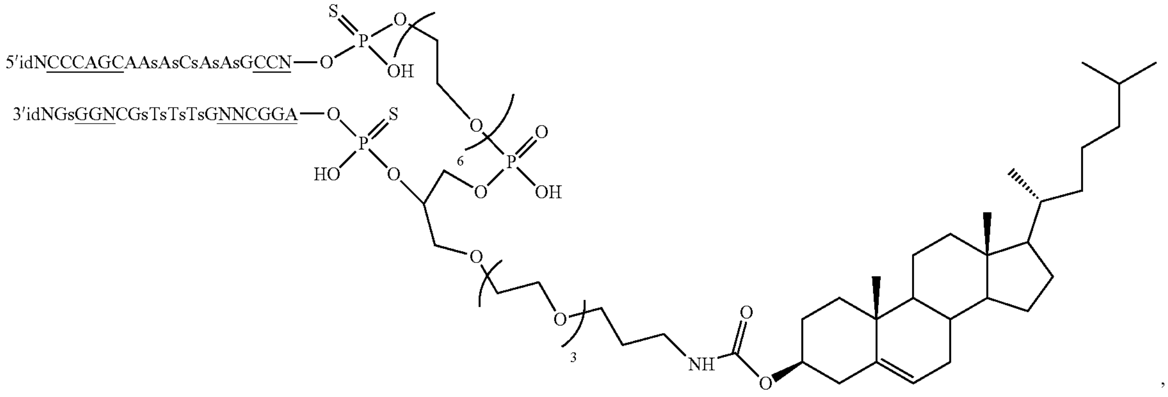

, respectively, wherein each occurrence of N is T or U, wherein idN is an inverted nucleotide and is present or absent, wherein internucleotide linkages "s" refer to phosphorothioate internucleotide linkages; and wherein the underlined nucleotides are 2'-modified nucleotides, preferably 2'-deoxy-2'-fluoroarabinonucleotides (F-ANA) or 2'O-Methyl nucleotides (2'-OMe), or the pharmaceutically acceptable salts thereof.

In a particular aspect, when idN is present, it is preferably an inverted thymidine idT.

In a very particular aspect, the conjugated nucleic acid molecule is:

SEQ ID NOs: 3 and 4

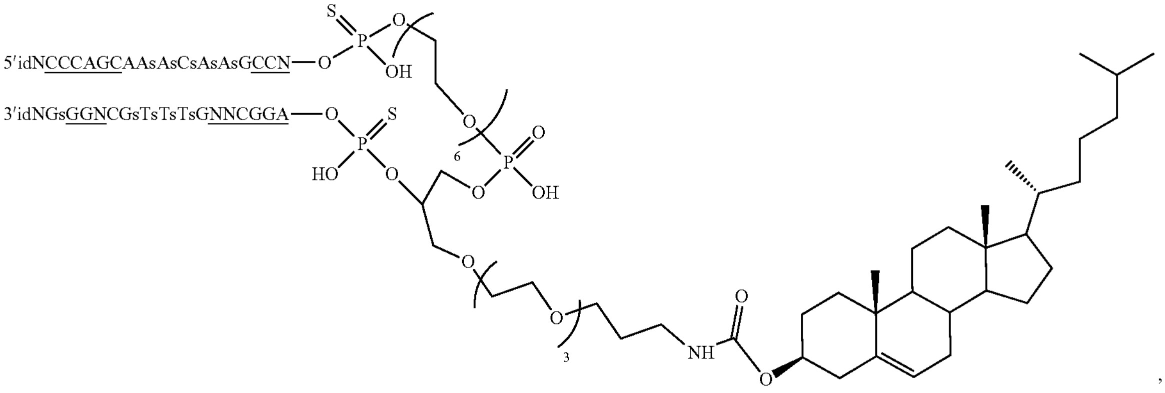

, respectively, wherein idN is an inverted nucleotide and is present or absent, wherein N is T, wherein internucleotide linkages "s" refer to phosphorothioate internucleotide linkages; and wherein the underlined nucleotides are 2'-modified nucleotides, preferably 2'-deoxy-2'-fluoroarabinonucleotides (F-ANA) or 2'O-Methyl nucleotides (2'-OMe), or the pharmaceutically acceptable salts thereof.

In a particular aspect, when idN is present, it is preferably an inverted thymidine idT.

In a very particular aspect, the conjugated nucleic acid molecule is:

SEQ ID NOs: 5 and 6

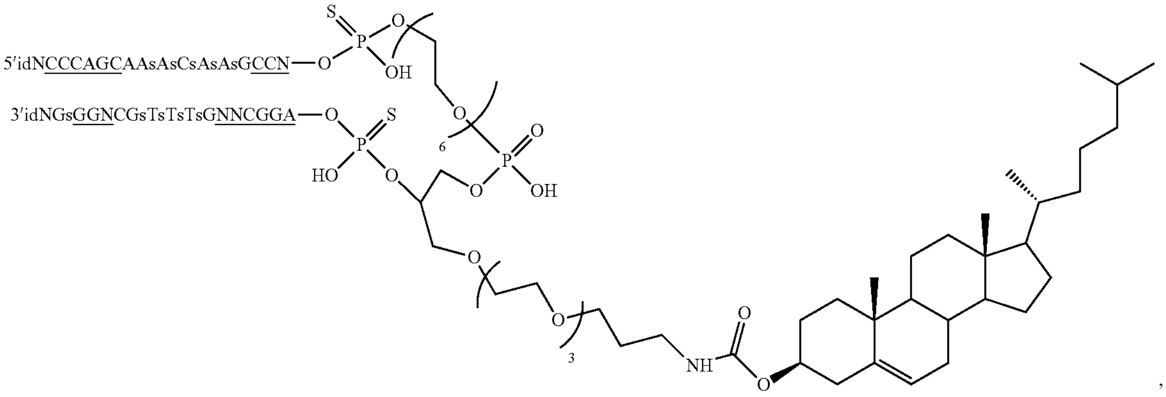

, respectively, wherein idN is an inverted nucleotide and is present or absent, wherein N is U, wherein internucleotide linkages "s" refer to phosphorothioate internucleotide linkages; and wherein the underlined nucleotides are 2'-modified nucleotides, preferably 2'-deoxy-2'-fluoroarabinonucleotides (F-ANA) or 2'O-Methyl nucleotides (2'-OMe), or the pharmaceutically acceptable salts thereof.

In a particular aspect, when idN is present, it is preferably an inverted thymidine idT.

In a preferred aspect, the idN are absent, N is U and the underlined 2'-modified nucleotides are 2'-O-methyl nucleotides (2'-OMe), and the molecule is OX423:

SEQ ID NOs: 7 and 8

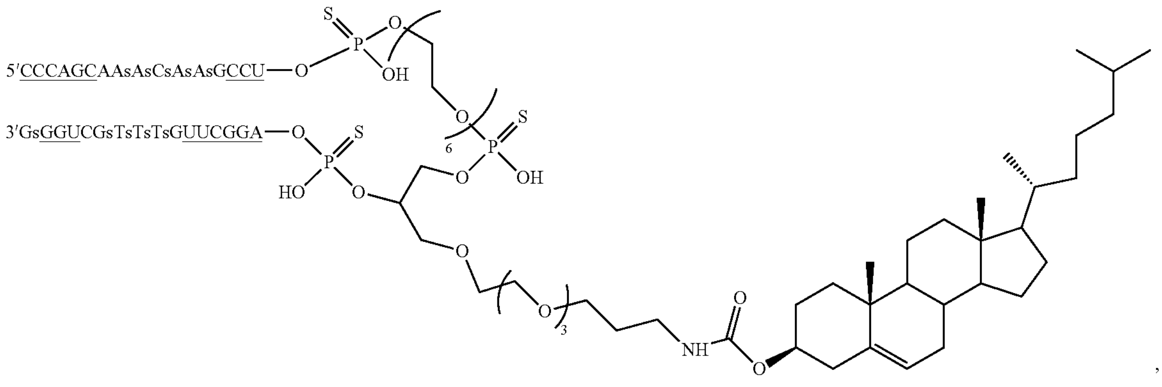

, respectively.

In another particular aspect, the conjugated nucleic acid molecule is:

SEQ ID NOs: 1 and 2

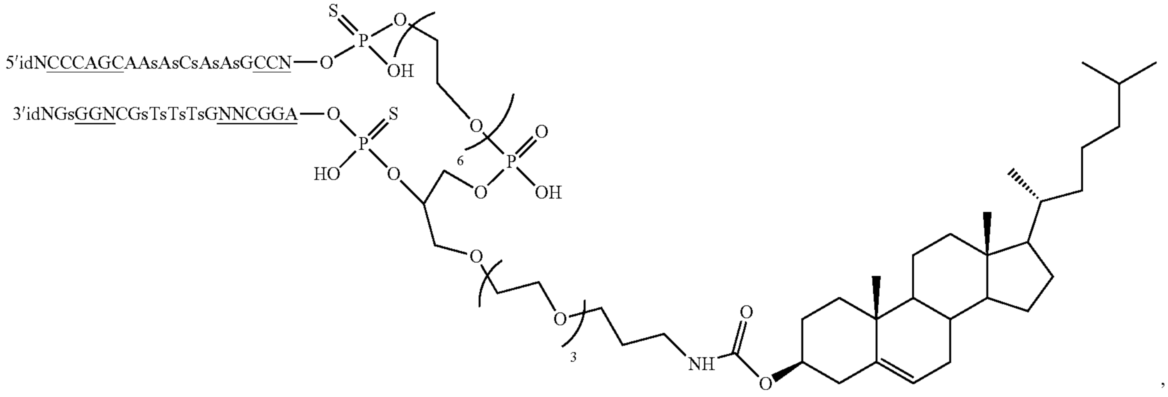

, respectively, wherein each occurrence of N is independently T or U, wherein idN is an inverted nucleotide and is present at the 5' end and/or at the 3' end, wherein internucleotide linkages "s" refer to phosphorothioate internucleotide linkages; and wherein the underlined nucleotides are 2'-modified nucleotides, preferably 2'-deoxy-2'-fluoroarabinonucleotides (F-ANA) or 2'O-Methyl nucleotides (2'-OMe), or the pharmaceutically acceptable salts thereof.

In a particular aspect, when idN is present, it is preferably an inverted thymidine idT.

In a very particular aspect, the conjugated nucleic acid molecule is:

SEQ ID NOs: 3 and 4

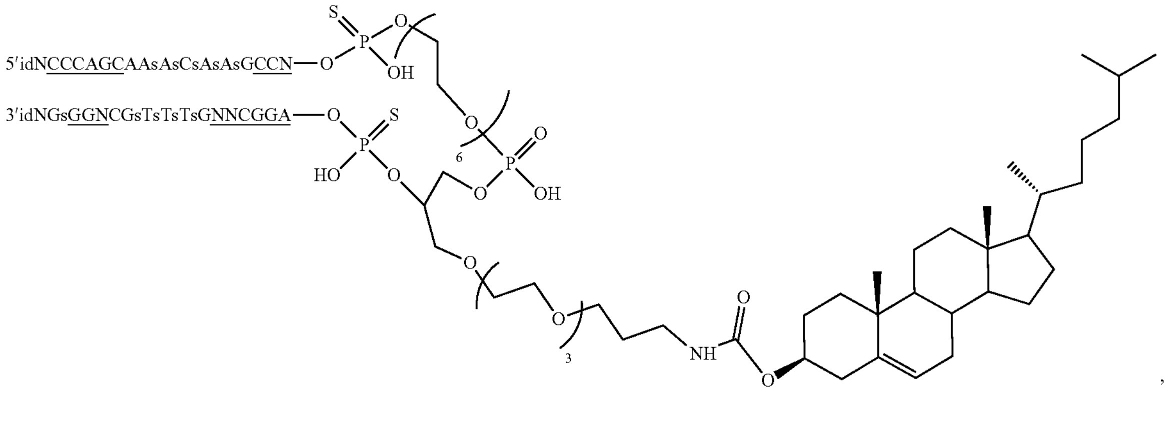

, respectively, wherein idN is an inverted nucleotide and is present at the 5' end and/or at the 3' end, wherein N is T, wherein internucleotide linkages "s" refer to phosphorothioate internucleotide linkages; and wherein the underlined nucleotides are 2'-modified nucleotides, preferably 2'-deoxy-2'-fluoroarabinonucleotides (F-ANA) or 2'O-Methyl nucleotides (2'-OMe), or the pharmaceutically acceptable salts thereof.

In a particular aspect, when idN is present, it is preferably an inverted thymidine idT.

In another particular aspect, the conjugated nucleic acid molecule is:

SEQ ID NOs: 5 and 6

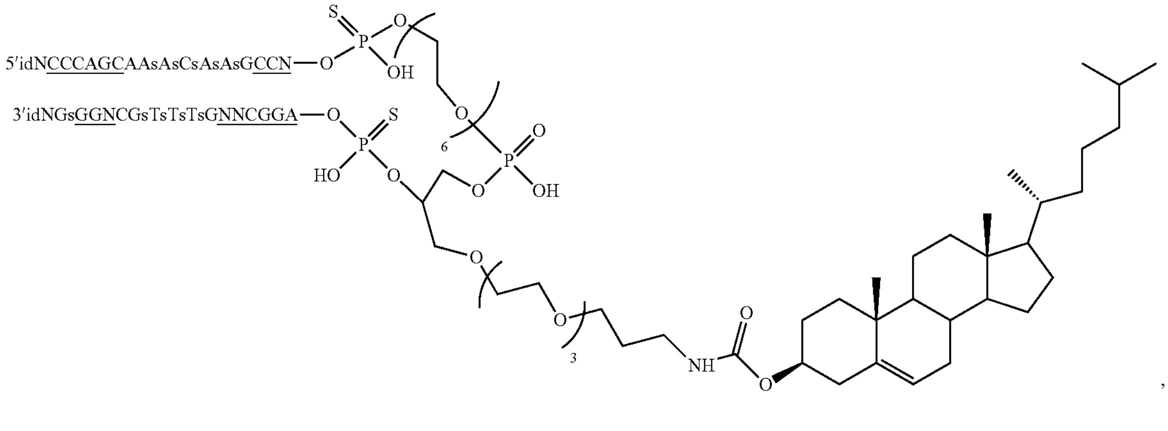

, respectively, wherein idN is an inverted nucleotide and is present at the 5' end and/or at the 3' end wherein N is U, wherein internucleotide linkages "s" refer to phosphorothioate internucleotide linkages; and wherein the underlined nucleotides are 2'-modified nucleotides, preferably 2'-deoxy-2'-fluoroarabinonucleotides (F-ANA) or 2'O-Methyl nucleotides (2'-OMe), or the pharmaceutically acceptable salts thereof.

In a particular aspect, when idN is present, it is preferably an inverted thymidine idT.

In a preferred aspect, the idN are absent, N is U and the underlined 2'-modified nucleotides are 2'-O-methyl nucleotides (2'-OMe), and the molecule is OX424:

SEQ ID NOs: 7 and 8

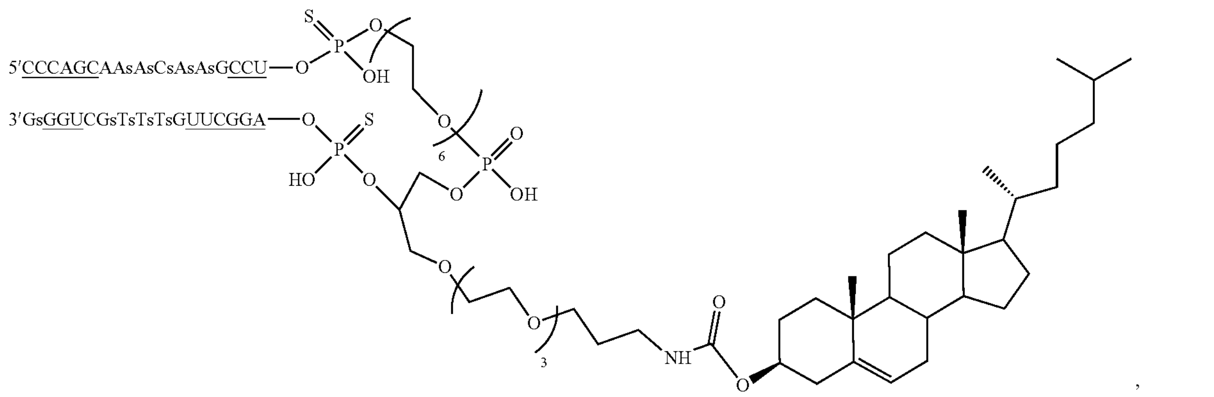

, respectively.

In a very particular aspect, the conjugated nucleic acid molecule is OX425:

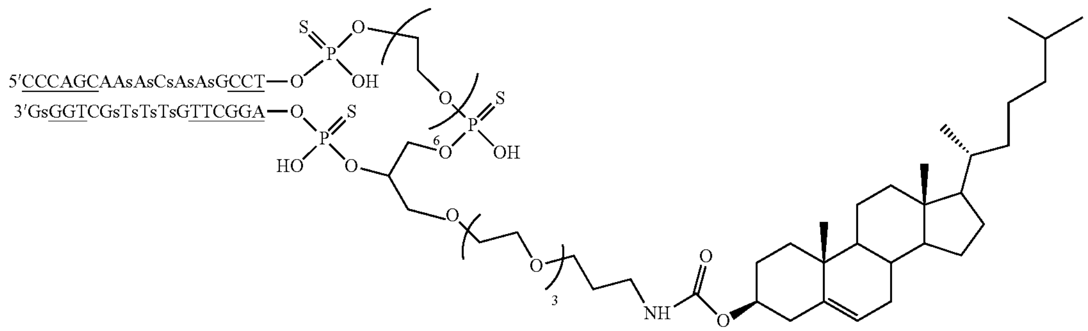

SEQ ID NOs: 19 and 20, respectively, wherein internucleotide linkages "s" refer to phosphorothioate internucleotide linkages; and wherein the underlined 2'-modified nucleotides are 2'-deoxy-2'-fluoroarabinonucleotides (FANA).

Alternatively, the molecule facilitating endocytosis may also be tocopherol, sugar such as galactose and mannose and their oligosaccharide, peptide such as RGD and bombesin, and proteins such as integrin.

Therapeutic Uses of the Nucleic Acid Molecules

The conjugated nucleic acid molecules according to the present invention are able to active PARP. They lead to an increase of micronuclei and cytotoxicity in cancer cells. They show specificity toward cancer cells which may preclude or limit side effects. In addition, the specific increase of micronuclei in cancer cells leads to an early activation of the STING pathway.

Accordingly, the conjugated nucleic acid molecules according to the present invention can be used as a drug, especially for the treatment of cancer.

Therefore, the present invention relates to a conjugated nucleic acid molecule according to the present invention for use as a drug. It further relates to a pharmaceutical composition comprising a conjugated nucleic acid molecule according to the present invention, especially for use for the treatment of cancer. The present invention further relates to a method for treating a cancer in a subject in need thereof comprising administering an effective amount of a conjugated nucleic acid molecule according to the present invention or a pharmaceutical composition or veterinary composition according to the present invention.

The pharmaceutical compositions contemplated herein may include a pharmaceutically acceptable carrier in addition to the active ingredient(s). The term "pharmaceutically acceptable carrier" is meant to encompass any carrier (e.g., support, substance, solvent, etc.) which does not interfere with effectiveness of the biological activity of the active ingredient(s) and that is not toxic to the host to which it is administered. For example, for parental administration, the active compounds(s) may be formulated in a unit dosage form for injection in vehicles such as saline, dextrose solution, serum albumin and Ringer's solution.

The pharmaceutical composition can be formulated as solutions in pharmaceutically compatible solvents or as emulsions, suspensions or dispersions in suitable pharmaceutical solvents or vehicle, or as pills, tablets or capsules that contain solid vehicles in a way known in the art. Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion. Formulations suitable for parental administration conveniently comprise a sterile oily or aqueous preparation of the active ingredient which is preferably isotonic with the blood of the recipient. Every such formulation can also contain other pharmaceutically compatible and nontoxic auxiliary agents, such as, e.g. stabilizers, antioxidants, binders, dyes, emulsifiers or flavouring substances. The formulations of the present invention comprise an active ingredient in association with a pharmaceutically acceptable carrier therefore and optionally other therapeutic ingredients. The carrier must be “acceptable” in the sense of being compatible with the other ingredients of the formulations and not deleterious to the recipient thereof. The pharmaceutical compositions are advantageously applied by injection or intravenous infusion of suitable sterile solutions or as oral dosage by the digestive tract. Methods for the safe and effective administration of most of these chemotherapeutic agents are known to those skilled in the art. In addition, their administration is described in the standard literature.

The pharmaceutical compositions and the products, kits or combined preparation described in the invention can be used for treating cancer in a subject.

The terms “cancer” and “cancerous” refer to or describe the physiological condition in mammals that is typically characterized by unregulated cell growth. Examples of cancer include, but are not limited to, solid tumors and hematological cancers, including carcinoma, lymphoma, blastoma (including medulloblastoma and retinoblastoma), sarcoma (including liposarcoma and synovial cell sarcoma), neuroendocrine tumors (including carcinoid tumors, gastrinoma, and islet cell cancer), mesothelioma, schwannoma (including acoustic neuroma), meningioma, adenocarcinoma, melanoma, and leukemia or lymphoid malignancies. More particular examples of such cancers include squamous cell cancer (e.g. epithelial squamous cell cancer), lung cancer including small-cell lung cancer, extensive-stage small cell lung cancer (ES-SCLC), non-small cell lung cancer (NSCLC), adenocarcinoma of the lung and squamous carcinoma of the lung, cancer of the peritoneum, hepatocellular cancer, gastric cancer including gastrointestinal cancer, pancreatic cancer, glioblastoma, neuroblastoma, cervical cancer, ovarian cancer, liver cancer, bladder cancer, urinary tract cancer, hepatoma cancer, endometrium cancer, breast cancer, colon cancer, rectal cancer, colorectal cancer, endometrial or uterine carcinoma, salivary gland carcinoma, kidney or renal cancer, prostate cancer, vulval cancer, thyroid cancer, renal cell carcinoma (RCC), hepatic carcinoma, anal carcinoma, penile carcinoma, testicular cancer, esophageal cancer, tumors of the biliary tract, as well as head and neck cancer. Additional cancer indications are disclosed herein.

In a particular aspect, the cancer is a homologous recombination deficient tumor. Alternatively, the cancer is a homologous recombination proficient tumor.

In a particular embodiment, “cancer” refers to tumor cells carrying $NAD^+$ depletion, for instance selected from ERCC1 or ATM deficiency or cancer cells carrying IDHs mutations.

In very particular embodiment, a clinical stratification or a selection of better responders is possible for patients with tumors showing deficiencies in the $NAD^+$ synthesis, in particular for patients with tumors carrying $NAD^+$ depletion.

Determining the optimal dosage will generally involve the balancing of the level of therapeutic benefit against any risk or deleterious side effects of the treatments of the present invention. The selected dosage level will depend on a variety of factors including, but not limited to, the activity of the conjugated nucleic acid molecule, the route of administration, the time of administration, the rate of excretion of the compound, the duration of the treatment, other drugs, compounds, and/or materials used in combination, and the age, sex, weight, condition, general health, and prior medical history of the patient. The amount of conjugated nucleic acid molecule and route of administration will ultimately be at the discretion of the physician, although generally the dosage will be to achieve local concentrations at the site of action which achieve the desired effect.

The administration route for the conjugated nucleic acid molecule as disclosed herein may be oral, parental, intravenous, intratumoral, subcutaneous, intracranial, intra-arterial, topical, rectal, transdermal, intradermal, nasal, intramuscular, intraperitoneal, intraosseous, and the like. In a preferred embodiment, the conjugated nucleic acid molecules are to be administered or injected near the tumoral site(s) to be treated.

For instance, the efficient amount of the conjugated nucleic acid molecules be from 0.01 to 1000 mg, for instance preferably from 0.1 to 100 mg. Of course, the dosage and the regimen can be adapted by the one skilled in the art in consideration of the chemotherapy and/or radiotherapy regimen.

The conjugated nucleic acid molecule according to the present invention can be used in combination with an additional therapeutic agent. The additional therapeutic agent can be for instance an immunomodulatory such as an immune checkpoint inhibitor, a T-cell-based cancer immunotherapy including adoptive cell transfer (ACT), genetically modified T-cells or engineered T-cells such as chimeric antigen receptor cells (CAR-T cells), a conventional chemotherapeutic, radiotherapeutic or anti-angiogenic agent, or targeted immunotoxin.

Combinations with Immunomodulators/Immune Checkpoint Inhibitors (IC)

The inventors demonstrated the high antitumor therapeutic potential of the combination of a conjugated nucleic acid molecule with an immunomodulator such as an immune checkpoint inhibitor (ICI), preferably an inhibitor of the PD-1/PD-L1 pathway, as suggested by the activation of the STING pathway and the increase of the PD-L1 expression. The invention thus provides combined therapies in which a conjugated nucleic acid molecule of the invention is administered to patients with, before, simultaneously, or after an immunomodulator such as an immune checkpoint inhibitor (ICI).

Accordingly, the present invention concerns a pharmaceutical composition comprising a conjugated nucleic acid molecule of the invention and an immunomodulator, more particularly for use in the treatment of cancer. The present invention also concerns a product comprising a conjugated nucleic acid molecule of the invention and an immunomodulator as a combined preparation for simultaneous, separate or sequential use, more particularly for use in the treatment of cancer. In a preferred embodiment, the immunomodulator is an inhibitor of the PD-1/PD-L1 pathway.

The invention also provides a method of treating cancer by administering to a patient in need thereof a conjugated nucleic acid molecule of the present invention in combination with one or more immunomodulators (e.g., one or more of an activator of a costimulatory molecule or an inhibitor of an immune checkpoint molecule). In a preferred embodiment, the immunomodulator is an inhibitor of the PD-1/PD-L1 pathway.

Activator of a Costimulatory Molecule:

In certain embodiments, the immunomodulator is an activator of a costimulatory molecule. In one embodiment, the agonist of the costimulatory molecule is selected from an agonist (e.g., an agonistic antibody or antigen-binding fragment thereof, or a soluble fusion) of OX40, CD2, CD27, CDS, ICAM-1, LFA-1 (CD11a/CD18), ICOS (CD278), 4-1 BB (CD137), GITR, CD30, CD40, BAFFR, HVEM, CD7, LIGHT, NKG2C, SLAMF7, NKp80, CD160, B7-H3 or CD83 ligand.

Inhibitor of an Immune Checkpoint Molecule:

In certain embodiments, the immunomodulator is an inhibitor of an immune checkpoint molecule. In one embodiment, the immunomodulator is an inhibitor of PD-1, PD-L1, PD-L2, CTLA-4, TIM-3, LAG-3, NKG2D, NKG2L, KIR, VISTA, BTLA, TIGIT, LAIR1, CD160, 2B4 and/or TGFRbeta. In one embodiment, the inhibitor of an immune checkpoint molecule inhibits PD-1, PD-L1, LAG-3, TIM-3, TIGIT or CTLA-4, or any combination thereof. The term “inhibition” or “inhibitor” includes a reduction in a certain parameter, e.g., an activity, of a given molecule, e.g., an immune checkpoint inhibitor. For example, inhibition of an activity, e.g., a PD-1 or PD-L1 activity, of at least 5%, 10%, 20%, 30%, 40%, 50% or more is included by this term. Thus, inhibition need not be 100%.

Inhibition of an inhibitory molecule can be performed at the DNA, RNA or protein level. In some embodiments, an inhibitory nucleic acid (e.g., a dsRNA, siRNA or shRNA), can be used to inhibit expression of an inhibitory molecule. In other embodiments, the inhibitor of an inhibitory signal is a polypeptide e.g., a soluble ligand (e.g., PD-1 Ig or CTLA-4 Ig), or an antibody or antigen-binding fragment thereof, that binds to the inhibitory molecule; e.g., an antibody or fragment thereof (also referred to herein as “an antibody molecule”) that binds to PD-1, PD-L1, PD-L2, CTLA-4, TIM-3, LAG-3, NKG2D, NKG2L, KIR VISTA, BTLA, TIGIT, LAIR1, CD160, 2B4 and/or TGFR beta, or a combination thereof.

In one embodiment, the antibody molecule is a full antibody or fragment thereof (e.g., a Fab, F(ab')2, Fv, or a single chain Fv fragment (scFv)). In yet other embodiments, the antibody molecule has a heavy chain constant region (Fc) selected from, e.g., the heavy chain constant regions of IgG1, IgG2, IgG3, IgG4, IgM, IgAQ1, IgA2, IgD, and IgE; particularly, selected from, e.g., the heavy chain constant regions of IgG1, IgG2, IgG3, and IgG4, more particularly, the heavy chain constant region of IgG1 or IgG4 (e.g., human IgG1 or IgG4). In one embodiment, the heavy chain constant region is human IgG1 or human IgG4. In one embodiment, the constant region is altered, e.g., mutated, to modify the properties of the antibody molecule (e.g., to increase or decrease one or more of Fc receptor binding, antibody glycosylation, the number of cysteine residues, effector cell function, or complement function). In certain embodiments, the antibody molecule is in the form of a bispecific or multispecific antibody molecule.

PD-1 Inhibitors

In some embodiments, the conjugated nucleic acid molecule of the present invention is administered in combination with a PD-1 inhibitor. In some embodiments, the PD-1 inhibitor is selected from PDR001 (Novartis), Nivolumab (Bristol-Myers Squibb), Pembrolizumab (Merck & Co), Pidilizumab (CureTech), MEDI0680 (Medimmune), REGN2810 (Regeneron), TSR-042 (Tesaro), PF-06801591 (Pfizer), BGB-A317 (Beigene), BGB-108 (Beigene), INCSHR1210 (Incyte), AMP-224 (Amplimmune), IBI308 (Innovent and Eli Lilly), JS001, JTX-4014 (Jounce Therapeutics), PDR001 (Novartis) or MGA012 (Incyte and MacroGenics).

Exemplary PD-1 Inhibitors

In some embodiments, the anti-PD-1 antibody is Nivolumab (CAS Registry Number: 946414-94-4). Alternative names for Nivolumab include MDX-1106, MDX-1106-04, ONO-4538, BMS-936558 or OPDIVO®. Nivolumab is a fully human IgG4 monoclonal antibody which specifically blocks PD1. Nivolumab (clone 5C4) and other human monoclonal antibodies that specifically bind to PD1 are disclosed in U.S. Pat. No. 8,008,449 and PCT Publication No. WO 2006/121168, which are incorporated herein by reference in their entirety.

In other embodiments, the anti-PD-1 antibody is Pembrolizumab. Pembrolizumab (Trade name KEYTRUDA formerly Lambrolizumab, also known as Merck 3745, MK-3475 or SCH-900475) is a humanized IgG4 monoclonal antibody that binds to PD1. Pembrolizumab is disclosed, e.g., in Hamid, O. et al. (2013) New England Journal of Medicine 369 (2): 134-44, PCT Publication No. WO 2009/114335, and U.S. Pat. No. 8,354,509, which are incorporated herein by reference in their entirety.

In some embodiments, the anti-PD-1 antibody is Pidilizumab. Pidilizumab (CT-011; CureTech) is a humanized IgG1 k monoclonal antibody that binds to PD1. Pidilizumab and other humanized anti-PD-1 monoclonal antibodies are disclosed in PCT Publication No. WO 2009/101611, which are incorporated herein by reference in their entirety.

Other anti-PD1 antibodies are disclosed in U.S. Pat. No. 8,609,089, US Publication No. 2010028330, and/or US Publication No. 20120114649, which are incorporated herein by reference in their entirety. Other anti-PD1 antibodies include AMP514 (Amplimmune).

In one embodiment, the anti-PD-1 antibody molecule is MEDI0680 (MedImmune), also known as AMP-514. MEDI0680 and other anti-PD-1 antibodies are disclosed in U.S. Pat. No. 9,205,148 and WO 2012/145493, which are incorporated herein by reference in their entirety.

In one embodiment, the anti-PD-1 antibody molecule is REGN2810 (Regeneron), also known as Cemiplimab.

In one embodiment, the anti-PD-1 antibody molecule is PF-06801591 (Pfizer).

In one embodiment, the anti-PD-1 antibody molecule is BGB-A317 (Beigene) also known as BGB-108 or Tislelizumab.

In one embodiment, the anti-PD-1 antibody molecule is INCSHR1210 (Incyte), also known as INCSHR01210 or SHR-1210 or Camrelizumab.

In one embodiment, the anti-PD-1 antibody molecule is TSR-042 (Tesaro), also known as ANB011 or Dostarlimab.

In one embodiment, the anti-PD-1 antibody molecule is IBI308 (Innovent and Eli Lilly) also known as Sintilimab.

In one embodiment, the anti-PD-1 humanized IgG4 monoclonal antibody molecule is JS 001 also known as Toripalimab.

In one embodiment, the anti-PD-1 antibody molecule is JTX-4014 (Jounce Therapeutics).

In one embodiment, the anti-PD-1 monoclonal antibody molecule is PDR001 (Novartis), also known as Spartalizumab.

In one embodiment, the anti-PD-1 humanized IgG4 monoclonal antibody molecule MGA012 (Incyte and MacroGenics), also known as INCMGA00012 or Retifanlimab.

Further known anti-PD-1 antibodies include those described, e.g., in WO 2015/1 12800, WO 2016/092419, WO 2015/085847, WO 2014/179664, WO 2014/194302, WO 2014/209804, WO 2015/2001 19, U.S. Pat. Nos. 8,735, 553, 7,488,802, 8,927,697, 8,993,731, and 9,102,727, which are incorporated herein by reference in their entirety.

In one embodiment, the anti-PD-1 antibody is an antibody that competes for binding with, and/or binds to the same epitope on PD-1 as, one of the anti-PD-1 antibodies described herein.

In one embodiment, the PD-1 inhibitor is a peptide that inhibits the PD-1 signaling pathway, e.g., as described in U.S. Pat. No. 8,907,053, which is incorporated herein by reference in its entirety. In some embodiments, the PD-1 inhibitor is an immunoadhesin {e.g., an immunoadhesin comprising an extracellular or PD-1 binding portion of PD-L1 or PD-L2 fused to a constant region (e.g., an Fc region of an immunoglobulin sequence)}. In some embodiments, the PD-1 inhibitor is AMP-224 (B7-DCIg (Amplimmune), e.g., disclosed in WO 2010/027827 and WO 2011/066342, which are incorporated herein by reference in their entirety.

In a very particular embodiment, the conjugated nucleic acid molecule is selected from the group consisting of OX416, OX421, OX422, OX423, OX424 and OX425, more preferably OX425, and the additional therapeutic agent is an immune checkpoint inhibitor (ICI), preferably an inhibitor of the PD-1/PD-L1 pathway, more preferably an anti-PD-1 antibody such as PDR001 (Novartis), Nivolumab (Bristol-Myers Squibb), Pembrolizumab (Merck & Co), Pidilizumab (CureTech), MEDIO680 (Medimmune), REGN2810 (Regeneron), TSR-042 (Tesaro), PF-06801591 (Pfizer), BGB-A317 (Beigene), BGB-108 (Beigene), INCSHR1210 (Incyte), AMP-224 (Amplimmune), IBI308 (Innovent and Eli Lilly), JS001, JTX-4014 (Jounce Therapeutics), PDR001 (Novartis) or MGA012 (Incyte and MacroGenics).

PD-L1 Inhibitors

In certain embodiments, the inhibitor of an immune checkpoint molecule is an inhibitor of PD-L1. In some embodiments, the conjugated nucleic acid molecule of the present invention is administered in combination with a PD-L1 inhibitor. In some embodiments, the PD-L1 inhibitor is selected from FAZ053 (Novartis), Atezolizumab (Genentech/Roche), Avelumab (Merck Serono and Pfizer), Durvalumab (MedImmune/AstraZeneca), or BMS-936559 (Bristol-Myers Squibb).

Exemplary PD-L1 Inhibitors

In one embodiment, the PD-L1 inhibitor is an anti-PD-L1 antibody molecule. In one embodiment, the anti-PD-L1 antibody molecule is Avelumab (Merck Serono and Pfizer), also known as MSB0010718C. Avelumab and other anti-PD-L1 antibodies are disclosed in WO 2013/079174, which is incorporated herein by reference in its entirety.

In one embodiment, the anti-PD-L1 antibody molecule is Durvalumab (MedImmune/AstraZeneca), also known as MEDI4736. Durvalumab and other anti-PD-L1 antibodies are disclosed in U.S. Pat. No. 8,779,108, which is incorporated herein by reference in its entirety.

In one embodiment, the anti-PD-L1 antibody molecule is BMS-936559 (Bristol-Myers Squibb), also known as MDX-1105 or 12A4. BMS-936559 and other anti-PD-L1 antibodies are disclosed in U.S. Pat. No. 7,943,743 and WO 2015/081 158, which are incorporated herein by reference in their entirety.

Further known anti-PD-L1 antibodies include those described, e.g., in WO 2015/181342, WO 2014/100079, WO 2016/000619, WO 2014/022758, WO 2014/055897, WO 2015/061668, WO 2013/079174, WO 2012/145493, WO 2015/112805, WO 2015/109124, WO 2015/195163, U.S. Pat. Nos. 8,168,179, 8,552,154, 8,460,927, and 9,175,082, which are incorporated herein by reference in their entirety.

In one embodiment, the anti-PD-L1 antibody is an antibody that competes for binding with, and/or binds to the same epitope on PD-L1 as, one of the anti-PD-L1 antibodies described herein.

CTLA-4 (Cytotoxic T-Lymphocyte-Associated Protein 4) Inhibitors

In certain embodiments, the inhibitor of an immune checkpoint molecule is an inhibitor of CLTA-4. In some embodiments, the conjugated nucleic acid molecule of the present invention is administered in combination with a CLTA-4 inhibitor. In some embodiments, the CLTA-4 inhibitor is Ipilimumab.

Exemplary CTLA-4 Inhibitors

In one embodiment, the CLTA-4 inhibitor is an anti-CLTA-4 antibody molecule. In one embodiment, the anti-CLTA-4 antibody molecule is Ipilimumab (Bristol-Myers Squibb), also known as MDX-010.

LAG-3 Inhibitors

In certain embodiments, the inhibitor of an immune checkpoint molecule is an inhibitor of LAG-3. In some embodiments, the conjugated nucleic acid molecule of the present invention is administered in combination with a LAG-3 inhibitor. In some embodiments, the LAG-3 inhibitor is selected from LAG525 (Novartis), BMS-986016 (Bristol-Myers Squibb), TSR-033 (Tesaro), MK-4280 (Merck), REGN3767 (Regeneron), BI-754111 (Boehringer Ingelheim), SYM-022 (Symphogen), FS118 (F-star) or MGD013 (MacroGenics).

Exemplary LAG-3 Inhibitors

In one embodiment, the LAG-3 inhibitor is an anti-LAG-3 antibody molecule. In one embodiment, the LAG-3 inhibitor is BMS-986016 (Bristol-Myers Squibb), also known as BMS986016 or Relatlimab. BMS-986016 and other anti-LAG-3 antibodies are disclosed in WO 2015/116539 and U.S. Pat. No. 9,505,839, which are incorporated herein by reference in their entirety.

In one embodiment, the anti-LAG-3 antibody molecule is TSR-033 (Tesaro).

In one embodiment, the anti-LAG-3 antibody molecule is IMP731 or GSK2831781 (GSK and Prima BioMed). IMP731 and other anti-LAG-3 antibodies are disclosed in WO2008/132601 and U.S. Pat. No. 9,244,059, which are incorporated herein by reference in their entirety.

In one embodiment, the anti-LAG-3 antibody molecule is LAG525 (Novartis), also known as Ieramilimab.

In one embodiment, the anti-LAG-3 antibody molecule is MK-4280 (Merck), also known as Mavezelimab.

In one embodiment, the anti-LAG-3 antibody molecule is REGN3767 (Regeneron), also known as Fianlimab.

In one embodiment, the anti-LAG-3 antibody molecule is BI-754111 (Boehringer Ingelheim), also known as Miptenalimab.

In one embodiment, the anti-LAG-3 antibody molecule is SYM-022 (Symphogen).

In one embodiment, the anti-LAG-3 antibody molecule is FS118 (F-star).

In one embodiment, the anti-LAG-3 antibody molecule is MGD013 (MacroGenics), also known as Tebotelimab.

Further known anti-LAG-3 antibodies include those described, e.g., in WO 2008/132601, WO 2010/019570, WO 2014/140180, WO 2015/116539, WO 2015/200119, WO 2016/028672, U.S. Pat. Nos. 9,244,059, 9,505,839, which are incorporated herein by reference in their entirety.

TIM-3 Inhibitors

In certain embodiments, the inhibitor of an immune checkpoint molecule is an inhibitor of TIM-3. In some embodiments, the conjugated nucleic acid molecule of the present invention is administered in combination with a TIM-3 inhibitor. In some embodiments, the TIM-3 inhibitor is MGB453 (Novartis), TSR-022 (Tesaro), BMS-986258 (Bristol-Myers Squibb), SHR-1702, R07121661 (La Roche), MBG453 (Novartis), Sym023 (Symphogen), INCAGN2390 (Agenus) or LY3321367 (Eli Lilly).

Exemplary TIM-3 Inhibitors

In one embodiment, the anti-TIM-3 antibody molecule is TSR-022 (AnaptysBio/Tesaro).

In one embodiment, the anti-TIM-3 antibody is APE5137 or APE5121. APE5137, APE512, and other anti-TIM-3 antibodies are disclosed in WO 2016/161270, which is incorporated herein by reference in its entirety.

In one embodiment, the anti-TIM-3 antibody molecule is BMS-986258 (Bristol-Myers Squibb), also known as ONO 7807.

In one embodiment, the anti-TIM-3 antibody molecule is SHR-1702.

In one embodiment, the anti-TIM-3 antibody molecule is R07121661 (La Roche).

In one embodiment, the anti-TIM-3 antibody molecule is MBG453 (Novartis), also known as Sabatolimab.

In one embodiment, the anti-TIM-3 antibody molecule is Sym023 (Symphogen).

In one embodiment, the anti-TIM-3 antibody molecule is INCAGN2390 (Agenus).

In one embodiment, the anti-TIM-3 antibody molecule is LY3321367 (Eli Lilly).

Further known anti-TIM-3 antibodies include those described, e.g., in WO 2016/1 1 1947, WO 2016/071448, WO 2016/144803, U.S. Pat. Nos. 8,552,156, 8,841,418, and 9,163,087, which are incorporated herein by reference in their entirety.

NKG2D Inhibitors

In certain embodiments, the inhibitor of the NKG2D/NKG2DL pathway is an inhibitor of NKG2D. In some embodiments, the conjugated nucleic acid molecule of the present invention is administered in combination with a NKG2D inhibitor. In some embodiments, the NKG2D inhibitor is an anti-NKG2D antibody molecule such as the anti-NKG2D antibody NNC0142-0002 (also known as NN 8555, IPH2301 or JNJ-4500).

Exemplary NKG2D Inhibitors

In one embodiment, the anti-NKG2D antibody molecule is NNC0142-0002 (Novo Nordisk) as disclosed in WO 2009/077483 and U.S. Pat. No. 7,879,985, which are incorporated herein by reference in its entirety.

In another embodiment, the anti-NKG2D antibody molecule is JNJ-64304500 (Janssen) as disclosed in WO 2018/035330, which is incorporated herein by reference in its entirety.

In some embodiments, the anti-NKG2D antibodies are the human monoclonal antibodies 16F16, 16F31, MS, and 21F2 produced, isolated, and structurally and functionally characterized as described in U.S. Pat. No. 7,879,985. Further known anti-NKG2D antibodies include those described, e.g., in WO 2009/077483, WO 2010/017103, WO 2017/081190, WO 2018/035330 and WO 2018/148447, which are incorporated herein by reference in its entirety.

In some other embodiments, the NKG2D inhibitor is an immunoadhesin {e.g., an immunoadhesin comprising an extracellular or NKG2D binding portion of NKG2DL fused to a constant region (e.g., an Fc region of an immunoglobulin sequence as disclosed in WO 2010/080124, WO 2017/083545 and WO 2017/083612, which are incorporated herein by reference in its entirety).

NKG2DL Inhibitors

In some embodiments, the inhibitor of the NKG2D/NKG2DL pathway is an inhibitor of NKG2DL such as MICA, MICB, ULBP1, ULBP2, ULBP3, ULBP4, or a member of the RAET1 family. In some embodiments, the conjugated nucleic acid molecule of the present invention is administered in combination with a NKG2DL inhibitor. In some embodiments, the NKG2DL inhibitor is an anti-NKG2DL antibody molecule such as an anti-MICA/B antibody.

Exemplary MICA MICB Inhibitors

In one embodiment, the anti-MICA/B antibody molecule is IPH4301 (Innate Pharma) as disclosed in WO 2017/157895, which is incorporated herein by reference in its entirety.

Further known anti-MICA/B antibodies include those described, e.g., in WO 2014/140904 and WO 2018/073648, which are incorporated herein by reference in its entirety.

KIR Inhibitors

In certain embodiments, the inhibitor of an immune checkpoint molecule is an inhibitor of KIR. In some embodiments, the conjugated nucleic acid molecule of the present invention is administered in combination with a KIR inhibitor. In some embodiments, the KIR inhibitor is Lirilumab (also previously referred to as BMS-986015 or IPH2102).

Exemplary KIR Inhibitors

In one embodiment, the anti-KIR antibody molecule is Lirilumab (Innate Pharma/AstraZeneca) as disclosed in WO 2008/084106 and WO 2014/055648, which are incorporated herein by reference in their entirety.

Further known anti-KIR antibodies include those described, e.g., in WO 2005/003168, WO 2005/009465, WO 2006/072625, WO 2006/072626, WO 2007/042573, WO 2008/084106, WO 2010/065939, WO 2012/071411 and WO/2012/160448, which are incorporated herein by reference in their entirety.

TIGIT Inhibitors

In certain embodiments, the inhibitor of an immune checkpoint molecule is an inhibitor of TIGIT. In some embodiments, the conjugated nucleic acid molecule of the present invention is administered in combination with a TIGIT inhibitor. In some embodiments, the TIGIT inhibitor is MK-7684, Etigilimab, Tiragolumab or BMS-986207.

Exemplary TIGIT Inhibitors

In one embodiment, the TIGIT inhibitor is an anti-TIGIT antibody molecule. In one embodiment, the anti-TIGIT antibody molecule is selected from MK-7684 (Merck Sharp & Dohme), Etigilimab (OncoMed Pharmaceuticals, Mereo BioPharma), Tiragolumab (Genentech, Roche) or BMS-986207 (Bristol-Myers Squibb).

In one embodiment, the anti-TIGIT antibody molecule is MK-7684 (Merck Sharp & Dohme), also known as Vibostolimab.

In one embodiment, the anti-TIGIT antibody molecule is Etigilimab (OncoMed Pharmaceuticals, Mereo BioPharma).

In one embodiment, the anti-TIGIT antibody molecule is Tiragolumab (Genentech, Roche), also known as R07092284.

In one embodiment, the anti-TIGIT antibody molecule is BMS-986207 (Bristol-Myers Squibb).

Combinations with Conventional Chemotherapeutic, Radiotherapeutic, Anti-Angiogenic Agents The present invention also provides combined therapies in which a conjugated nucleic acid molecule of the invention is used simultaneously with, before, or after surgery or radiation treatment; or is administered to patients with, before, or after a conventional chemotherapeutic, radiotherapeutic or anti-angiogenic agent, or targeted immunotoxin.

The present invention also provides a method of treating cancer by administering to a patient in need thereof a conjugated nucleic acid molecule of the present invention in combination with a conventional chemotherapeutic, radiotherapeutic or anti-angiogenic agent, or targeted immunotoxin. The invention also concerns a pharmaceutical composition comprising a conjugated nucleic acid molecule of the invention and a conventional chemotherapeutic, radiotherapeutic or anti-angiogenic agent, or targeted immunotoxin, more particularly for use in the treatment of cancer. The invention also concerns a product comprising a conjugated nucleic acid molecule of the invention and a conventional chemotherapeutic, radiotherapeutic or anti-angiogenic agent, or targeted immunotoxin as a combined preparation for simultaneous, separate or sequential use, more particularly for use in the treatment of cancer.

Further aspects and advantages of the present invention will be disclosed in the following experimental section, which should be regarded as illustrative and not limiting the scope of the present application. A number of references are cited in the present specification; each of these cited references is incorporated herein by reference.

EXAMPLES

Example 1: Synthesis of the Nucleic Acid Molecules

Materials and Methods

OX401

In some examples, OX401 is used as control molecule. OX401 is a synthetic cholesterol-conjugate 16-base pair double helix DNA with a modified phosphodiester backbone, more particularly 3 phosphorothioate linkages on each strand.

The synthesis of OX401 was based on standard solid-phase DNA synthesis using solid phosphoramidite chemistry (dA(Bz); dC(Bz); dG(Ibu); dT (-)), HEG and Chol6 phosphoramidites.

SEQ ID NOs: 15 and 16

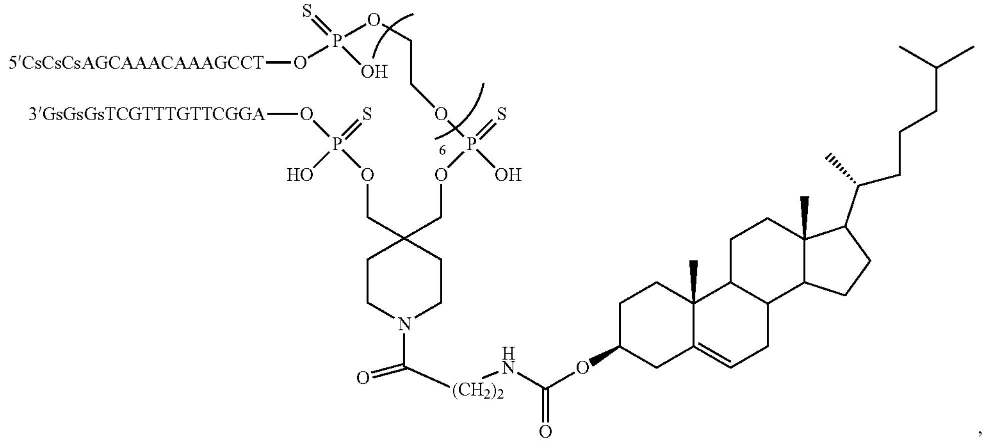

, respectively.

Detritylation steps were performed with 3% DCA in toluene, oxidations were performed with 50 mM iodine in pyridine/water 9/1 and sulfurizations were performed with 50 mM DDTT in pyridine/ACN 1/1. The capping was done with 20% NMI in ACN, together with 20% Ac2O in 2,6-lutidine/ACN (40/60). The cleavage and deprotection are performed with respectively 20% diethylamine in ACN to remove cyanoethyl protecting groups on phosphates/thiophosphates for 25 min and concentrated aqueous ammonia for 18 hours at 45° C.

The crude solution was loaded onto a preparative AEX-HPLC column (TSK gel SuperQ 5PW20). Purification was then performed eluting with a salt gradient of sodium bromide at pH 12 containing 20% acetonitrile by volume. After pooling of the fractions, desalting was performed by TFF on regenerated cellulose.

Purity of OX401: 91.8% by AEX-HPLC; Molecular weight by ESI-MS: 11046.5 Da. HEG phosphoramidite (Hexaethylene glycol phosphoramidite) (No CLP-9765, ChemGenes Corp)

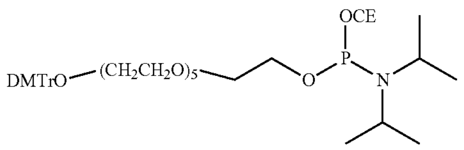

Chol6 phosphoramidite (No 51230, AM Chemicals)

Purity of OX423: 94.5% by AEX-HPLC; Molecular Weight by ESI-MS: 11601.9 Da.

OX425

The synthesis of OX425 was carried out by Axolabs (Germany) following conventional approaches in oligonucleotide synthesis. The manufacture of oligonucleotides consists of 5 steps—solid phase synthesis, cleavage and deprotection, bulk purification and mock pooling, ultrafiltration and diafiltration, and freeze-drying (lyophilization). The solid phase synthesis was carried out by chemical synthesis on a solid support by iterative cycles of nucleotide additions from the 3' end to the 5' end until the oligonucleotide of the appropriate length and sequence is produced. Each chain synthesis of this double stranded oligonucleotide involves four steps: detritylation, coupling, oxidation, and capping (except for the last base). The oligonucleotide is then cleaved from the solid support resin, and the protection groups are removed from the heterocyclic bases and phosphodiester backbone. The bulk of the oligonucleotide is purified, and the right fractions are pooled for further purification. In ultrafiltration and diafiltration step, the oligonucleotide product in solution is further purified, to remove the salts. In the freeze-drying (lyophilization) step, the solution is first filtered through a PES membrane to ensure sterility of the drug substance, the water is then removed via the freeze-drying cycles. The final oligonucleotide product is obtained as a white to pale yellow powder.

Purity of OX425: 85% by IP-RP-LC-UV; Molecular Weight by ESI-MS: 11458.2 Da.

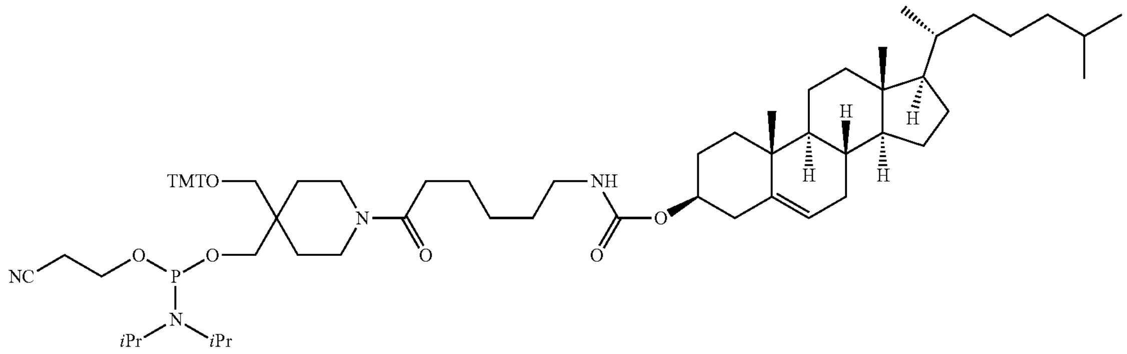

Chol4 phosphoramidite (3-O—(N-cholesteryl)-3-aminopropyl)triethyleneglycol-glyceryl)

OX413, OX416, OX421, OX422, OX423 and OX424

The synthesis of OX413, OX416, OX421, OX422, OX423 and OX424 from Axolabs (Germany) was based on standard solid-phase DNA synthesis using phosphoramidite chemistry, HEG and Chol6 or Chol4 phosphoramidites followed by detritylation, sulfurization, capping and purification steps.

Purity of OX413: 93.8% by AEX-HPLC; Molecular Weight by ESI-MS: 11434.9 Da.

Purity of OX416: 85.3% by AEX-HPLC; Molecular Weight by ESI-MS: 11596.0 Da.

Purity of OX421: 85.1% by AEX-HPLC; Molecular Weight by ESI-MS: 12042.6 Da.

Purity of OX422: 95.1% by AEX-HPLC; Molecular Weight by ESI-MS: 12203.4 Da.

Example 2: OX413 Activates PARP

Materials and Methods

Cell Culture

The triple negative breast cancer cell line MDA-MB-231 from ATCC was used as cellular model. Cells were grown according to the supplier's instructions, in L15 Leibovitz medium supplemented with 10% fetal bovine serum (FBS) and maintained in a humidified atmosphere at 37° C. and 0% $CO_2$.

Quantification of PARylation by Immunofluorescence Analysis

Cells were seeded on LabTek chambers (Fischer scientific) at a concentration of $2\times10^4$ cells and incubated at 37° C. for 24 hours. Cells were then treated with 5 μM OX401 or OX413. Six hours, twenty-four hours and forty-eight hours after treatment, cells were fixed for 20 minutes in 4% paraformaldehyde/PBS 1×, permeabilized in 0.5% Triton X-100 for 10 minutes, blocked with 10% FBS for 15 min, and incubated with primary antibody (anti-pan-ADP-ribose binding reagent, 1/300, Millipore) for 1 hour at room temperature. Secondary goat anti-rabbit IgG conjugated with Alexa-488 (Molecular Probes) was used at a dilution of 1/200 for 45 minutes at room temperature, and DNA was stained with 6-diamidino-2-phenylindole (DAPI). The frequency of positive cells (showing Poly-ADP-ribose polymers, PARylation) was estimated as the number of positive cells over the total number of cells. At least 100 cells were analyzed for each sample.

Results

The inventors analyzed the activation of Poly-(ADP-ribose) polymerase (PARP) in MDA-MB-231 cells after binding of OX413 or of OX401 oligonucleotide moiety which mimics a double-strand break. MDA-MB-231 cells treated with OX401 showed Poly(ADP-Ribose) (PAR) polymer accumulation (PARylation, a results of PARP activation) starting from 24 hours after treatment, with approximately 10% of PARylated cells after 24 hours and 20% 48 hours after treatment (FIG. 1A, B). Cells treated with OX413 showed a higher activation of PARP compared to those treated with OX401, especially 48 hours after treatment, with more than 40% of PARylated cells (FIG. 1A, B). Thus, the inventors observed a higher OX413 target engagement in MDA-MB-231 cells shown by false DNA damage signaling (PARylation) compared to OX401.

Example 3: OX413 Displays a High Antitumor Activity

Materials and Methods

Cell Culture

The triple negative breast cancer cell line MDA-MB-231 from ATCC was used as cellular model. Cells were grown according to the supplier's instructions, in L15 Leibovitz medium supplemented with 10% fetal bovine serum (FBS) and maintained in a humidified atmosphere at 37° C. and 0% $CO_2$.

Drug Treatment and Measurement of Cellular Survival

MDA-MB-231 (5.103 cells/well), were seeded in 96 well-plates and incubated 24 hours at +37° C. before the addition of increasing concentrations of drug for 7 days. Following drug exposure, cell survival was measured using the XTT assay (Sigma Aldrich). Briefly, the XTT solution was added directly to each well containing cell culture and the cells incubated for 5 hours at 37° C. before reading the absorbance at 490 nm and 690 nm using a microplate reader (BMG Fluostar, Galaxy). Cell survival was calculated as the ratio of living treated cells to living mock-treated cells. The $IC_{50}$ (which represents the dose at which 50% of the cells are viable) was calculated by a non-linear regression model using GraphPad Prism software (version 5.04) by plotting the percentage viability against the Log of the drug concentration on each cell line.

Results

Figure 2:
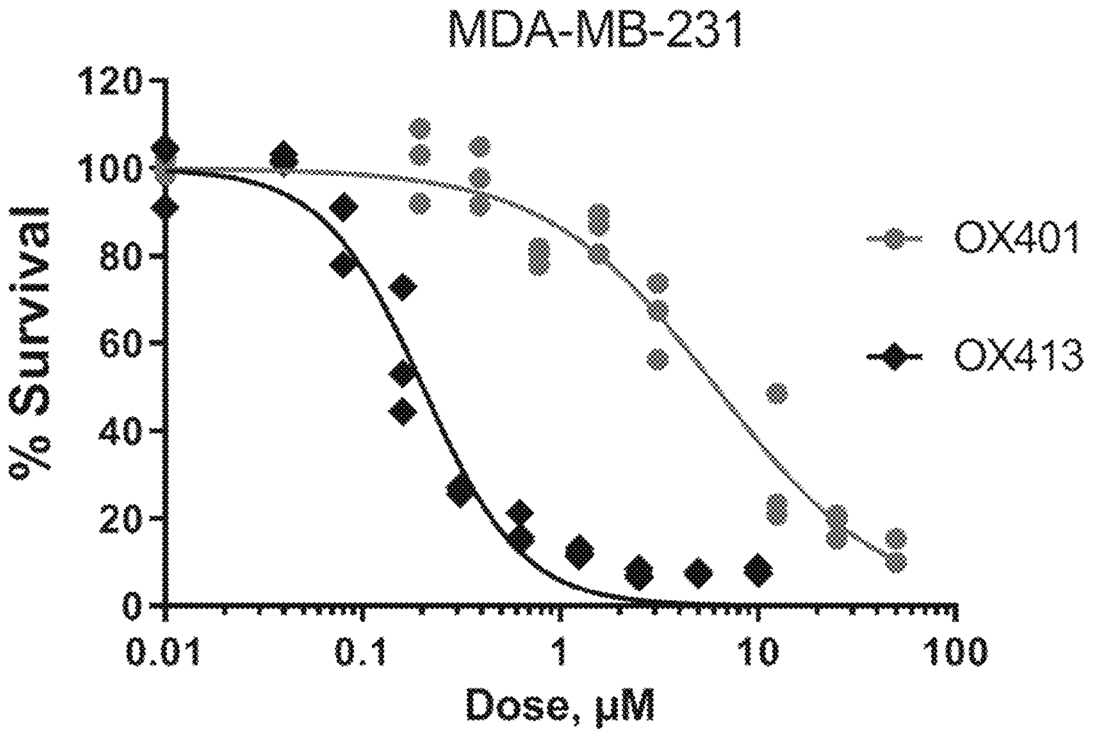
FIG. 2. OX413 displays a high anti-tumor cytotoxicity. MDA-MB-231 cells were treated with increasing doses of OX401 or of OX413 and cell survival was assessed using an XTT assay. Cell survival was calculated as the ratio of living treated cells to living not-treated cells. $IC_{50}$s were calculated according to the dose-response curves using GraphPadPrism software.

To assess the anti-tumor efficacy of OX413, MDA-MB-231 tumor cells were treated with OX413 (black) or OX401 (dark grey) for 1 week to estimate the $IC_{50}$ (median inhibitory concentration), and survival was measured 7 days after treatment using the XTT assay (FIG. 2). Interestingly, OX413 displayed higher antitumor activity compared to OX401, with $IC_{50}$ values 30-fold lower than OX401 (FIG. 2).

Example 4: OX413 Induces Cytoplasmic DNA Accumulation and Triggers an Innate Immune Response

Materials and Methods

Cell Culture

The triple negative breast cancer cell line MDA-MB-231 from ATCC was used as cellular model. Cells were grown according to the supplier's instructions, in L15 Leibovitz medium supplemented with 10% fetal bovine serum (FBS) and maintained in a humidified atmosphere at 37° C. and 0% $CO_2$.

Quantification of PARylation by Immunofluorescence Analysis

Cells were seeded on LabTek chambers (Fischer scientific) at a concentration of $2\times10^4$ cells and incubated at 37° C. for 24 hours. Cells were then treated with OX413 (200 nM). Forty-eight hours after treatment, cells were fixed for 20 minutes in 4% paraformaldehyde/PBS 1×, permeabilized in 0.5% Triton X-100 for 10 minutes, blocked with 10% FBS for 15 min, and incubated with primary antibody (anti-pan-ADP-ribose binding reagent, 1/300, Millipore) for 1 hour at room temperature. Secondary goat anti-rabbit IgG conjugated with Alexa-488 (Molecular Probes) was used at a dilution of 1/200 for 45 minutes at room temperature, and DNA was stained with 6-diamidino-2-phenylindole (DAPI).

Micronuclei (MN) and Cytoplasmic Chromatin Fragments (CCFs) Detection

MDA-MB-231 cells were seeded on cover slips (Menzel, Braunschweig, Germany) at 5E4 cells in 6-well plates at appropriate densities and then treated for 48 hours with or without OX413 (50 nM or 100 nM). After treatment, cells were fixed by 4% paraformaldehyde/PBS 1× for 20 minutes, permeabilized in 0.5% Triton X-100 for 10 minutes and blocked 15 minutes with 10% FBS. Then, cells were washed with PBS, stained by picogreen (Invitrogen, for CCF detection) and/or DAPI (for MN analysis) for 5 minutes. The percentage of MN was estimated as the number of cells presenting a MN structure among the total cell number. Around 150 cells were analyzed for each condition.

Flow Cytometry Analysis

MDA-MB-231 cells were seeded on T25 flask at 2E5 cells/mL and then treated for 48 hours with or without OX413 at 200 nM. For intracellular staining (pSTING analysis), cells were washed, then fixed in PBS/70% Ethanol for at least 1 hour at 4° C. Cells were then washed, permeabilized with PBS/0.2% TritonX-100 solution at RT for 10 min, and saturated with PBS/2% Bovine Serum Albumin (BSA) solution at RT for 10 min. Then, cells were washed with PBS and incubated for 1 hour with an Alexa488-conjugated anti-pSTING antibody (cell signaling, Netherlands, 1/200) before flow cytometry analysis (Guava EasyCyte 12H, Luminex, Germany). For cell-surface receptors staining, cells were harvested and washed directly after treatment end, and then incubated for 1 hour at 4° C. with an Alexa-488-coupled anti-MIC-A antibody (R&D System, 1/200) and APE-coupled anti-PD-L1 antibody (Abcam, 1/200) Stained cells are then washed with PBS and fluorescence intensities were acquired with a Guava EasyCyte 12H flow cytometer (Luminex, Germany). Data were analyzed using FlowJo software (Tree Star, CA).

ELISA to Detect CCL5

MDA-MB-231 tumor cells were treated with or without OX413 (500 nM) for 24 and 48 hours with or without T lymphocytes. Cell culture supernatants were then harvested and centrifuged at 1,500×g for 10 minutes to remove debris.

The 96 well plate strips included with the kit (Human SimpleStep CCL5 ELISA Kit—Abcam—ab174446) were supplied ready to use. 50 μl of each supernatant were added to each well in duplicate with 50 μl of the Antibody cocktail and then, incubated for 1 h at RT on a plate shaker set to 400 rpm, after which it was washed with 1× Wash buffer PT. Then, 100 μl of TMB substrate were added to each well and incubated for 10 min in the dark on a plate shaker set to 400 rpm. 100 μl of stop solution were then added to each well for 1 minute on a plate shaker and the resulting luminescent signals were measured on a microplate reader (Enspire™ Perkin-Almer).

Results

Figure 3A:
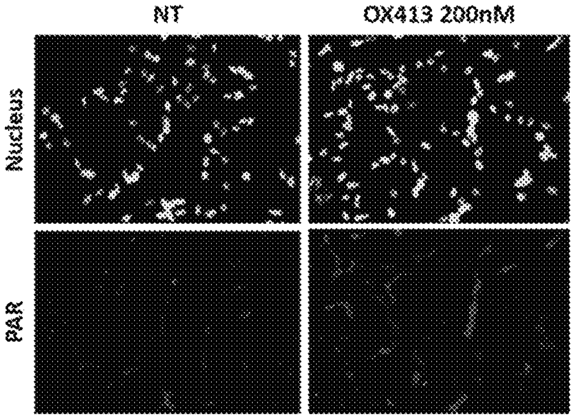
FIGS. 3A-3G. OX413 induces cytoplasmic DNA accumulation and triggers an innate immune response.

To confirm the efficacy of the optimized OX413 molecule, the inventors tested if the chemical modifications did not affect its ability to fix PARP1 protein. Hyper-activation of PARP proteins in OX413-treated MDA-MB-231 cells was assessed by immunofluorescence analysis of PARylation (FIG. 3A). OX413 treated cells were positive for the "false" nuclear PARylation signaling, confirming the target engagement (FIG. 3A).

Figure 3B:
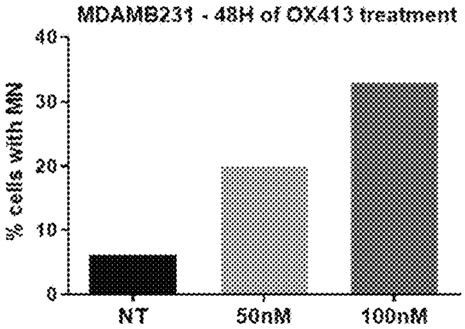
Figure 3C:
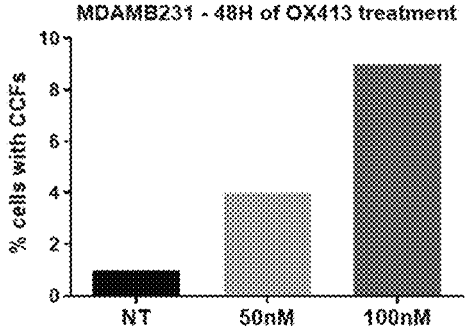
Figure 3D:
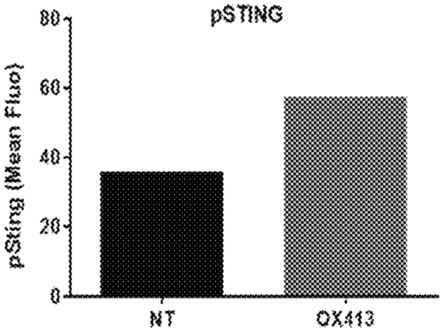
Figure 3E:
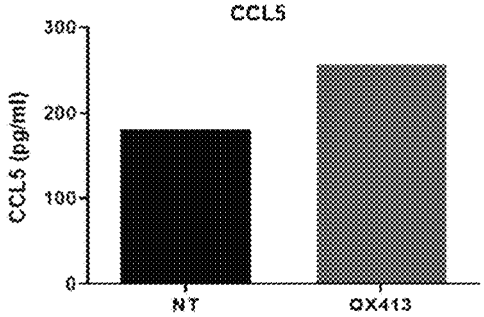
Figure 3F:
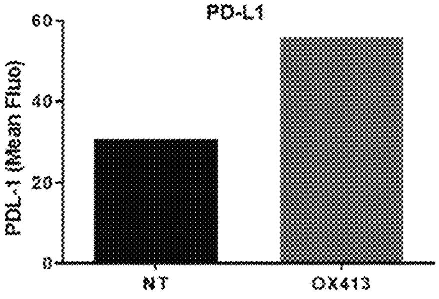
Figure 3G:
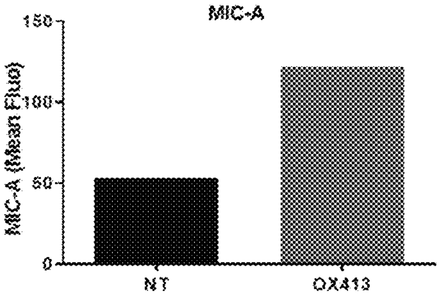

To check if this higher anti-tumor efficacy is due to a more potent effect on cell stress and DNA repair, the inventors studied by immunostaining the amount of cytoplasmic unrepaired DNA induced by OX413 treatment (at the doses of 50 and 100 nM) through the quantification of Micronuclei (MN) and cytoplasmic chromatin fragments (CCFs). OX413 induced a significant increase of cells with MN (FIG. 3B) and CCFs (FIG. 3C). To check if OX413-induced accumulation of cytoplasmic DNA could activate the STING pathway, the inventors analyzed by flow cytometry the phosphorylated and activated form of STING (pSTING). OX413 induced an activation of STING 48 hours after treatment (Mean fluorescence 57.4 compared to 35 in non-treated cells) (FIG. 3D). To confirm the STING pathway activation, the inventors also analyzed the secretion of CCL5 chemokine in OX413-treated cell supernatant. OX413 induced an increase of CCL5 secretion 48 after treatment (FIG. 3E). Among the consequences of STING pathway activation in tumor cells there is PD-L1 (programmed death ligand 1) up-regulation, probably a reaction to protect against the immune system. The inventors analyzed the level of cell-surface associated PD-L1 in OX413-treated cells. OX413 induced a 2-fold increase in membrane associated PD-L1 compared to non-treated cells (FIG. 3F). Some reports have also shown that tumor STING activation could increase NK cell ligands on tumor cells, such as NKG2D ligands (MIC-A, MIC-B, ULBP1/6). Thus, expression of MIC-A at the surface of OX413-treated cells was analyzed. Interestingly, cells treated with OX413 showed more than 2-fold increase of cell-surface MIC-A expression (FIG. 3G).

These results confirmed that optimizing the structure of OX401 by increasing its stability allowed to increase the amount of molecule reaching the target and thus the anti-tumor efficacy and anti-tumor immune responses.

Example 5: OX413 Induces In Vivo Intra Tumor PARP and STING Pathway Activation Resulting in Increased Levels of Tumor Infiltrating Leucocytes Materials and Methods ELISA to Detect CCL5

To quantify the level of CCL in the tumor microenvironment (TME), supernatants after tumor dissociation were harvested and centrifuged at 1,500×g for 10 minutes to remove debris. The 96 well plate strips included with the kit (Human SimpleStep CCL5 ELISA Kit—Abcam—ab174446) are supplied ready to use. 50 μl of each supernatant were added to each well in duplicate with 50 μl of the Antibody cocktail and then, incubated for 1 h at RT on a plate shaker set to 400 rpm, after which it was washed with 1× Wash buffer PT. Then, 100 μl of TMB substrate were added to each well and incubated for 10 min in the dark on a plate shaker set to 400 rpm. 100 μl of stop solution were then added to each well for 1 minute on a plate shaker and the resulting luminescent signals were measured on a microplate reader (Enspire™ Perkin-Almer).

In Vivo Experiments, Tumor Digestion, Cell Sorting and Flow Cytometry

EMT6 cell-derived xenografts (CDXs) were obtained by injecting $4 \cdot 10^5$ cells into the right flank of a 6- to 8-week-old adult Balb/c female (Janvier). The animals were housed at least 1 week before tumor engraftment under controlled conditions of light and dark (12 hours/12 hours), relative humidity (55%) and temperature (21° C.). Tumor growth was evaluated three times a week, using a caliper, and tumor volume was calculated using the following formula: (length×width×width)/2. The local animal experimentation ethics committee approved all experiments.

Mice were randomized when engrafted tumors reached between 150 and 300 $mm^3$. OX413 (10 mg/kg) was administered intra peritoneally. Mice were sacrificed at the indicated times (6, 24 or 72 hours post treatment), and EMT6 CDXs extracted, finely minced and blended with the gentleMACS octo dissociator (Miltenyi Biotec) using the mouse tumor dissociation kit (Miltenyi Biotec, 130-096-730) according to the manufacturer's instructions. Dissociated tumor cells were washed with DMEM medium and red blood cells lysed with RBC lysis solution (Miltenyi Biotec, 130-094-183). Tumor-infiltrating leucocytes (TILs) were then enriched using the CD45 microbeads (Miltenyi Biotec, 130-110-618) and the MultiMACS Cell24 Separator plus (Miltenyi Biotec).

CD45+ cells were resuspended in FACS Buffer (PBS containing 2% BSA and 2 mM EDTA), and stained with the antibody panel (anti-CD45-VioBlue, CD3-FITC, CD8a-PE-Vio770, CD4-APC-Vio770, CD49b-PE, CD335-APC, CD11c-PerCP-Vio700) or corresponding isotypes during 30 min at 4° C. CD45− cells, containing essentially EMT6 tumor cells, were stained with the anti-PD-L1-PE antibody (30 min, 4° C.), and then fixed and permeabilized using the FoxP3/transcription Factor staining buffer set (ThermoFisher, 00-5523-00), according to the manufacturer's guidelines, and incubated 30 min at 4° C. with anti-Poly (ADP)-ribose antibody (clone 10H; MERCK, MABC547). Cells were then washed, resuspended in PBS and analyzed using a Guava EasyCyte 12HT flow cytometer (Luminex). Compensation was performed manually using single color and isotype controls. Signal threshold definition was defined using all-stain, unstained and isotype controls. Analysis was performed on FlowJo software.

Results

Figures 4A, 4B, 4C, 4D:
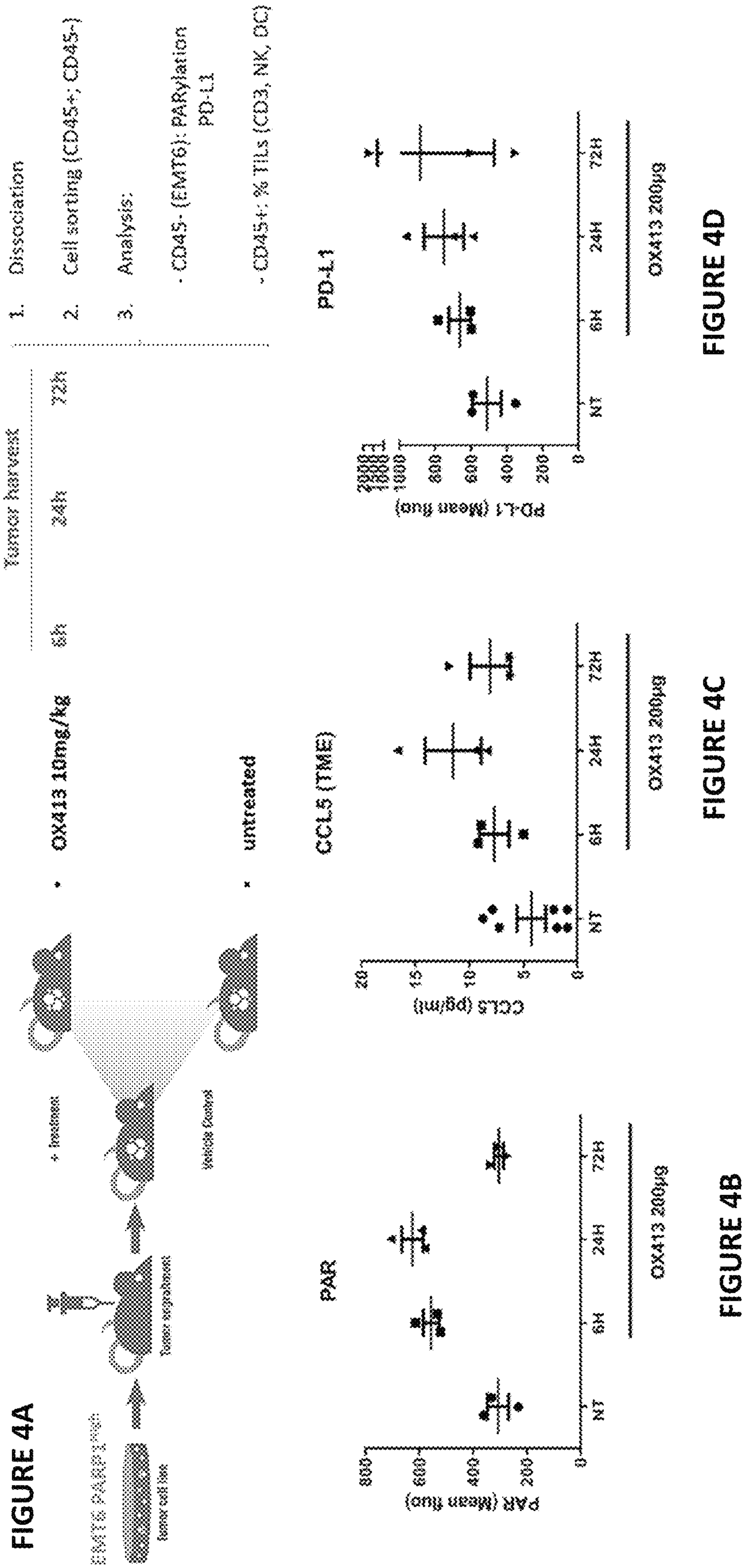
FIGS. 4A-4E. OX413 induces PARP and STING activation in vivo. EMT6 cell-derived xenografts tumors treated with OX413 (10 mg/kg) during 6, 24 or 72 H were extracted, dissociated, and sorted CD45+ or Cd45− (mostly EMT6 cells) (FIG. 4A). On EMT6 cells, (FIG. 4B) PARP, (FIG. 4D) PD-L1, and (FIG. 4C) CCL5 expression were analyzed for each condition.

The inventors evaluated the efficacy of OX413 in xenografts derived from the syngenic breast tumor model EMT6. EMT6 cell-derived xenografts were treated with vehicle or OX413 (200 μg), and tumors harvested at 6, 24 or 72 hours after treatment (FIG. 4A). To confirm OX413 uptake into tumors and target engagement, inventors analyzed in EMT6 cells, sorted from dissociated tumors, PARP activation and PD-L1 levels on cell surface. OX413 treatment induced a significant PARP activation starting from 6 hours after treatment, indicating a tumor uptake and target engagement (FIG. 4B). This OX413-induced PARylation returns to the basal level 72 hours post treatment, indicating that repeating the treatment twice a week is necessary to maintain a high target engagement (FIG. 4B). To check if this PARylation is associated to STING pathway activation, as observed in vitro experiments, inventors quantified tumor CCL5 release in tumor microenvironment (TME). Interestingly, TME-CCL5 increased in a manner similar to PARylation, with a peak 24 hours after treatment and a decline at 72 hours (FIG. 4C). Tumor cell surface PD-L1 also increased after treatment, confirming the inventors' previous in vitro results and the link between PARP activity abrogation and PD-L1 increase, which could contribute to immunosuppression (FIG. 4D).

Figure 4E:
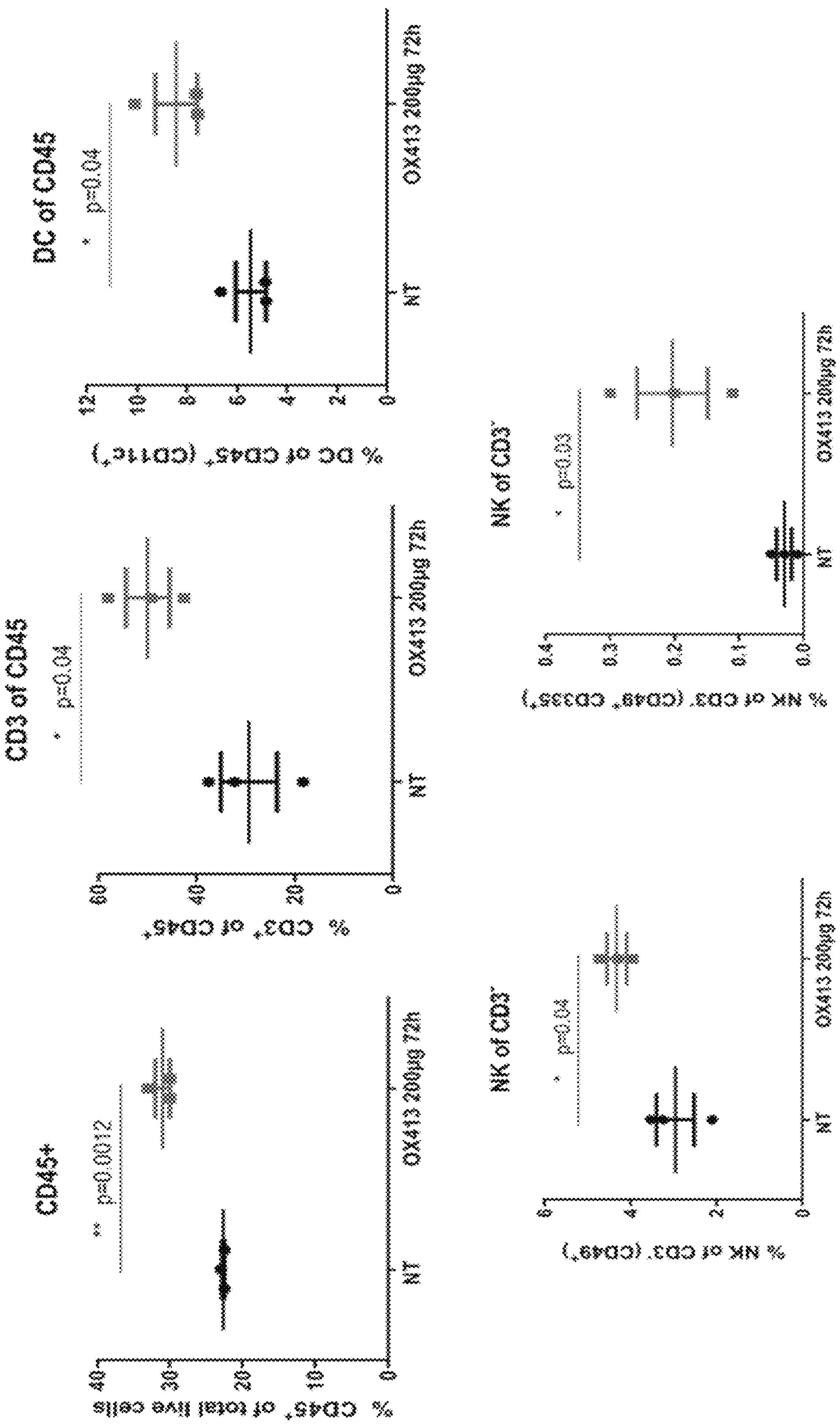
Figure 5A:
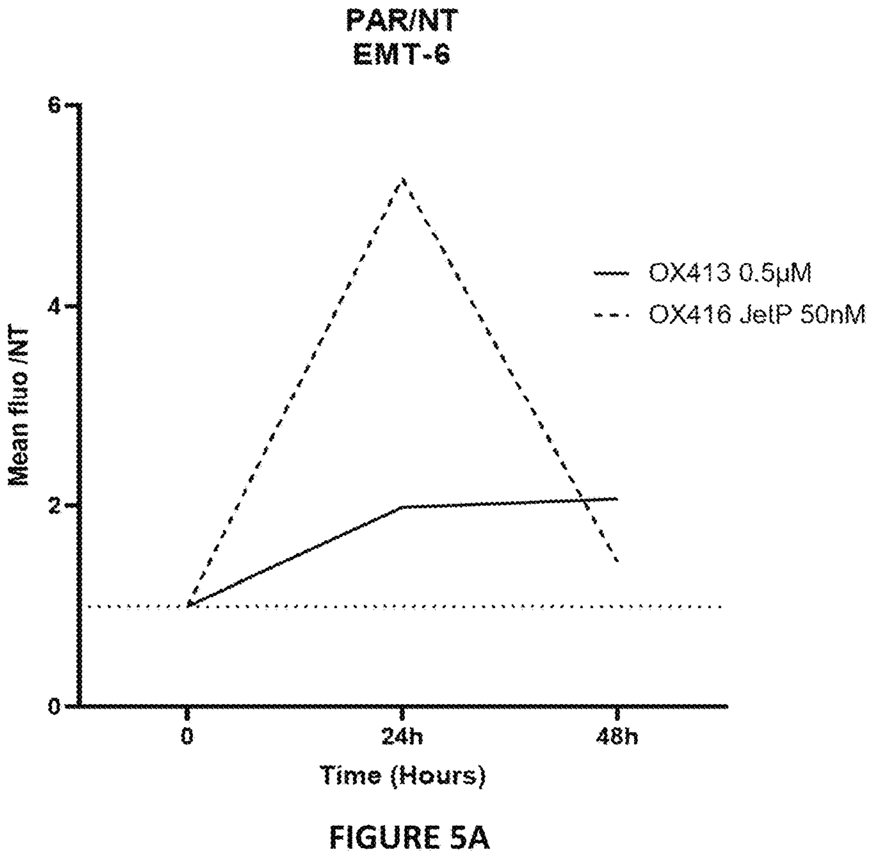
FIGS. 5A-5F. OX413 and OX416 induce PARP target engagement and STING pathway activation. Flow cytometry analysis of PARylation (FIGS. 5A, 5D), STING (FIGS. 5B, 5E) and pSTING (FIGS. 5C, 5F), 24 and 48 hours after OX413 (500 nM in EMT6 or 100 nM in MDA-MB-231) or OX416 treatment (50 nM). Treatment in EMT6 cells (FIGS. 5A, 5B, 5C) and MDA-MB-231 cells (FIGS. 5D, 5E, 5F).
Figure 5B:
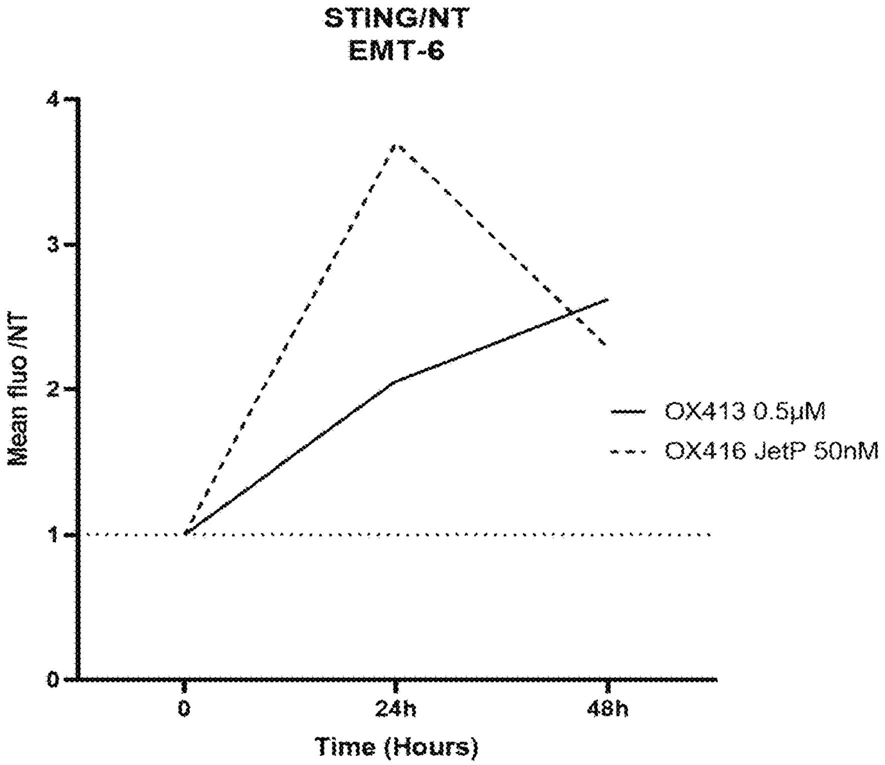
Figure 5C:
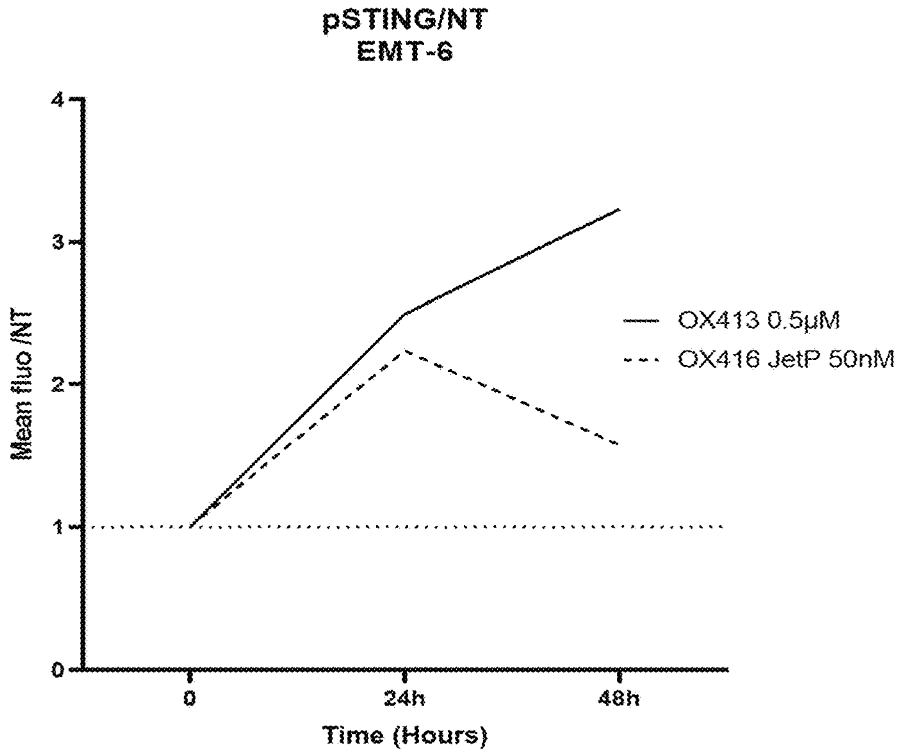
Figure 5D:
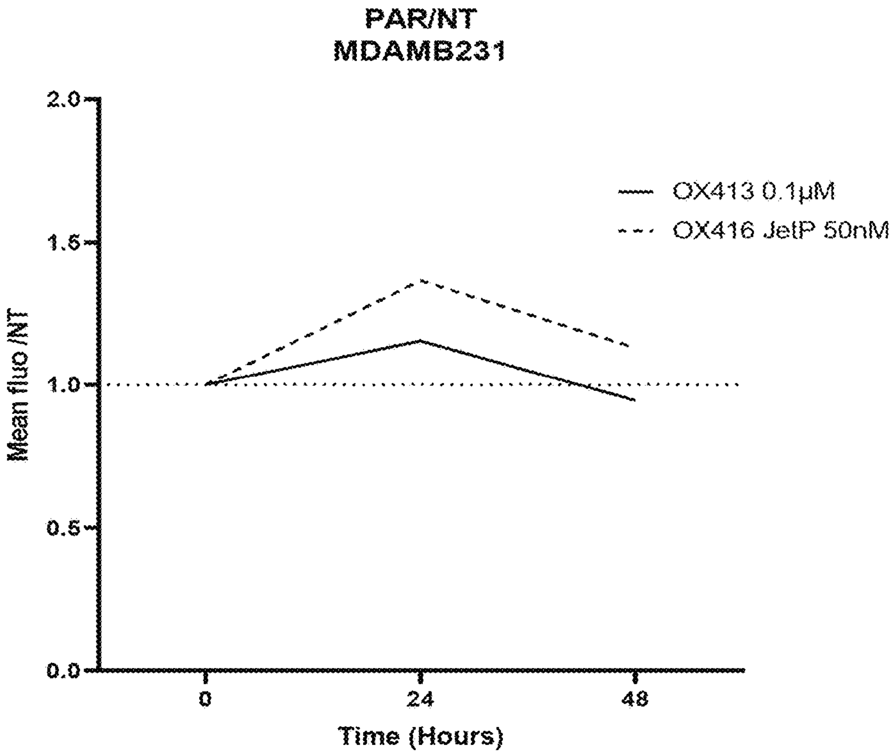
Figure 5E:
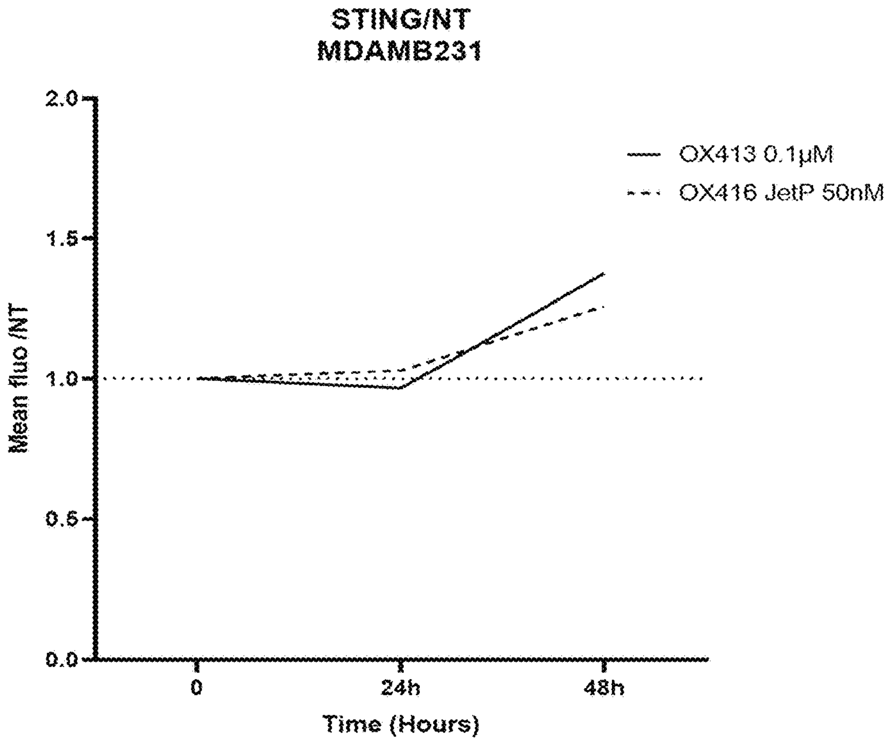
Figure 5F:
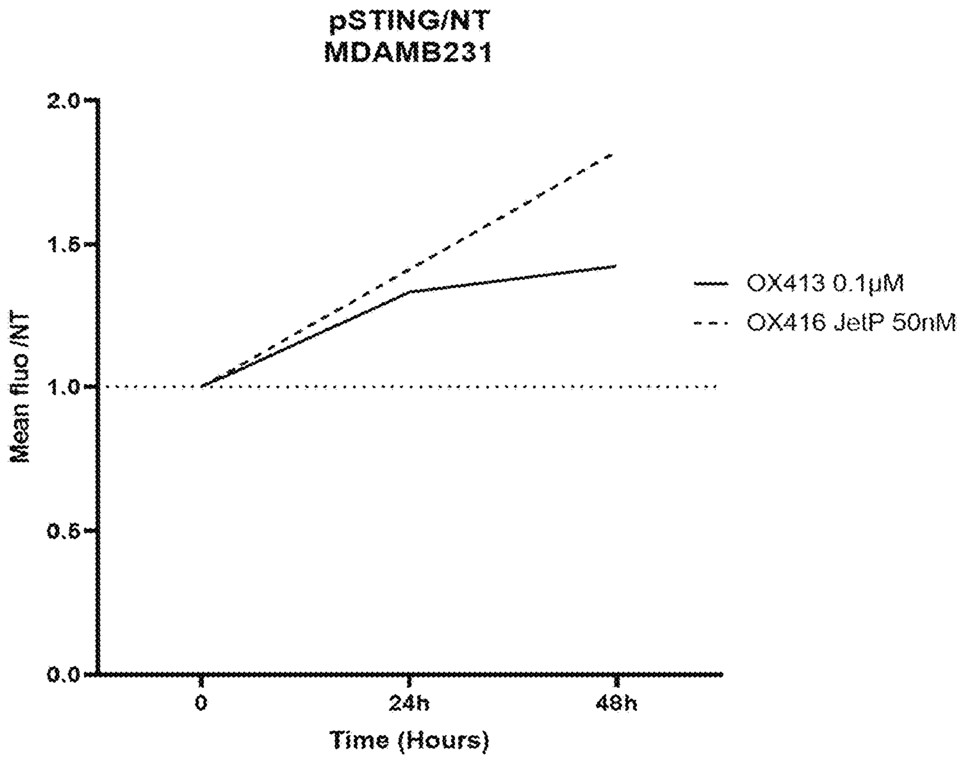

The inventors next thought to define the effects of OX413 on the immune microenvironment. Flow cytometric analysis of tumor-infiltrating leucocytes (TILs; CD45+ cells) showed that OX413 significantly increases total TILs as early as 3 days after treatment, as measured by CD45 staining (FIG. 4E). The proportions of T cells (CD3+) among CD45+ cells were significantly increased in response to OX413 treatment (FIG. 4E). OX413 not only augmented T cells tumor infiltration (CD45+, CD3+) but also natural killer (NK) cells (total infiltrating NK cells: CD3−, CD49b+; activated infiltrating NK cells: CD3−, CD49b+, CD335+—FIG. 4E), suggesting an activation of both innate and adaptive immune responses. Moreover, the TME became populated in dendritic cells (DC) after OX413 treatment (CD45+, CD11c+).

Taken together, these results demonstrate an effective OX413-induced PARP and STING pathway activation in tumors, which increases innate and adaptive immune cells recruitment and boost a productive anti-tumor immune response.

Example 6: OX413 and OX416 Trigger PARP Activation and Induces an Innate Immune Response

Materials and Methods

Cell Culture

The MDA-MB-231 human triple negative breast cancer cell line and the mouse EMT6 breast cancer cell line (from ATCC) were used as cellular models. MDA-MB-231 cells were grown according to the supplier's instructions, in L15 Leibovitz medium supplemented with 10% fetal bovine serum (FBS) and maintained in a humidified atmosphere at 37° C. and 0% $CO_2$. EMT6 cells were grown in RPMI medium supplemented with 10% FBS and maintained in a humidified atmosphere at 37° C. and 5% $CO_2$.

Transfection of OX416 into cells was performed with JetPRIME (JetP) reagent (Polyplus). Briefly, OX416/JetP complexes have been prepared extemporal by incubating at RT 50 nM of OX416 (diluted in 200 μL of jetPRIME buffer), with 2 μl of jetPRIME transfecting reagent. The complexes were then added to cells seeded in 2 ml of complete medium (in a well of 6-well plates).

Quantification of PARylation and STING Pathway Activation by Flow Cytometry

MDA-MB-231 or EMT6 cells were seeded on T25 flask at 2E5 cells/mL and then treated for 24 and 48 hours with OX416/JetP (50 nM) or OX413 (100 nM and 500 nM, respectively) or no treatment (NT). After treatment, cells were harvested and washed, fixed in PBS/70% Ethanol during at least 1 hour at 4° C., and then washed and permeabilized with PBS/0.2% TritonX-100 solution at RT for 10 min, saturated with PBS/2% Bovine Serum Albumin (BSA) solution at RT for 10 min. Then, cells were washed with PBS and incubated 1 hour with an Alexa488-conjugated anti-pSTING antibody (cell signaling, Netherlands, 1/200) and an Alexa647-conjugated anti-PAR antibody (Merck Millipore, 1/200) before flow cytometry analysis (MACSQuant10, Miltenyi, Germany). Data were analyzed using FlowJo software (Tree Star, CA).

Results

The inventors first analyzed the activation of Poly-(ADP-ribose) polymerase (PARP) by OX413 and OX416 in MDA-MB-231 and EMT6 cells. This enzyme is activated after binding of OX416 or OX413 oligonucleotide moiety, which mimics a double-strand break.

The data are presented as mean fold change of differential fluorescence between treated conditions (OX413 or OX416) and non-treated conditions (NT). Tumor cells treated with OX413 showed Poly(ADP-Ribose) (PAR) polymer accumulation (PARylation, a result of PARP activation) starting from 24 hours after treatment, reaching a plateau at 48 hours after treatment in EMT6 cells but very transient in MDA-MB-231 cells (FIG. 5 A, D). Cells treated with OX416 showed an activation of PARP at 24 hours after treatment and a significant decrease 48 hours after treatment, probably due to the significant drug-induced cell death at this time-point (FIG. 5 A, D). These results confirm the efficiency of the optimized OX416 molecule, and that the chemical modifications did not affect its ability to bind PARP-1 proteins.

Both PARP hijacking and hyperactivation result in a high accumulation of cytoplasmic unrepaired DNA that could activate the STING pathway. To check if OX413 and OX416 molecules trigger STING pathway activation, inventors analyzed by flow cytometry the total amount of STING protein (FIG. 5 B, E) and of the phosphorylated and activated form of STING, pSTING (FIG. 5 C, F). In both cell lines, OX413 and OX416 induced an activation of STING pathway starting at 24 hours after treatment.

Example 7: Pharmaceutical Properties/PK

Materials and Methods

Female BAL/C mice were purchased from Janvier-labs. One milligram of OX413, OX416, OX421, OX422 and OX423 were injected by intraperitoneal (i.p.) route to mice and blood was collected at different times: 15 min, 30 min, 1 h, 2 h, 4 h and 24 h. The blood collection was performed by mandibular vein puncture for the first five time points and by intracardiac terminal puncture under deep gas anesthesia for the 24 h time points. Blood was collected into tubes with anticoagulant (K2-EDTA) and centrifuged at 1,200 g for 15 minutes at +4° C. to recover plasma. The plasma samples were stored in propylene tubes at 80° C.

A solution of proteinase K (solK) was prepared by diluting 5 μL of proteinase K sol>20 mg/mL, 20 μL of buffer (400 μL $CaCl_2$) 0.5M, 100 μl HEPES 1M, 500 μl.eau) and 75 μL of MilliQ water. A fixed volume of samples (around 10 μL) was diluted with the same volume of proteinase K solution (solK) and warmed at 55° C. for 1 h before direct injection in High Pressure Liquid Chromatography equipped with a Waters BEH C18 column. A gradient was performed by increasing the percentage of acetonitrile compared to the Triethylamine (TEA)/Hexafluoroisopropanol(HFIP) phase along the time.

Results

Figure 6A:
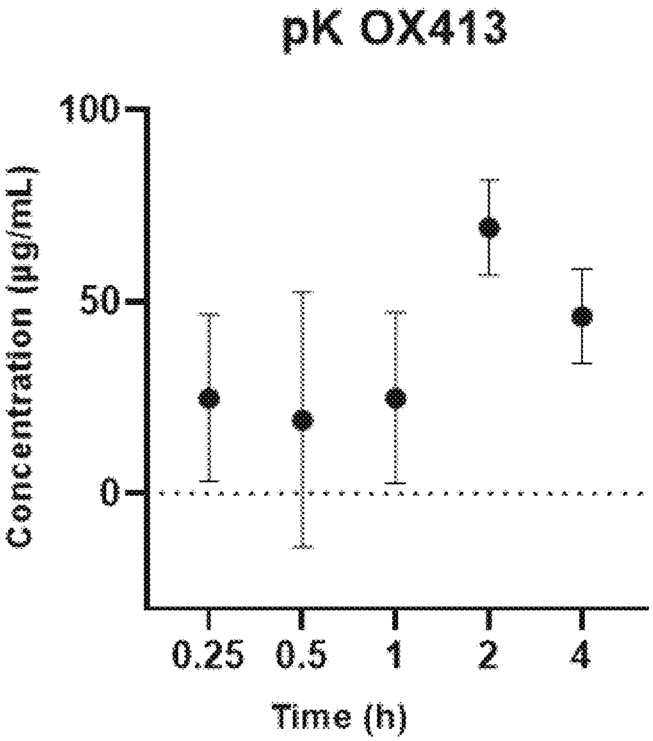
FIGS. 6A-6C. Pharmacokinetic of OX413, OX421 and OX422. Mean concentrations of OX413 (FIG. 6A), OX422 (FIG. 6B) and OX423 (FIG. 6C) over time in mice blood, following i.p. drug (OX413, OX422 or OX423) administration.
Figure 6B:
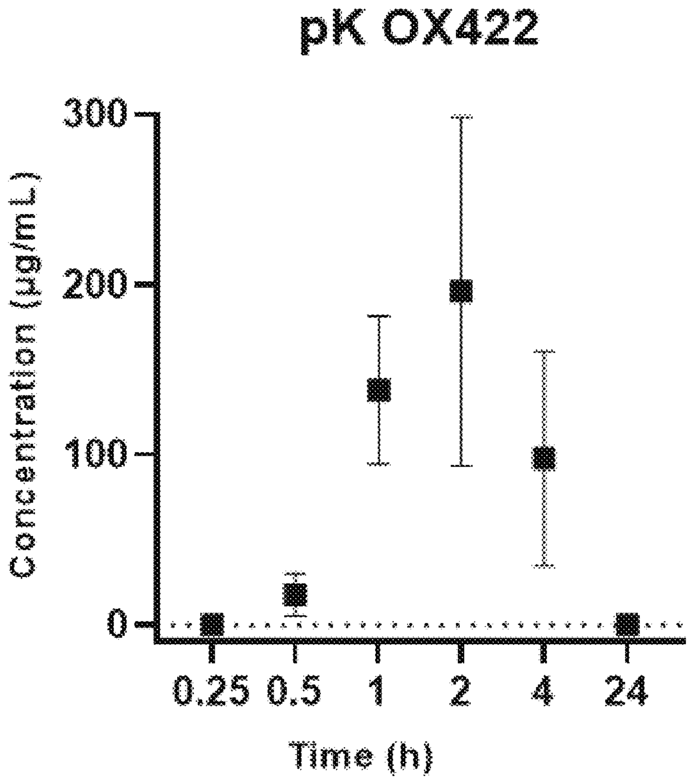
Figure 6C:
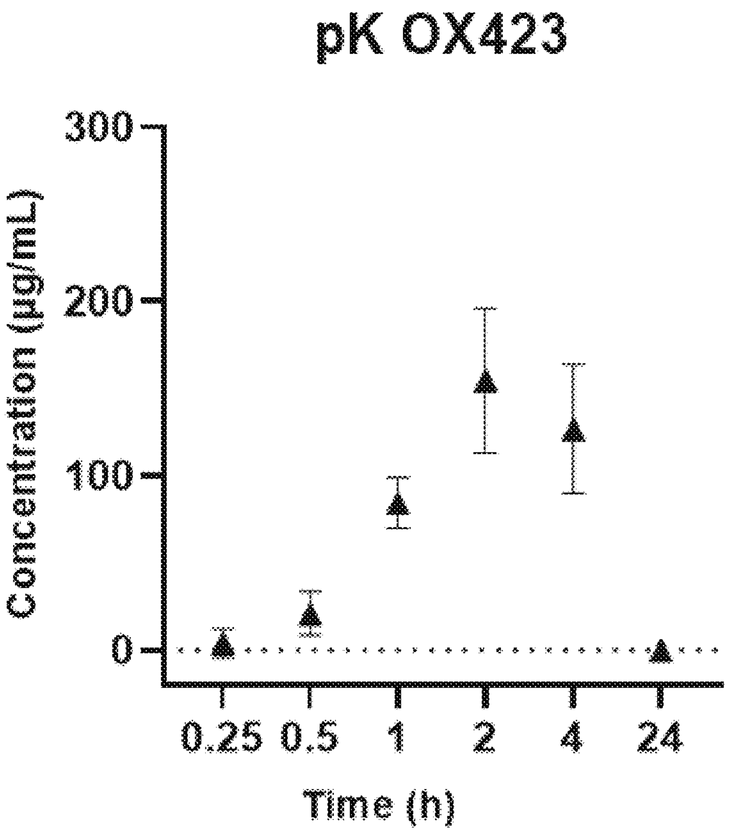

Injection of OX413, OX422, or OX423 at a dose of 1 mg by i.p. route in mice, leads to a high plasmatic concentration maximum (Cmax) of compounds (FIG. 6). Cmax values of OX422 and OX423 (respectively 196.0 μg/mL and 154.7 μg/mL, FIGS. 6B, 6C) as measured by HPLC method, were higher than the Cmax value of OX413 (69.26 μg/mL), at 2 hours (FIG. 6A).

The measured Area Under the plasma drug concentration-time Curve (AUC) was significantly higher when OX422 or OX423 was administered (respectively 1480 μg·h/mL and 1700 μg·h/mL) in comparison with OX413 (179 μg·h/mL).

Cmax and AUC values following the i.p. administration of OX413, OX422 and OX423 are shown in Table 1 below:

| | Time for Cmax (h) | Cmax (μg/mL) | AUC (μg · h/mL) |
|---|---|---|---|
| OX413 | 2 | 69.26 | 179 |
| OX422 | 2 | 196.0 | 1480 |
| OX423 | 2 | 154.7 | 1700 |

Compounds having 2'OMe modifications have improved pharmaceutical properties in comparison with compounds having FANA modifications.

Example 8: Kinetics of Association/Dissociation and Strength of Interaction (KD)

Materials and Methods

The interaction of OX413 and OX416 with the human poly-[ADP-ribose polymerase 1 protein (PARP-1) (115 kDa) has been characterized by SPR technique using a Biacore T100 instrument from GE Healthcare Life Sciences and using human His-tagged PARP-1 protein, purchased from Thermofisher. For the evaluation of PARP1/hairpin interactions, the PARP1-His has been captured on anti-His antibodies immobilized on the surface of the carboxymethylated chip.

Results

The kinetics of association ($k_{on}$) and dissociation ($k_{off}$) as well as the strength of interaction (KD) of OX413 and of OX416 are reported in Table 2 below:

| | $K_D$ (nM) | $k_{on}$ ($M^{-1}s^{-1}$) | $k_{off}$ ($s^{-1}$) |
|---|---|---|---|
| OX413 | 45 ± 11 | $3.7 * 10^4 \pm 5 * 10^3$ | $1.7 * 10^{-3} \pm 2 * 10^{-4}$ |
| | 85 ± 7 | $4.7 * 10^3 \pm 2 * 10^2$ | $3.9 * 10^{-4} \pm 1 * 10^{-5}$ |
| OX416 | 2.4 ± 0.2 | $1.6 * 10^6 \pm 2 * 10^5$ | $3.9 * 10^{-3} \pm 4 * 10^{-4}$ |

OX416 has a better interaction with PARP-1 protein in comparison with OX413.

Example 9: OX413 and OX416 Display a High Antitumor Activity

Materials and Methods

Cell Culture

The murine mammary carcinoma EMT-6 cell line was purchased from American Type Culture Collection, USA. EMT-6 tumor cells were submitted to in vitro pressure with olaparib to obtain a tumor cell line overexpressing PARP resulting in EMT-6 PARP high cell line. Cells were cultured in Waymouth containing 2 mM L-glutamine supplemented with 10% fetal bovin serum and 1% Peni-streptomycin (Gibco) at 37° C. in an atmosphere of 5% $CO_2$.

Immuno-Competent Balb c Mice Bearing EMT-$6^{PARP\ high}$ Breast Tumor Cells, Drug Treatment and Measurement of Tumor Growth Female Balb/c (Balb/cByJ) mice, aged 6-8 weeks, were obtained from Janvier (Saint-Berthevin, France). EMT-$6^{PARP\ high}$ cells ($5\times10^5$ cells/mouse into 200 μl of Waymouth medium) were subcutaneously implanted into the flank of mice. When the average tumor volume reached approximately 25-40 $mm^3$, animals were randomized, and the following treatment was given to cohorts of 7 mice as described in Table 3 below:

| Group | Treatment | Route | Dose | Schedules |
|---|---|---|---|---|
| I | Untreated | — | — | — |
| II | OX416 | Intraperitoneal | 20 mg/kg | Twice a week |
| III | OX413 | Intraperitoneal | 20 mg/kg | Twice a week |
| IV | OX421 | Intraperitoneal | 20 mg/kg | Twice a week |

Results

Figure 7:
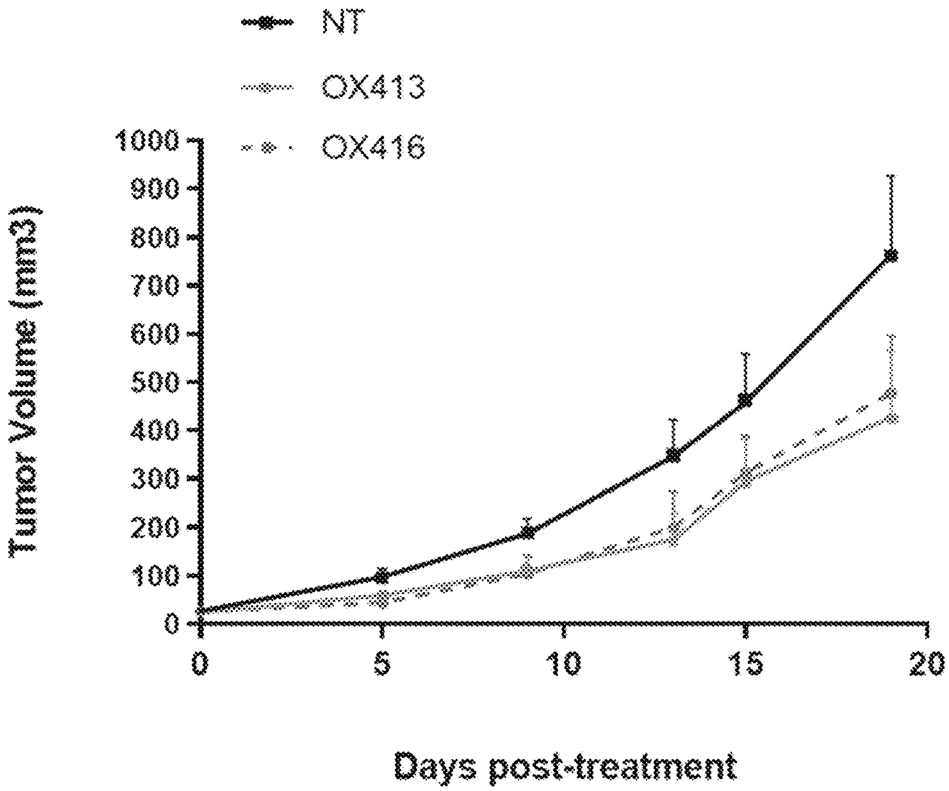
FIG. 7. Anti-tumor efficacy of OX413 and OX416 in EMT-$6^{PARP\ high}$ breast model. OX413 (20 mg/kg, twice/week) and OX416 (20 mg/kg, twice/week) treatment inhibited tumor growth in Balb/c mice bearing EMT-$6^{PARP\ high}$ breast tumor cells.

Both OX413 (continuous lines, grey circles) and OX416 (dotted lines, grey circles) compounds induced a marked inhibition of tumor growth compared to untreated group (NT, black squares), nineteen days after OX413 or OX416 treatment (FIG. 7).

Example 10: OX425 Traps and Hyperactivates PARP

Materials and Methods

Cell Culture

The triple negative breast cancer cell lines MDA-MB-231 and MDA-MB-436 from ATCC were used as cellular models. Cells were grown according to the supplier's instructions, in L15 Leibovitz medium (Gibco, Cat #11570396) supplemented with 10% fetal bovine serum (FBS, Biowest; Cat #: S1810-100) and 1% penicillin/streptomycin (Gibco; Cat #: 15140-122) and maintained in a humidified atmosphere at 37° C. and 0% $CO_2$. In addition, L15 Leibovitz medium was supplemented with 10 μg/ml insulin (Sigma, Cat #I9278), 16 μg/ml glutathione (Sigma, Cat #Y0000517) for MDA-MB-436 cell line.

Electrophoretic Mobility-Shift Assay (EMSA)

To confirm the interaction between OX425 and its target Poly-(ADP-ribose) polymerase 1 (PARP1) protein, an EMSA method was performed. For this purpose, 1 pmol of OX425 (Axolabs; Batch #K1K2) was eluted in 10 mM EDTA buffer with or with the addition of recombinant PARP1 protein (Active Motif, Cat #81037). Two different ratio: 1:1 and 1:5 (drug:recombinant protein) were tested and incubated for 30 min at 37° C. using a THERMO MIXER C (Eppendorf) in a final volume of 40 μL. After incubation time, 1× of DNA loading dye (ThermoFisher, Cat #R0631) were added directly into the tubes. 15 μL of samples were load on Novex™ TBE 20% polyacrylamide gel (Thermofisher, Cat #EC63155BOX). The electrophoresis was performed with 1×TBE buffer (Thermofisher, Cat #15581044) and run for 80 min at 180V. As a leader the Orange 5 bp DNA leader (ThermoFisher, Cat #SM1303) was used. At the end of the migration, gels were washed with distilled water and stained for 20 min with SyberGold (1/10000 in distilled water). Gels were analyzed with UV transilluminator (PERKIN ELMER, ENSPIRE ALPHA 2390).

Quantification of PARylation by Immunofluorescence Analysis

Cells are seeded on LabTek chambers (Fischer scientific) at a concentration of $2\times10^4$ cells and incubated at 37° C. for 24 hours. Cells were then treated with 1, 2.5 and 5 μM OX425 (Axolabs; Batch #K1K2). Twenty-four hours after treatment, cells were fixed for 20 minutes in 4% paraformaldehyde/PBS 1×, permeabilized in 0.5% Triton X-100 for 10 minutes, blocked with 10% FBS (Sigma, Cat #F0685) for 15 min, and incubated with primary antibody (anti-pan-ADP-ribose binding reagent, 1/300, Millipore, Cat #MABE1016) for 1 hour at room temperature. Secondary goat anti-rabbit IgG conjugated with Alexa-488 (Molecular Probes, Cat #10453272) was used at a dilution of 1/200 for 45 minutes at room temperature, and DNA was stained with 6-diamidino-2-phenylindole (DAPI, Life Technologies; Cat #: 62248). The frequency of positive cells (showing Poly-ADP-ribose polymers, PARylation) was estimated as the number of positive cells over the total number of cells. At least 100 cells were analyzed for each sample.

Results

Figure 8A:
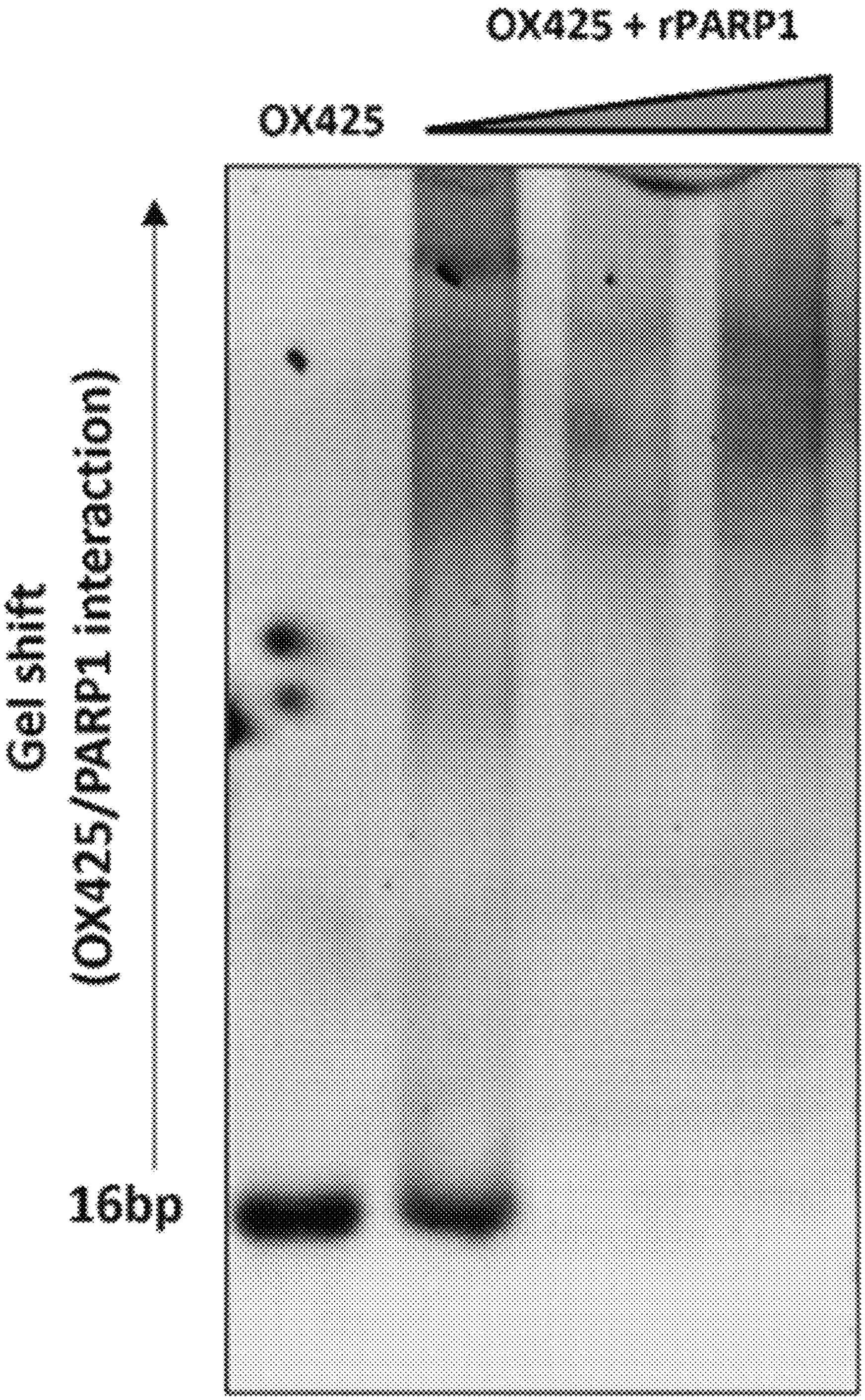
FIGS. 8A-8B. OX425 traps and hyperactivates PARP.
Figure 8B:
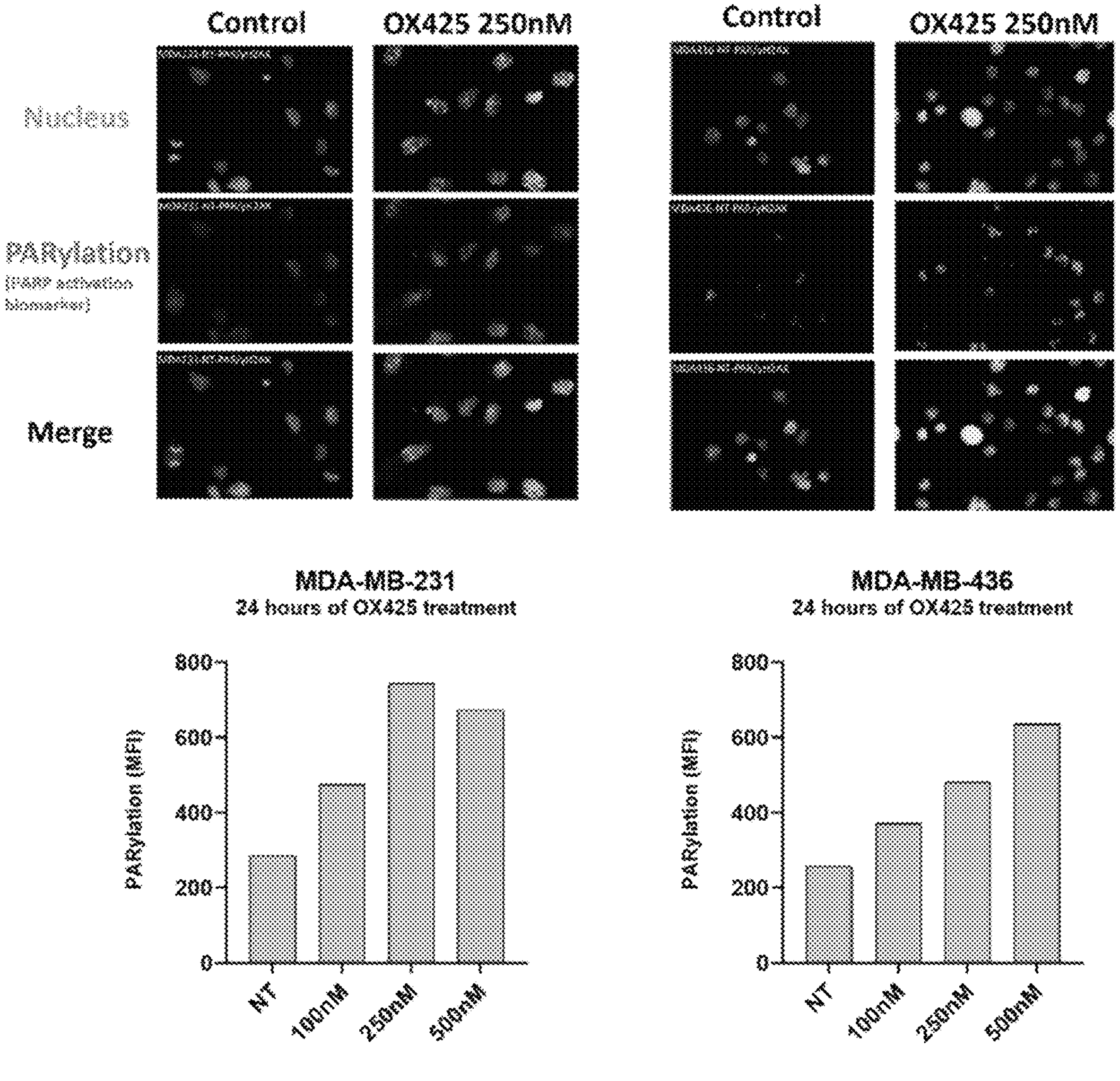

The decoy effect of OX425 was demonstrated by analyzing the interaction of Poly-(ADP-ribose) polymerase 1 (PARP1) with OX425, using a gel shift assay and examining PARP activation status in OX425-treated cells. As shown in FIG. 8A, OX425 interacts with PARP1 in a dose dependent manner and leads to hyperactivation in MDA-MB-231 and MDA-MB-436 breast cancer cell lines as assessed by immunofluorescence to detect Poly(ADP-Ribose) (PAR) polymer accumulation (PARylation, a result of PARP activation). Cells treated with OX425 showed a significant increase of PAR polymers and PARP activation starting from 24 hours after treatment (FIG. 8B).

Example 11: OX425 Demonstrates Potent Antitumor Activity in Multiple Cancer Cell Models

Materials and Methods

Cell Culture

Prostate cancer cell lines 22Rv1 and PC-3, ovarian cancer cell line OVCAR3, the triple negative breast cancer cell lines MDA-MB-231 and MDA-MB-436 from ATCC, and BC227 (gift from Institut Curie) were used as cellular models. Cells were grown according to the supplier's instructions. BC227 were cultured in Dulbecco's modified Eagle's medium DMEM (Gibco; Cat #: 31966-021) supplemented with 10% fetal bovine serum (FBS; Gibco; Cat #: 10270-106), 1% penicillin/streptomycin (Gibco; Cat #: 15140-122) and 10 μg/ml insulin (Sigma, Cat #I9278).

Drug Treatment and Measurement of Cellular Survival

MDA-MB-231 and MDA-MB-436 ($2\cdot10^3$ cells/well), 22Rv1 ($1\cdot10^3$ cells/well), PC-3, OVCAR3 and BC227 ($5\cdot10^2$ cells/well) were seeded in 96 well-plates and incubated 24 hours at 37° C. before the addition of increasing concentrations of drug for 6 days. Following drug exposure, cell survival was measured using the XTT assay (Thermo, Cat #: X12223). Briefly, the XTT solution was added directly to each well containing cell culture and the cells incubated for 4 hours at 37° C. before reading the absorbance at 485 nm using a microplate reader (VICTOR Nivo Plate Reader, Perkinelmer). Cell survival was calculated as the ratio of living treated cells to living mock-treated cells. The $IC_{50}$ (which represents the dose at which 50% of the cells are viable) was calculated by a non-linear regression model using GraphPad Prism software (version 5.04) by plotting the percentage viability against the Log of the drug concentration on each cell line.

Isolation of Human Peripheral Blood Mononuclear Cells (PBMC) and Cytotoxicity Test PBMCs isolation from whole blood (healthy donor, provide by Blood French establishment (EFS)) was performed by direct immunomagnetic negative selection with the EasySep Magnet (StemCell, Cat #19654 and Cat #18103) following the manufacturers protocol. Fresh isolated PBMC were activated and cultured at 37° C., 5% $CO_2$ for 3 days using T cell activators cocktail, supplemented with IL-2, following recommend manufacturer's instructions (StemCell, Cat #10981, #10970 and #78036.2).

For the cytotoxicity test, $2.5\times10^5$ of fully activated PBMC cells were treated with OX425 and other inhibitors (Olaparib (Clinisciences, Cat #: A10111-10), Talazoparib (Sigma, Cat #: P57204), Adavosertib (Selleckhem, Cat #: MK-1775), and Ceralasertib (Selleckhem, Cat #: AZD6738)) for 3 days. Cell viability and proliferation were assessed by counting with Acridine Orange/Propidium Iodide Stain (Logos Biosystems, Cat #F23011).

Results

Figure 9A:
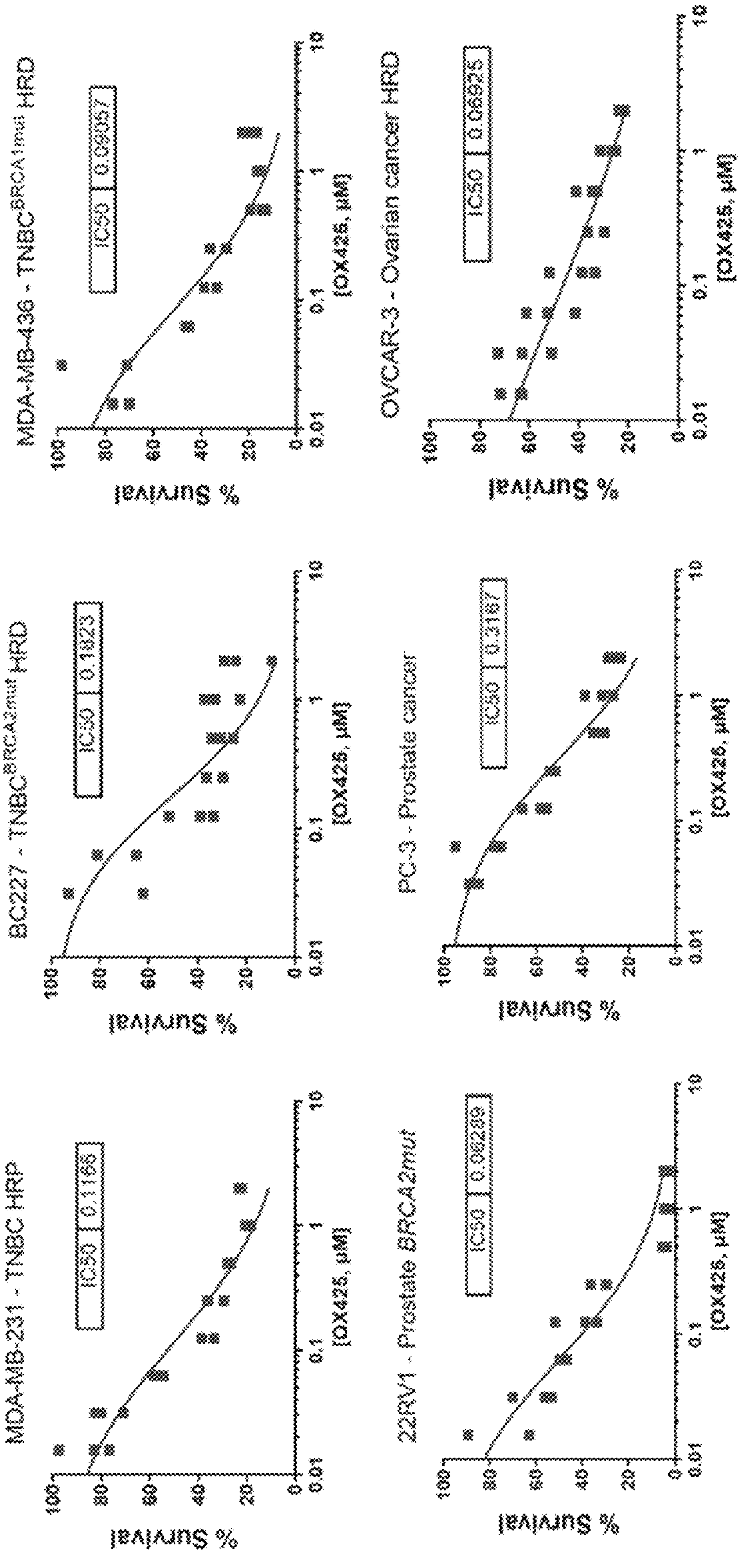
FIGS. 9A-9B. OX425 efficacy is specific to tumor cells.
Figure 9B:
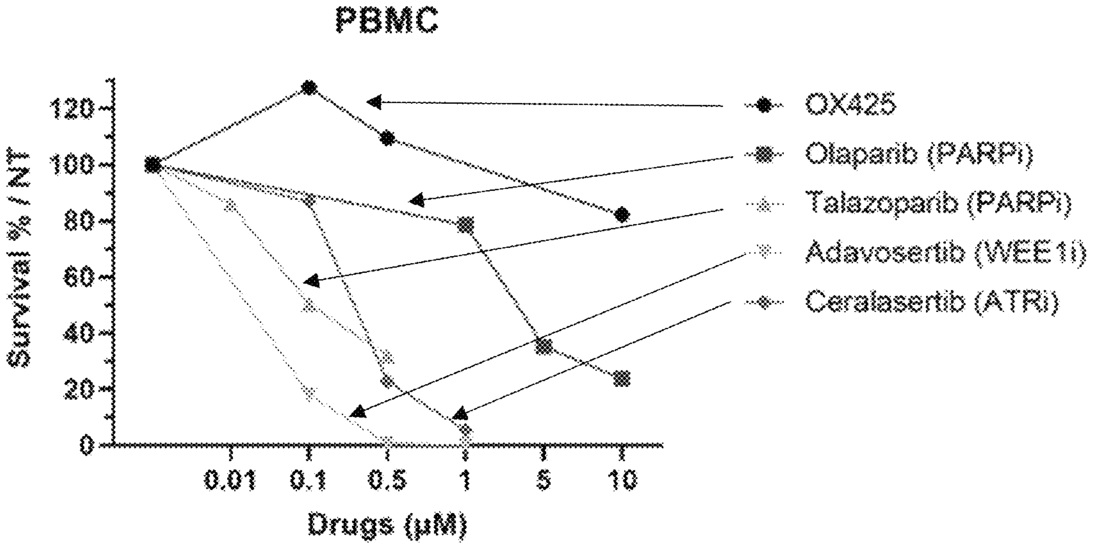

The effect of OX425 treatment on cancer cell viability was analyzed at concentrations where OX425 shows a decoy agonistic effect on PARP (trapping and hyperactivation). Different types of cancer cells (breast, ovarian, prostate) were treated with OX425 for 6 days and survival was measured using the XTT viability assay. OX425 induced a high antitumor activity with the majority of $IC_{50}$s ranging from 10 to 300 nM (FIG. 9A). Interestingly, this activity was specific to tumor cells, as no significant effect on cell viability was observed in healthy blood cells, compared to other DNA Damage Response inhibitors (WEE1, ATR or PARP inhibitors) which showed a significant toxicity toward healthy cells (FIG. 9B).

Example 12: OX425 Demonstrates Robust Anti-Tumor Activity in Homologous Recombination Deficient and Proficient Cells

Materials and Methods

Cell Culture

Prostate cancer cell lines 22Rv1 and PC-3, colorectal cancer cell lines HT29 and HCT116, ovarian cancer cell lines UWB1.289, UWB1.289 BRCA1, A2780 and OVCAR3, breast cancer cell lines MDA-MB-231, MDA-MB-436, BT-549, HCC38, HCC1143, lung cancer cell line A549 from ATCC, and BC227 (gift from Institut Curie) were used as cellular models. Cells were grown according to the supplier's instructions. BC227 were cultured in Dulbecco's modified Eagle's medium DMEM (Gibco; Cat #: 31966-021) supplemented with 10% fetal bovine serum (FBS; Gibco; Cat #: 10270-106), 1% penicillin/streptomycin (Gibco; Cat #: 15140-122) and 10 μg/ml insulin (Sigma, Cat #I9278).

Drug Treatment and Measurement of Cellular Survival

MDA-MB-231, MDA-MB-436, BT549, HCC38 and HCC1143 ($2\times10^3$ cells/well), 22Rv1, UWB1.289 and UWB1.289 BRCA1 ($1\times10^3$ cells/well), PC-3, OVCAR3, HT29, HCT116, A2780 and BC227 ($5\times10^2$ cells/well) cancer cell lines were seeded in 96 well-plates and incubated 24 hours at 37° C. before the addition of increasing concentrations of drug for 6 days. Following drug exposure, cell survival was measured using the XTT assay (Thermo, Cat #: X12223). Briefly, the XTT solution was added directly to each well containing cell culture and the cells incubated for 4 hours at 37° C. before reading the absorbance at 485 nm using a microplate reader (VICTOR Nivo Plate Reader, Perkinelmer). Cell survival was calculated as the ratio of living treated cells to living mock-treated cells. The $IC_{50}$ (which represents the dose at which 50% of the cells are viable) was calculated by a non-linear regression model using GraphPad Prism software (version 5.04) by plotting the percentage viability against the Log of the drug concentration on each cell line.

Results

Figure 10A:
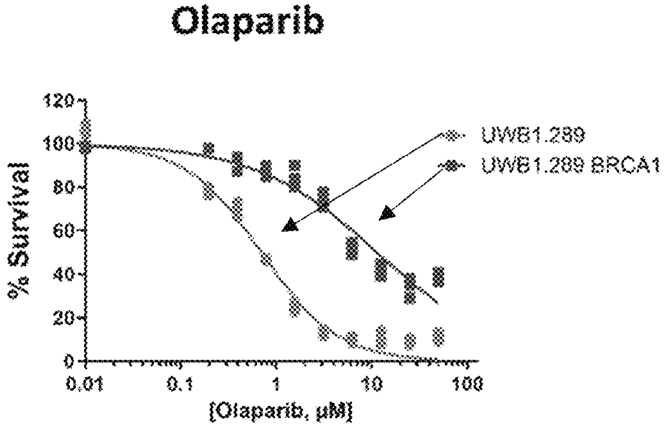
FIGS. 10A-10B. Efficacy of OX425 in HRD versus HRP cell models.
Figure 10A:
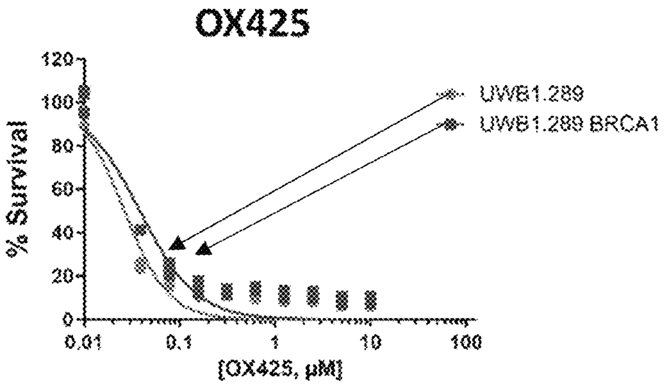
Figure 10B:
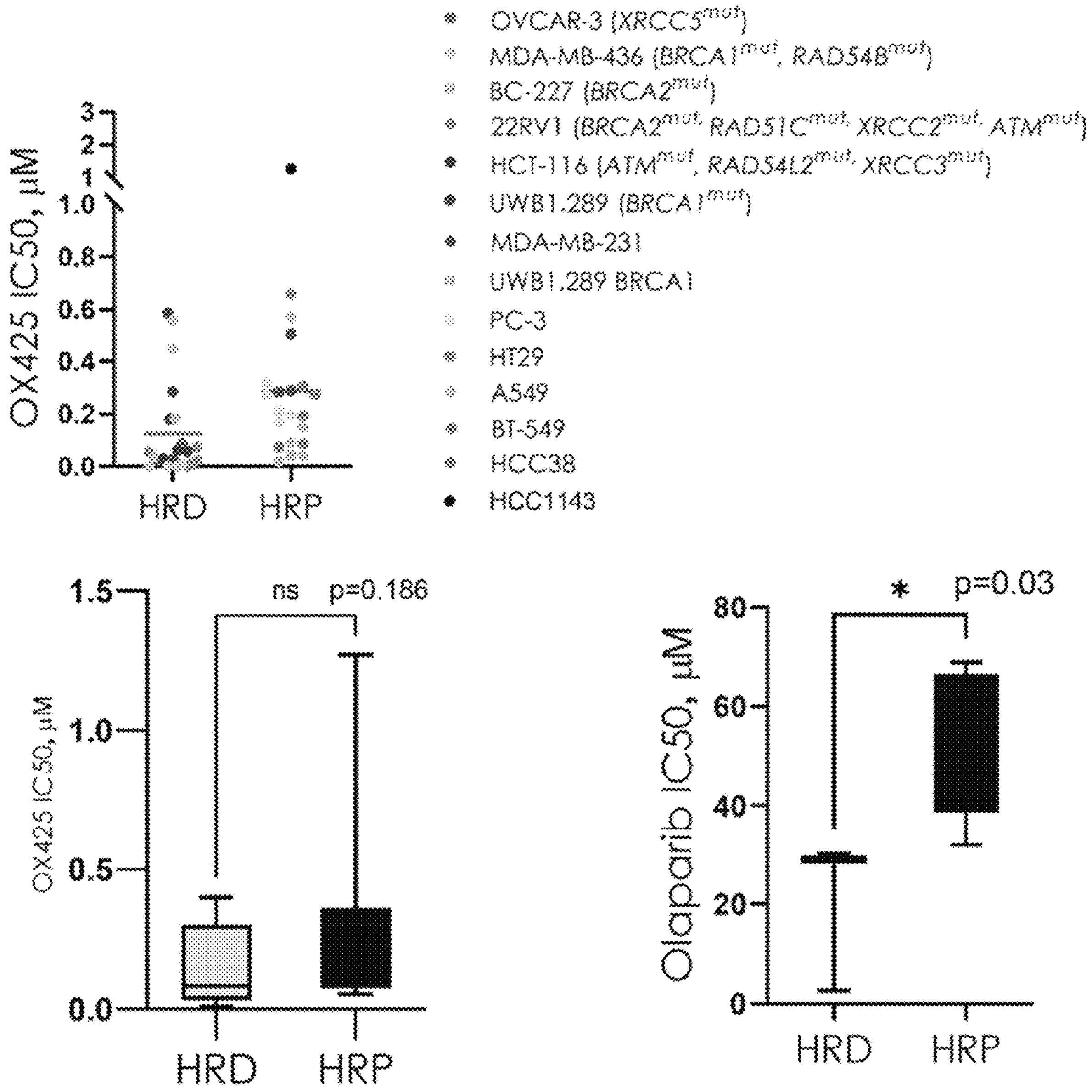

PARP inhibitors have shown significant benefits in cancer patients with deficient homologous recombination repair (HRD; induced by BRCA mutations for example). However, they show no efficacy in tumors with active or proficient repair (HRP). Since OX425 targets PARP, the inventors wanted to check if it shows a higher activity in HRD tumor cells compared to HRP cells. UWB1.289 (ovarian cancer cell line harboring a BRCA1 mutation—HRD) and it's wild type BRCA1 complemented counterpart (UWB1.289 BRCA1-HRP) were treated with olaparib or OX425 for 6 days and cell viability assessed using XTT assay. As expected olaparib showed a higher effect on survival in HRD cells in comparison to HRP cells. However, OX245 showed similar effects on cell viability irrespective of homologous recombination repair status (FIG. 10A). This was found to be the case in a variety of cell lines representing different tumor histologies i.e., compared to olaparib, which showed significantly higher efficacy in HRD cells, no significant difference was observed in sensitivity to OX425 between HRD and HRP tumor cell lines (FIG. 10B).

Example 13: OX425 Delays the Emergence of Acquired Resistance to Olaparib in Orthotopic Breast Cancer Tumors Materials and Methods Animal Model All animals were bred and maintained in specific pathogen-free facilities in accordance with guidelines. This study was complied with all relevant ethical regulations for animal testing and research and received ethical approval from the Ethics Committee. Animals had water ad libilum and were fed regular chow. Experiments were performed in nude NMRI mice (immunodeficient model, JANVIER Labs supplier). Littermate animals from different cages were randomly assigned into experimental groups and were either co-housed or systematically exposed to other groups' bedding to ensure equal exposure to common microbiota.

Triple negative breast cancer (TNBC) MDA-MB436 cells ($2\times10^6$) were suspended in mixture of L15 Leibovitz medium (Gibco, Cat #: 11570396) and BD Matrigel Matrix (BD Biosciences; Cat #: 356234) in a ratio of 1:1 and injected subcutaneously into nude NMRI mice. Olaparib (Clinisciences, Cat #: A10111-10) at the dose of 100 mg/kg on PO administration or OX425 (10 mg/kg/IP, (Axolabs; Batch #K1K2)) once per week. Animals were weighed every day during the treatment and every two days of the follow-up. The treatment efficacy was assessed in terms of the effects of the test substance on the tumor volume. Diameter of tumors will be measured two times a week. The length and width of the tumor was measured with calipers and the volume of the tumor will be estimated by the formula: Tumor_volume=(length×width$^2$)/2. Mice were euthanized at the end of the experiment; tumors were frozen for subsequent analysis.

Results

Figure 11A:
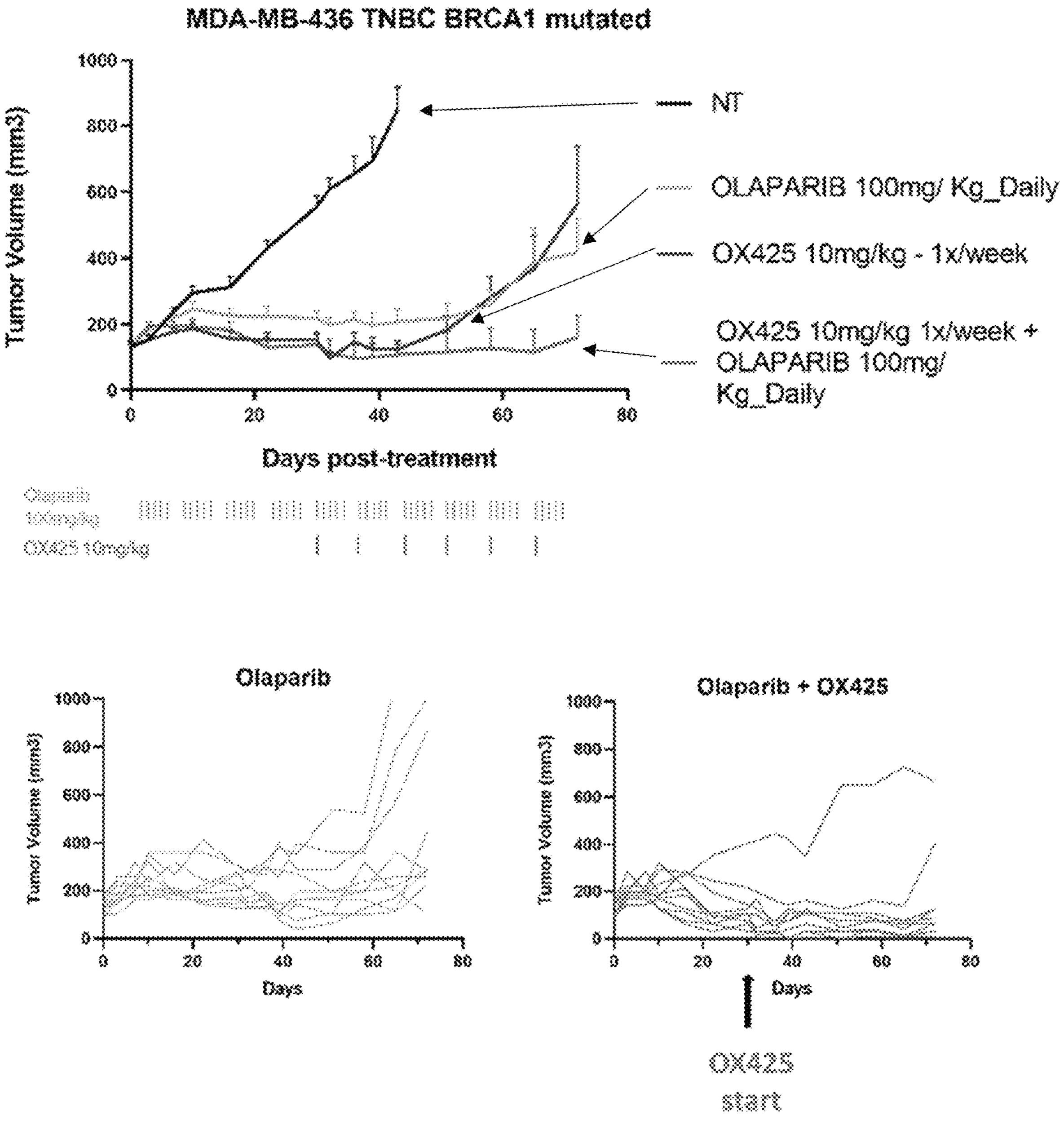
FIGS. 11A-11D; OX425 efficiency in tumors progressing under olaparib treatment.
Figure 11B:
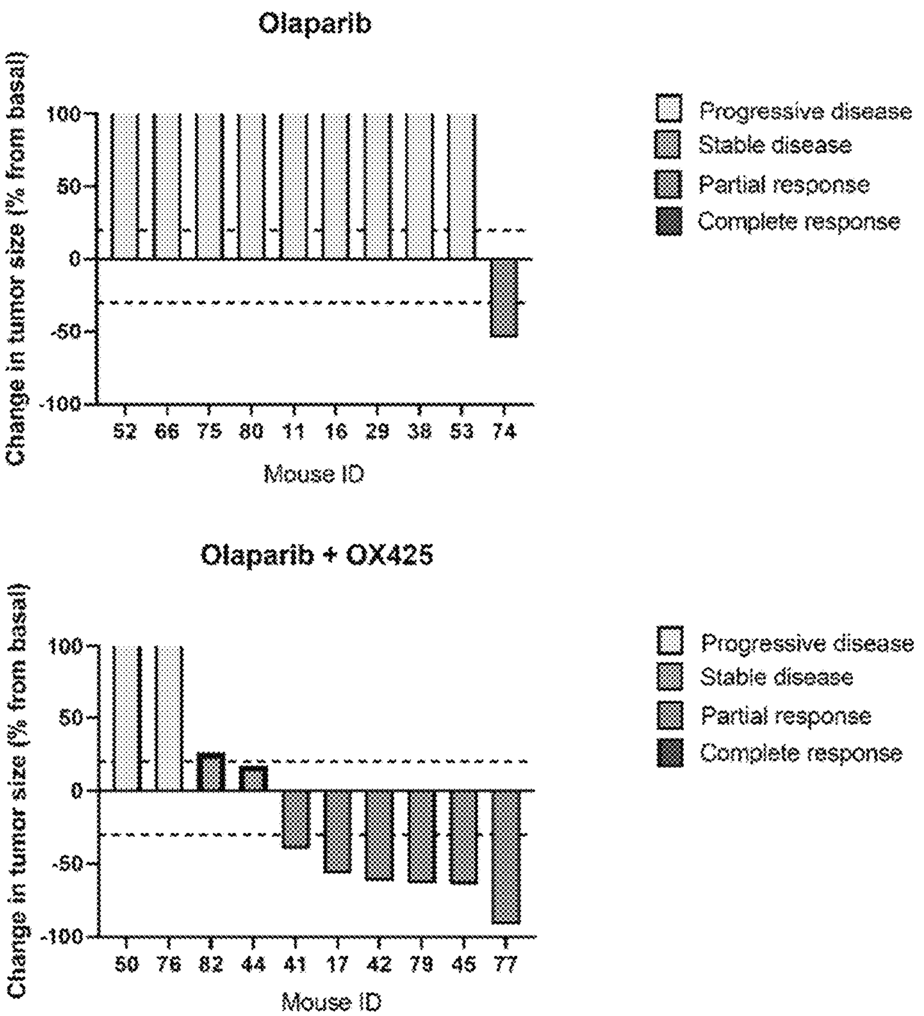
Figure 11C:
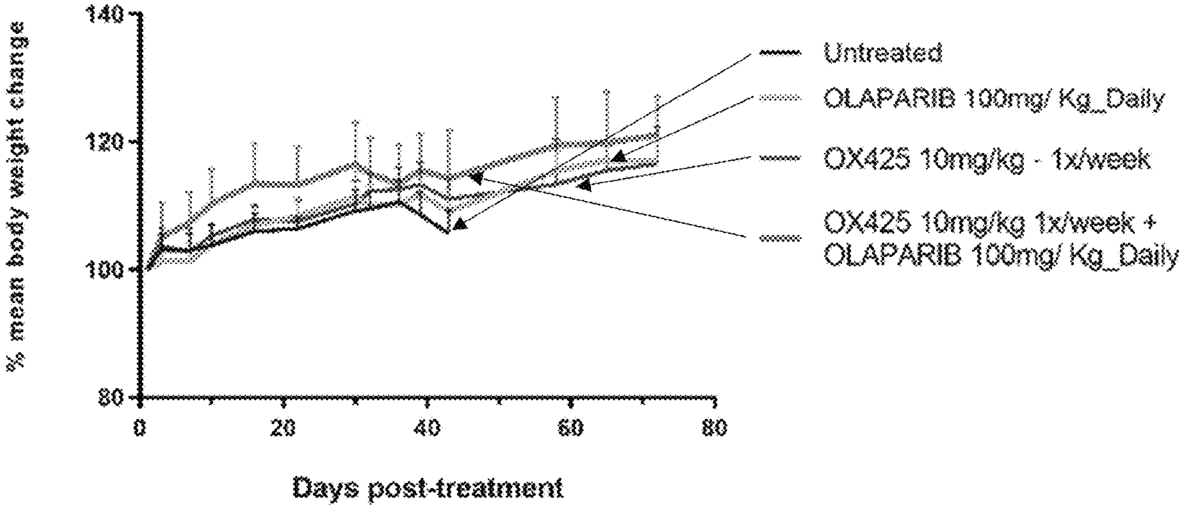
Figure 11D:
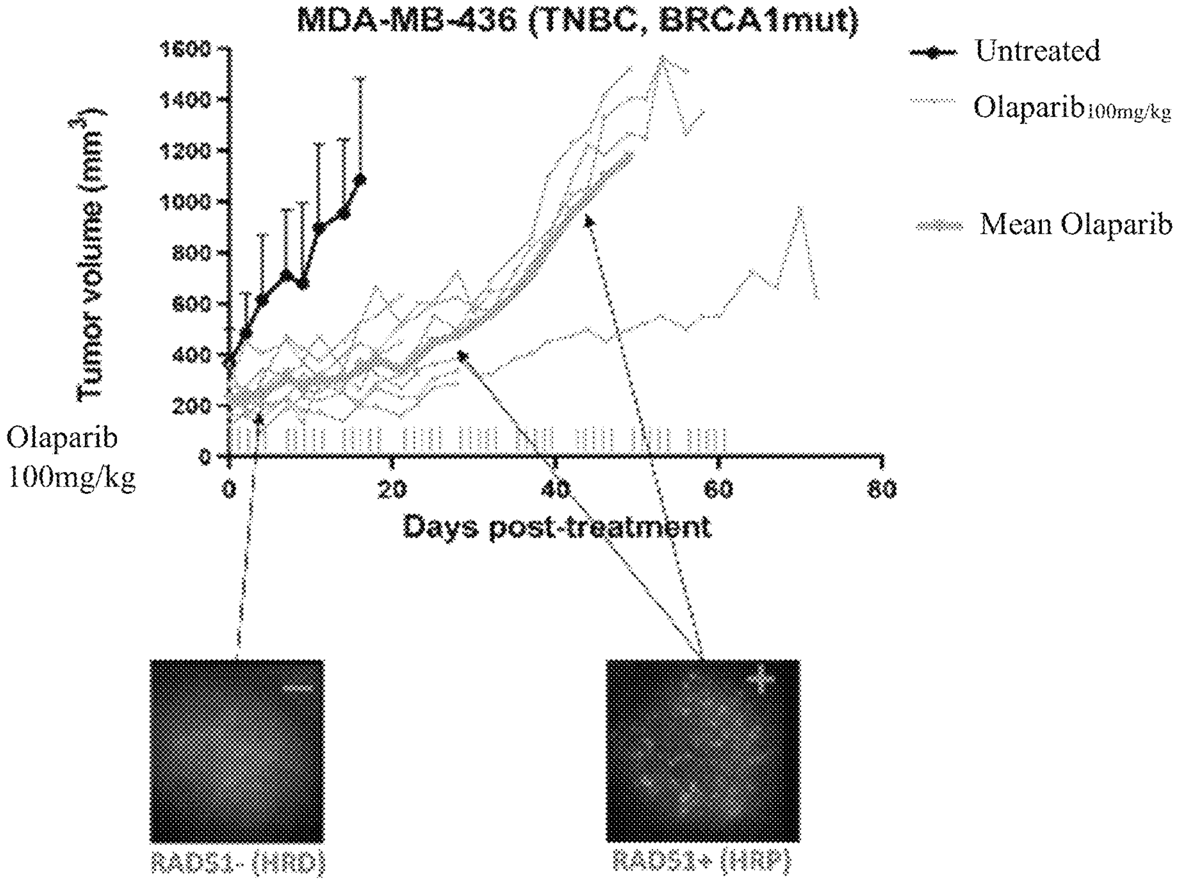

The inventors explored whether OX425 could trigger olaparib resistance reversion in vivo in the MDA-MB-436 model that is BRCA1 mutated (HRD) and initially highly sensitive to olaparib. This study consisted of four groups; control group, OX425 monotherapy group, olaparib monotherapy group and a fourth group where OX425 was added to the olaparib treatment after 30 days of monotherapy treatment with olaparib when signs of resistance appeared (FIG. 11A). Interestingly, acquired resistance to olaparib started between 30 and 60 days after treatment start, similar to in vitro models (data not shown). In fact, MDA-MB-436 CDXs were initially highly sensitive to olaparib, and then underwent a rapid growth promoting aggressive resistance to olaparib monotherapy in 90% of tumors. In a previous experiment, the inventors showed that this acquired resistance is due to the re-activation of the HR repair pathway in this model, inducing a switch from HRD-olaparib sensitive to HRP-olaparib resistant status (FIG. 11D). Introducing OX425 significantly abrogated tumor homologous recombination repair status switch and resistance to olaparib (FIG. 11B). Moreover, no apparent toxicity or loss of body weight were observed during treatments (FIG. 11C).

Example 14: OX425 Induces Cytoplasmic DNA Accumulation and Triggers an Innate Immune Response Materials and Methods Cell Culture The murine pancreatic adenocarcinoma Pan02 cells (ODS, Lot #: 8876) were maintained in RPMI 1640 (Gibco, Cat #: 11530586) supplemented with 10% FBS (FBS, Biowest; Cat #: S1810-100). Cell cultures were maintained in a humidified incubator at 37° C. with 5% $CO_2$.

Quantification of PARylation by Immunofluorescence Analysis

Cells are seeded on LabTek chambers (Fischer scientific) at a concentration of $1\times10^2$ cells and incubated at 37° C. for 24 hours. Cells are then treated with 1 or 2 μM OX425 (Axolabs; Batch #K1K2). Twenty-four hours after treatment, cells are fixed for 20 minutes in 4% paraformaldehyde/PBS 1×, permeabilized in 0.5% Triton X-100 for 10 minutes, blocked with 10% FBS (Sigma, Cat #F0685) for 15 min, and incubated with primary antibody (anti-pan-ADP-ribose binding reagent, 1/300, Millipore, Cat #MABE1016) for 1 hour at room temperature. Secondary goat anti-rabbit IgG conjugated with Alexa-488 (Molecular Probes, Cat #10453272) was used at a dilution of 1/200 for 45 minutes at room temperature, and DNA was stained with 6-diamidino-2-phenylindole (DAPI, Life Technologies; Cat #: 62248). The frequency of positive cells (showing Poly-ADP-ribose polymers, PARylation) was estimated as the number of positive cells over the total number of cells. At least 100 cells were analyzed for each sample.

Drug Treatment and Measurement of Cellular Survival

Pan02 ($1\times10^2$ cells/well) were seeded in 96 well-plates and incubated 24 hours at 37° C. before the addition of increasing concentrations of drug for 6 days. Following drug exposure, cell survival was measured using the XTT assay (Thermo, Cat #: X12223). Briefly, the XTT solution was added directly to each well containing cell culture and the cells incubated for 4 hours at 37° C. before reading the absorbance at 485 nm using a microplate reader (VICTOR Nivo Plate Reader, Perkinelmer). Cell survival was calculated as the ratio of living treated cells to living mock-treated cells. The $IC_{50}$ (which represents the dose at which 50% of the cells are viable) was calculated by a non-linear regression model using GraphPad Prism software (version 5.04) by plotting the percentage viability against the Log of the drug concentration on each cell line.

Flow Cytometry Analysis

Pan02 cells were seeded at $2\times10^5$ cells/ml and then treated for 24 hours or 48 hours with or without OX425 at 100 or 200 nM (Axolabs; Batch #K1K2). All staining, incubations were performed at 4° C. in the dark. For extracellular (PD-L1) cells were first trypsin, washed, and stained for viability using VB-Viobility (Miltenyi Biotec, 130-130-420) for 15 min in PBS. After wash, cells were stained for 30 min with PD-D1_PE (Abcam, 1/800) for 30 min in fresh PBS/BSA 0.5% buffer. Then cells were fixed and permeabilized using the Transcription Factor Staining Buffer Set (Miltenyi Biotec, 130-122-981) for 1 hour and 30 min. Before intracellular staining cells were saturated with staining buffer during 15 min. Cells were stained with STING (Cell Signaling, 13647S, 1/200) or pan-ADP-ribose binding reagent antibody (Merck, MABE1016, 1/500) for 1 hour in PBS/BSA 0.5% buffer. After washed, a secondary staining AlexaFluor647 (Abcam, ab150083, 1/2000) antibodies were used using the same buffer for 30 min. Finally, stained cells are then washed, and fluorescence intensities were acquired with a MACSQUANT8 (Miltenyi Biotec) and data were analyzed using Flowlogic software.

ELISA to Detect CCL5

Pan02 cells were treated with OX425 at 1 or 2 μM (Axolabs; Batch #K1K2) for 48 hours with or without T lymphocytes. Cell culture supernatants were then harvested and centrifuged at 1,500×g for 10 minutes to remove debris. The 96 well plate strips included with the kit (Human SimpleStep CCL5 ELISA Kit—Abcam—ab174446) are supplied ready to use. 50 μl of each supernatant were added to each well in duplicate with 50 μl of the Antibody cocktail and then, incubated for 1 h at RT on a plate shaker set to 400 rpm, after which it was washed with 1× Wash buffer PT. Then, 100 μl of TMB substrate were added to each well and incubated for 10 min in the dark on a plate shaker set to 400 rpm. 100 μl of stop solution were then added to each well for 1 minute on a plate shaker and the resulting luminescent signals were measured on a microplate reader (Enspire™ Perkin-Almer).

Animal Model

All animals were bred and maintained in specific pathogen-free facilities in accordance with guidelines. This study was complied with all relevant ethical regulations for animal testing and research and received ethical approval from the Ethics Committee. Animals had water ad libitum and were fed regular chow. Experiments were performed in nude mice. Littermate animals from different cages were randomly assigned into experimental groups and were either co-housed or systematically exposed to other groups' bedding to ensure equal exposure to common microbiota.

Pan02 cells ($2\times10^6$) were suspended in PBS (100 μl) and injected subcutaneously on the right flank of C57BL/6 mice. OX425 (25 mg/kg/IP) was administrated twice per week. Animals were weighed every day during the treatment and every two days of the follow-up. The treatment efficacy was assessed in terms of the effects of the test substance on the tumor volume. Diameter of tumors will be measured two times a week. The length and width of the tumor was measured with calipers and the volume of the tumor will be estimated by the formula: Tumor_volume=(length×width$^2$)/2. Mice were euthanized at the end of the experiment; tumors were frozen for subsequent analysis.

Tumor Dissociation and Flow Cytometry Analysis

Pan02 xenografted tumors were harvested day 6 after treatment, then tumors were finely minced and blended with the gentleMACS octo dissociator (Miltenyi Biotec) using the mouse tumor dissociation kit (Miltenyi Biotec, 130-096-730) according to the manufacturer's instructions. Dissociated tumor cells were washed with DMEM medium and red blood cells lysed with RBC lysis solution (Miltenyi Biotec, 130-094-183). Tumor-infiltrating leucocytes (TILs) were then enriched using the CD45 microbeads (Miltenyi Biotec, 130-110-618) and the MultiMACS Cell24 Separator plus (Miltenyi Biotec). Cells were counted at each step—in order to determine the % of alive CD45+ cell into the tumor.

CD45− cells, containing essentially Pan02 tumor cells, were stained with the viability dye (Viobility-VB, Miltenyi, 130-130-420, 1/100) antibody for 15 min, and then fixed and permeabilized (Miltenyi Biotec, 130-122-981), saturated, and incubated 1 hour at 4° C. with anti-Anti-pan-ADP-ribose binding reagent (Merck, MABE1016, 1/500) in PBS/BSA 0.5% staining buffer. Cells were then washed, resuspended in MACS running buffer and analyzed using MACSQUANT8 (Miltenyi Biotec) and data were analyzed using Flowlogic software.

Results

Figure 12A:
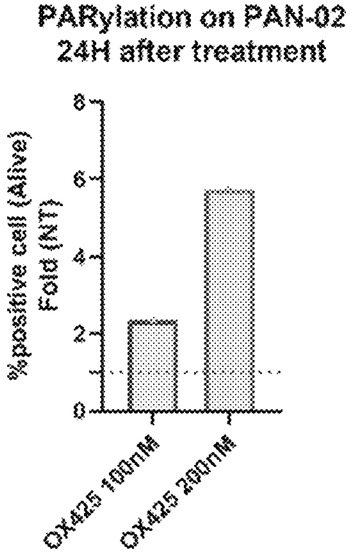
FIGS. 12A-12H. OX425 induces STING pathway activation and anti-tumor immune responses. PAN02 pancreatic cancer cells have been treated with OX425 and assessed for (FIG. 12A) PARP activation 24 hours after treatment, (FIG. 12B) sensitivity at day 6 after treatment, STING pathway activation through (FIG. 12C) STING phosphorylation, (FIG. 12D) CCL5 release and (FIG. 12E) PD-L1 overexpression, 48 hours after treatment.
Figure 12B:
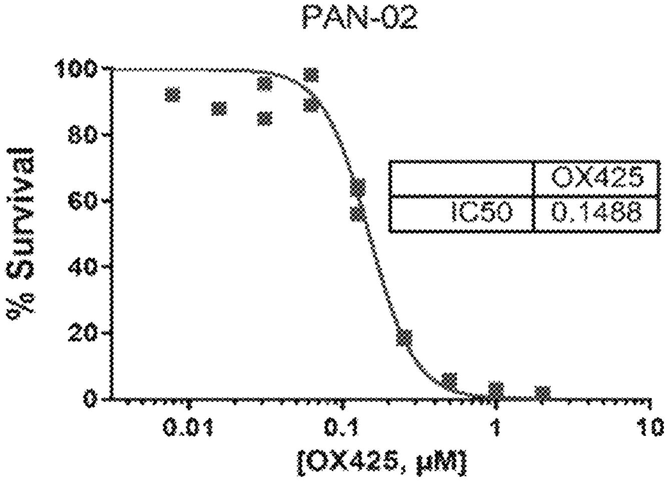
Figure 12C:
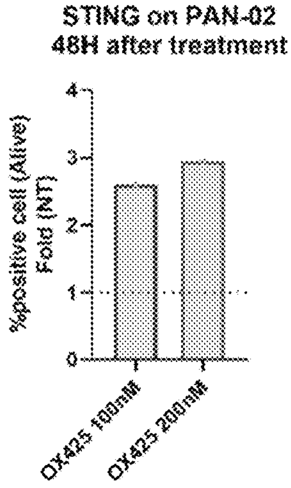
Figure 12D:
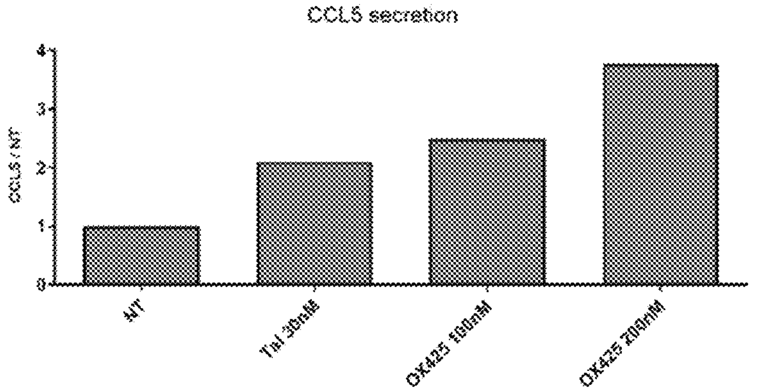
Figure 12E:
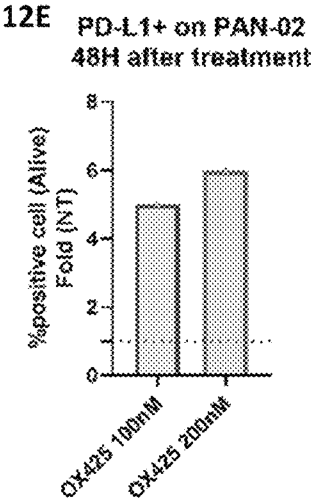

Hyper-activation of PARP proteins in OX425-treated cells was assessed by immunofluorescence analysis of PARylation (FIG. 12A). OX425-treated cells were positive for the "false" nuclear PARylation signaling, confirming the target engagement with a 2 to 6-fold increase compared to untreated cells, at the doses of 100 nM and 200 nM (FIG. 12A). To assess the effect of OX425 on cell viability, PAN02 pancreatic cancer cells were treated with increasing doses of OX425 for 6 days and the $IC_{50}$ was determined. The inventors found that under OX425 treatment PARP hyperactivation correlated with decrease in cell viability with an $IC_{50}$ of approximately 150 nM—FIG. 12B. To check if this was due to effects on cell stress and DNA repair inducing the accumulation of unrepaired DNA in the cytoplasm, the inventors studied STING pathway activation by tracking the phosphorylated and activated form of STING (pSTING) using flow cytometry. OX425 induced activation of Sting, 48 hours after treatment (FIG. 12C). To confirm the STING pathway activation, the inventors also analyzed the secretion of CCL5 chemokine in OX425-treated cell supernatant. OX425 induced an increase of CCL5 secretion 48 hours after treatment in a dose-dependent manner (3.5-fold increase at 200 nM compared to untreated cells (FIG. 12D)). Among the consequences of Sting pathway activation in tumor cells in PD-L1 (programmed death ligand 1) up-regulation, probably a feedback loop induced in tumor cells to protect against the immune system. The inventors analyzed the level of cell-surface associated with PD-L1 in OX425-treated cells. OX425 induced a 5 to 6-fold increase in membrane associated PD-L1 compared to control (FIG. 12E).

Figure 12F:
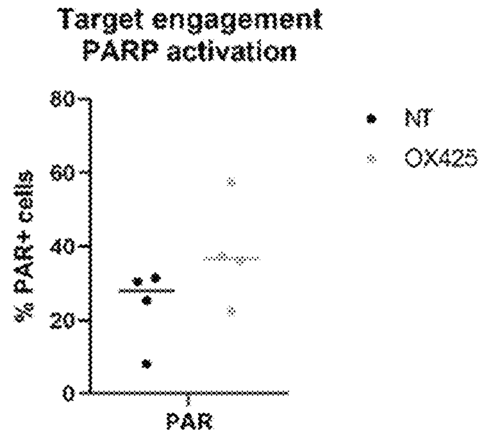
Figure 12G:
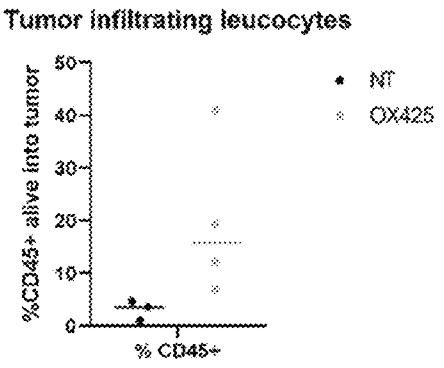
Figure 12H:
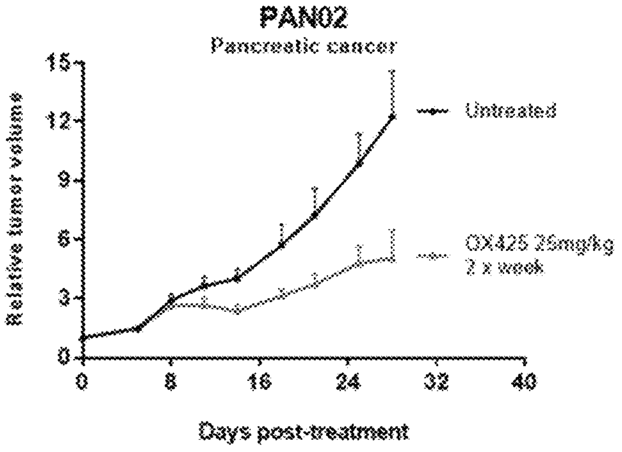

To confirm these findings in vivo, PAN02 cell-derived xenografts were treated with OX425 at 25 mg/kg, and target engagement as well as tumor infiltrating leucocytes (TILs—as a result of STING pathway activation) were analyzed 48 hours after the last administration by flow cytometry. OX425-treated tumors showed tendency in PARP activation (FIG. 12F). However, a significant increase of CD45+ TIL infiltration was observed (FIG. 12G), confirming the OX425-induced immune effects that are known to mediate antitumor actions. In line with these observations, OX425 monotherapy was associated with a significant delay of tumor growth in this xenograft model (FIG. 12H). Taken together, these results demonstrate OX425 induces the innate immune response and Sting pathway activation through the accumulation of cytoplasmic DNA fragments and cytokine secretion.

Example 15: OX425 Increases Immune Cells Infiltration in the Tumor Microenvironment

Materials and Methods

Animal Model

All animals were bred and maintained in specific pathogen-free facilities in accordance with guidelines. This study was complied with all relevant ethical regulations for animal testing and research and received ethical approval from the Ethics Committee. Animals had water ad libitum and were fed regular chow. Experiments were performed in BALB/c mice. Littermate animals from different cages were randomly assigned into experimental groups and were either co-housed or systematically exposed to other groups' bedding to ensure equal exposure to common muicrobiota.

EMT6 cells ($0.5\times10^6$) were suspended in were suspended in mixture of Waymouth's MB 752/1 medium (Sigma, Cat #: W1625) with 2 mM L-glutamine and BD Matrigel Matrix (BD Biosciences; Cat #: 356234) in a ratio of 1:1 and injected into BALB/c mice (orthotopic model). OX425 (25 mg/kg or 100 mg/kg/IP, (Axolabs; Batch #K1K2)) was administrated three times for 6 days. Animals were weighed every day during the treatment and every two days of the follow-up. The treatment efficacy was assessed in terms of the effects of the test substance on the tumor volume. Diameter of tumors will be measured two times a week. The length and width of the tumor was measured with calipers and the volume of the tumor will be estimated by the formula: Tumor_volume=(length$\times$width$^2$)/2. Mice were euthanized at the end of the experiment; tumors were frozen for subsequent analysis.

Tumor Dissociation and Flow Cytometry Analysis.

EMT6 tumors were harvested 24 hours after the last treatment, then tumors were finely minced and blended with the gentleMACS octo dissociator (Miltenyi Biotec) using the mouse tumor dissociation kit (Miltenyi Biotec, 130-096-730) according to the manufacturer's instructions. Dissociated tumor cells were washed with DMEM medium and red blood cells lysed with RBC lysis solution (Miltenyi Biotec, 130-094-183). Tumor-infiltrating leucocytes (TILs) were then enriched using the CD45 microbeads (Miltenyi Biotec, 130-110-618) and the MultiMACS Cell24 Separator plus (Miltenyi Biotec). Cells were counted at each step—in order to determine the % of TILs.

CD45+ cells were resuspended in PBS and stained with the antibody panel (Viobility dye, CD3-APC, CD8a-PE-Vio770, CD4-APC-Vio770, and CD49b-VioBright515, Miltenyi Biotec) or corresponding isotypes during 30 min at 4° C. in PBS/BSA 0.5%. Compensations were performed using monostained and isotypes. Cells were then washed, resuspended in MACS running buffer and analyzed using MACSQUANT8 (Miltenyi Biotec), data were analyzed using Flowlogic software, finally statistical analysis were done with GraphPad Prism software (version 5.04).

Results

Figure 13A:
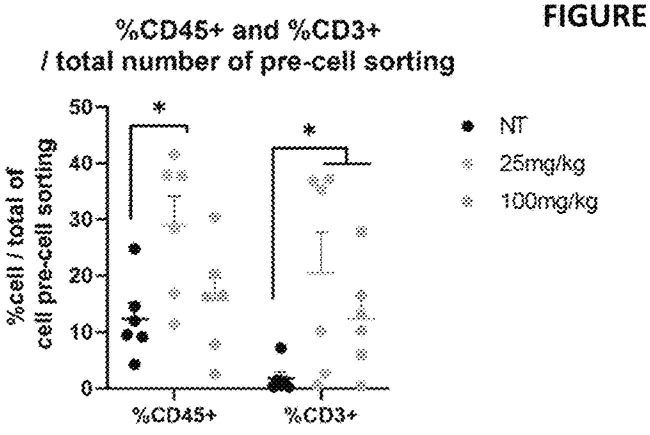
FIGS. 13A-13C. OX425 increases immune infiltration in the tumor microenvironment. EMT6 breast cancer cell-derived xenografts were treated with OX425 at 25 or 100 mg/kg, at day 0, 3 and 5, and tumors harvested at day 6 for tumor microenvironment analysis. % of different immune populations (CD3, CD4, CD8, CD4+CD49b+) was analyzed by flow cytometry after tumor dissociation and CD45+ cell sorting.
Figure 13C:
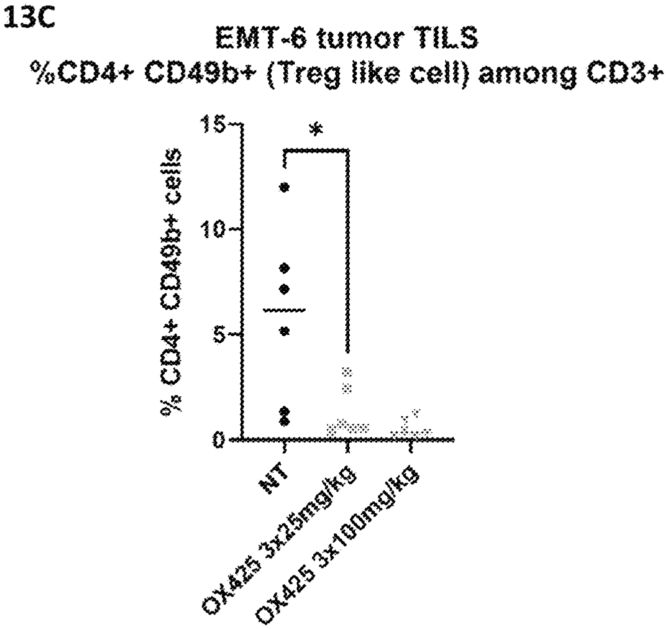
Figure 13B:
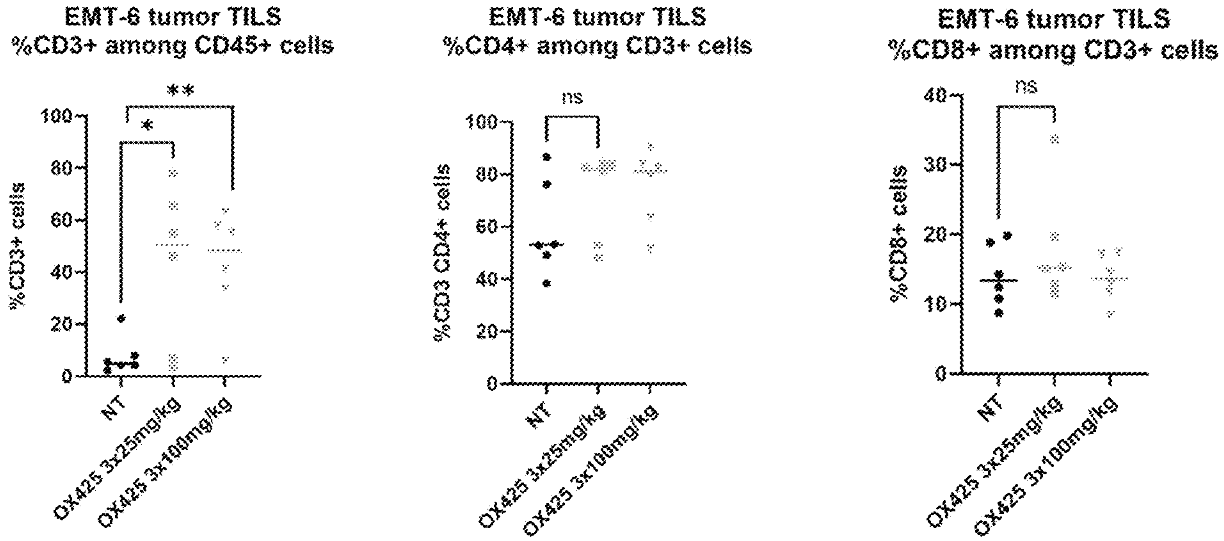

To further investigate the immune-mediated effects of OX425, the inventors evaluated the efficacy of OX425 in syngeneic breast tumor EMT6 xenografts. EMT6 cell-derived xenografts were treated with vehicle or OX425 at different doses (25 and 100 mg/kg—three administrations at Day 0, 3 and 5), and tumor tissue was harvested on Day 6 after the last treatment. To confirm OX425's effects on anti-tumor immune responses, they analyzed the immune components of the tumor microenvironment. Flow cytometric analysis of tumor-infiltrating leucocytes (TILs; CD45+ cells) showed that OX425 significantly increased total TILs as early as 6 days after treatment start, as measured by CD45 staining (FIG. 13A). The proportions of T cells (CD3+) among CD45+ cells were significantly increased in response to OX425 treatment (FIG. 13B). OX425 not only induced an increase of T cells tumor infiltration but also triggered a decrease of T regulatory cells (CD3−, CD4+, CD49b+) (FIG. 13C). All these effects were observed even at the low dose of 25 mg/kg.

Taken together, these results demonstrate an effective OX425-induced PARP and STING pathway activation in tumors, which increases innate and adaptive immune cells recruitment and boosts a productive anti-tumor immune response.

Example 16: Immunotherapeutic Activity of OX425 Against PD-1 Resistant HR+HER2-Breast Cancer

Materials and Methods

Animal Model

Mice

C57BL/6 mice of 6-15 weeks of age were employed. Mice were maintained in standard specific pathogen-free (SPF) housing conditions (20±2° C., 50±5% humidity, 12 h-12 h light/dark cycles, food and water ad libitum), unless specified as per study design. Animal experiments followed the Federation of European Laboratory Animal Science Association (FELASA) guidelines, were in compliance with the EU Directive 63/2010 (protocol 2012_034A) and were approved by institutional ethical committees for animal experimentation at Gustave Roussy (no. 2016031417225217), Centre de Recherche des Cordeliers (no. 2016041518388910), and Weill Cornell Medical College (no. 2017-0007 and 2018-0002). WT C57BL/6 were obtained from Taconic Farms. In all experiments, mice were routinely monitored for tumor growth and euthanized when tumor surface reached 200-250 mm2 (ethical endpoint), or in the presence of overt signs of distress (e.g., hunching, anorexia, tumor ulceration).

Oncogenesis

Fifty mg slow-release (90 days) MPA pellets (#NP-161, Innovative Research of America) were implanted subcutaneously by surgery into 6-9 week old female mice (day 0). Mice were administered 200 μL of a 5 mg mL-1 7,12-dimethylbenz[a]anthracene (DMBA; #D3254, from Millipore Sigma) solution in corn oil (#C8267, Millipore Sigma), by oral gavage once a week on weeks 1, 2, 3, 5, 6, and 7 after implantation of the MPA pellet.

Treatment

OX425 (0.1 mg or 0.5 mg—equivalent to 5 or 25 mg/kg/IP) was administrated once (1×) or twice (2×) per week. Animals were weighed every day during the treatment and every two days of the follow-up. The treatment efficacy was assessed in terms of the effects of the test substance on the tumor volume. Diameter of tumors will be measured two times a week. The length and width of the tumor was measured with calipers and the volume of the tumor will be estimated by the formula: Tumor_volume=(length$\times$width$^2$)/2. Mice were euthanized at the end of the experiment; tumors were frozen for subsequent analysis.

Results

Hormone receptor (HR)$^+$ breast cancer is a cold tumor that responds poorly to immune checkpoint blockers targeting PD-1, calling for the development of therapeutic strategies that inflame the HR$^+$ tumor microenvironment to restore PD-1 sensitivity. A unique endogenous mouse model that recapitulates key immunobiological features of human HR$^+$HER2$^-$ breast cancer was developed, as driven by subcutaneous, slow-release medroxyprogesterone acetate (MPA) pellets combined with 7,12-dimethylbenz[a]anthracene (DMBA) gavage, to investigate the therapeutic efficacy of OX425 delivered intraperitoneally once or twice per week at 5 or 25 mg/kg, optionally combined with a mouse PD-1 inhibitor (delivered intraperitoneally in 2 doses of 200 µg/mouse 3 days apart from each other). Tumor growth, mouse-adapted RECIST score assessments, progression-free survival, overall survival, and other clinically relevant parameters were monitored until ethical endpoint.

Figure 14:
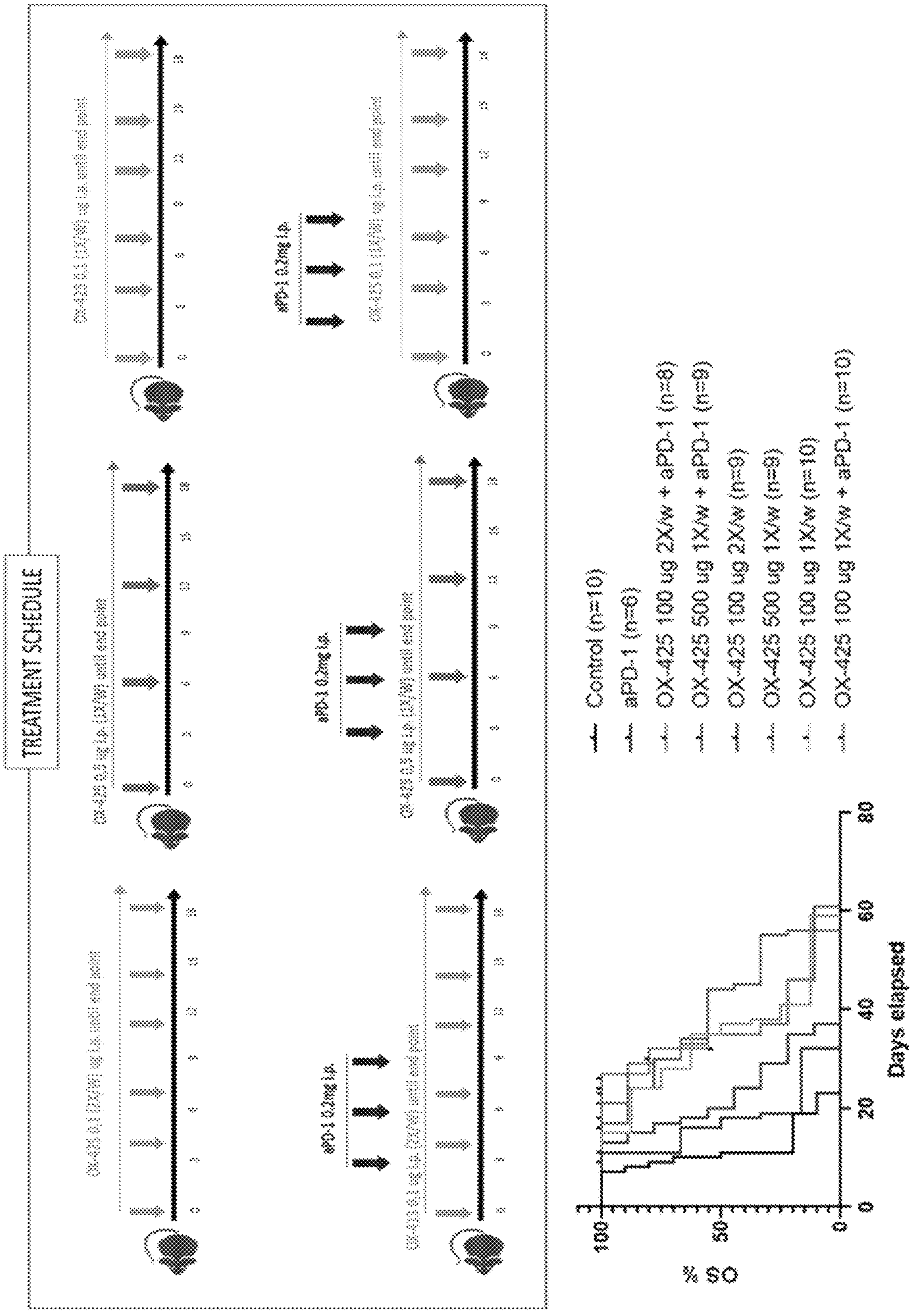
FIG. 14. OX425 alone or combined to PD-1 blockage mediates single-agent immunotherapeutic activity in PD-1-resistant HR+HER2− breast cancer models. MPA/DMBA-driven mammary tumors were treated with OX425 at 25 or 5 mg/kg, two times per week (2×/w) or once weekly (1×/w), and tumor growth and animal survival were assessed. Statistical analyses were also performed on animal survival. ns, not significant.

As shown in FIG. 14 and in the following Table, OX425 at the highest dosing schedule (25 mg/kg twice weekly) was associated with weight loss across treated mice (irrespective of PD-1 blockage) and premature mortality in 10% of the mice, calling for dose reduction to 5 mg/kg twice weekly. At all other administration schedules, OX425 was well tolerated, effective at controlling tumor growth and extending overall survival in mice bearing MPA/DMBA-driven carcinomas (which are intrinsically resistant to PD-1, similar to HR$^+$ breast cancer in women). Blocking PD-1 increased the therapeutic activity of OX425 when delivered twice weekly at 5 mg/kg as it inhibited the development of secondary tumors. Together, these results showed that OX425 at doses <25 mg/kg twice weekly is well tolerated in mice and mediates single-agent immunotherapeutic activity in models of PD-1-resistant HR$^+$HER2$^-$ breast cancer, with a potential for synergy with PD-1.

| Treatment | Median survival (days) | Vs control |
|---|---|---|
| control | 10.5 | |
| aPD-1 | 17 | Ns: 0.1280 |
| OX-425 100 µg 2x/w + aPD-1 | 36 | <0.0001 |
| OX-425 500 µg 1x/w + aPD-1 | 44 | <0.0001 |
| OX-425 100 µg 2x/w | 20 | <0.0001 |
| OX-425 500 µg 1x/w | 35 | 0.0033 |
| OX-425 100 µg 1x/w | 38 | <0.0001 |
| OX-425 100 µg 1x/w + aPD-1 | 40.5 | <0.0001 |

Example 17: OX425 Displays Higher Anti-Tumor Efficacy Compared to OX401

Materials and Methods

Cell Culture

Breast cancer cell lines MDA-MB-231, BT549 and HCC38 from ATCC, were used as cellular models. Cells were grown according to the supplier's instructions in complete medium supplemented with 10% fetal bovine serum (FBS) and maintained in a humidified atmosphere at 37° C. and 0% $CO_2$.

Drug Treatment and Measurement of Cellular Survival

Cells were seeded in 96 well-plates ($2 \cdot 10^3$ cells/well) and incubated 24 hours at 37° C. before the addition of increasing concentrations of drug for 6 days. Following drug exposure, cell survival was measured using the XTT assay (Thermo, Cat #: X12223). Briefly, the XTT solution was added directly to each well containing cell culture and the cells incubated for 4 hours at 37° C. before reading the absorbance at 485 nm using a microplate reader (VICTOR Nivo Plate Reader, Perkinelmer). Cell survival was calculated as the ratio of living treated cells to living mock-treated cells. The $IC_{50}$ (which represents the dose at which 50% of the cells are viable) was calculated by a non-linear regression model using GraphPad Prism software (version 5.04) by plotting the percentage viability against the Log of the drug concentration on each cell line.

Results

Figure 15:
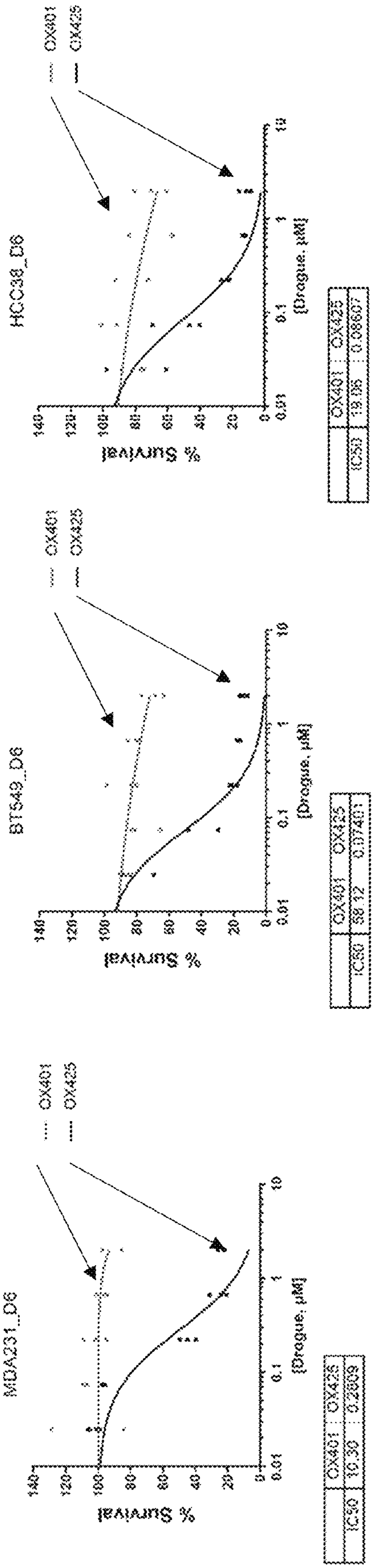
FIG. 15. OX425 displays higher anti-tumor activity. Sensitivity to increasing doses of OX425 (up to 2 μM) of different tumor cell lines with different homologous recombination (HR) repair status (HR deficient, HRD, or HR proficient, HRP) was assessed using XTT assay at day 6 after treatment. $IC_{50}$s were calculated using GraphPadPrism software.

To assess the anti-tumor efficacy of OX425, MDA-MB-231, BT549 and HCC38 breast cancer cells were treated with increasing doses of Ox425 or OX401 during 6 days to estimates the $IC_{50}$s (median inhibitory concentration). Interestingly, OX425 showed an $IC_{50}$ significantly lower than OX401 (FIG. 15).

The invention claimed is:

1. A conjugated nucleic acid molecule, wherein the nucleic acid molecule is

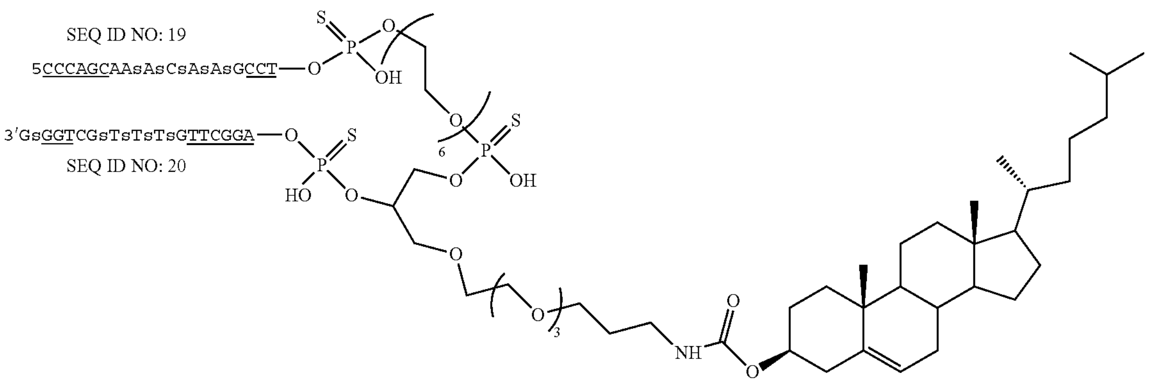

wherein internucleotide linkages “s” refer to phosphorothioate internucleotide linkages; and wherein the underlined 2'-modified nucleotides are 2'-deoxy-2-fluoroarabinonucleotides (FANA).

2. A pharmaceutical composition or a veterinary composition comprising a conjugated nucleic acid molecule according to claim 1, and optionally further comprising an additional therapeutic agent selected from an immunomodulator, an immune checkpoint inhibitor (ICI), a T-cell-based cancer immunotherapy, adoptive cell transfer (ACT), genetically modified T-cells, engineered T-cells, chimeric antigen receptor cells (CAR-T cells), a conventional chemotherapeutic agent, radiotherapeutic agent, anti-angiogenic agent, or a targeted immunotoxin.

3. The pharmaceutical composition or veterinary composition according to claim 2, further comprising an immune checkpoint inhibitor (ICI) selected from an inhibitor of the PD-1/PD-L1 pathway or an anti-PD-1 antibody.

4. The pharmaceutical composition or veterinary composition according to claim 2, wherein the anti-PD-1 antibody is spartalizumab, nivolumab, pembrolizumab, pidilizumab, cemiplimab, dostarlimab tislelizumab, camrelizumab, sintilimab, toripalimab, or retifanlimab.

5. A method for treating a cancer in a subject in need thereof comprising administering a therapeutically effective amount of a conjugated nucleic acid molecule according to claim 1.

6. The method according to claim 5, wherein the cancer is selected from leukemia, lymphoma, sarcoma, melanoma, and cancers of the head and neck, kidney, ovary, pancreas, prostate, thyroid, lung, esophagus, breast, bladder, brain, colorectum, liver, endometrium or cervix.

7. The method according to claim 5, wherein the method further comprises administering an effective amount of an additional therapeutic agent selected from an immunomodulator, an immune checkpoint inhibitor (ICI), a T-cell-based cancer immunotherapy, adoptive cell transfer (ACT), genetically modified T-cells, engineered T-cells, chimeric antigen receptor cells (CAR-T cells), a conventional chemotherapeutic agent, radiotherapeutic agent, anti-angiogenic agent, or a targeted immunotoxin.

8. The method according to claim 6, wherein the method further comprises administering an effective amount of an additional therapeutic agents elected from an immunomodulator, an immune checkpoint inhibitor (ICI), a T-cell-based cancer immunotherapy, adoptive cell transfer (ACT), genetically modified T-cells, engineered T-cells, chimeric antigen receptor cells (CAR-T cells), a conventional chemotherapeutic agent, radiotherapeutic agent, anti-angiogenic agent, or a targeted immunotoxin.

9. The method according to claim 7, wherein the immune checkpoint inhibitor (ICI) is selected from an inhibitor of the PD-1/PD-L1 pathway or an anti-PD-1 antibody.

10. The method according to claim 9, wherein the anti-PD-1 antibody is spartalizumab, nivolumab, pembrolizumab, pidilizumab, cemiplimab, dostarlimab, tislelizumab camrelizumab, sintilimab, toripalimab, or retifanlimab.

11. The method according to claim 8, wherein the immune checkpoint inhibitor (ICI) is selected from an inhibitor of the PD-1/PD-L1 pathway or an anti-PD-1 antibody.

12. The method according to claim 11, wherein the anti-PD-1 antibody is spartalizumab, nivolumab, pembrolizumab pidilizumab, cemiplimab, dostarlimab tislelizumab, camrelizumab, sintilimab, toripalimab, or retifanlimab.

13. The method according to claim 5, wherein the cancer is a homologous recombination deficient tumor.

14. The method according to claim 5, wherein the cancer is a homologous recombination proficient tumor.

15. The method according to claim 5, wherein the cancer is selected from leukemia, lymphoma, and cancers of ovary, prostate, breast, colon, endometrium or lung.

16. The method according to claim 5, wherein the cancer is selected from cancers of ovary, prostate or breast.

* * * * *

SEQUENCE LISTING

```
Sequence total quantity: 20
SEQ ID NO: 1              moltype = DNA  length = 17
FEATURE                   Location/Qualifiers
misc_feature              1..17
                          note = first strand of the double stranded nucleic acid
misc_feature              1
                          note = N is an inverted nucleotide, present or absent
modified_base             2..7
                          mod_base = OTHER
                          note = 2' modified nucleotide
misc_feature              9..14
                          note = phosphorothioate internucleotide linkages
modified_base             15..17
                          mod_base = OTHER
                          note = 2' modified nucleotide
misc_difference           17
                          note = N is T or U
misc_feature              17
                          note = loop
source                    1..17
                          mol_type = other DNA
                          organism = synthetic construct
```

```
SEQUENCE: 1
ncccagcaaa caagccn                                                    17

SEQ ID NO: 2           moltype = DNA  length = 17
FEATURE                Location/Qualifiers
misc_feature           1..17
                       note = second strand of the double stranded nucleic acid
misc_feature           1
                       note = loop
modified_base          1..6
                       mod_base = OTHER
                       note = 2'-modified nucleotide
misc_difference        5..6
                       note = N is T or U
misc_feature           7..11
                       note = phosphorothioate internucleotide linkages
misc_difference        13
                       note = N is T or U
modified_base          13..15
                       mod_base = OTHER
                       note = 2'-modified nucleotide
misc_feature           15..16
                       note = phosphorothioate internucleotide linkage
misc_feature           17
                       note = N is an inverted nucleotide, present or absent
source                 1..17
                       mol_type = other DNA
                       organism = synthetic construct
SEQUENCE: 2
aggcnngttt gcngggn                                                    17

SEQ ID NO: 3           moltype = DNA  length = 17
FEATURE                Location/Qualifiers
misc_feature           1..17
                       note = first strand of the double stranded nucleic acid
misc_feature           1
                       note = N is an inverted nucleotide
modified_base          2..7
                       mod_base = OTHER
                       note = 2' modified nucleotide
misc_feature           9..17
                       note = phosphorothioate internucleotide linkages
modified_base          15..17
                       mod_base = OTHER
                       note = 2' modified nucleotide
misc_feature           17
                       note = loop
source                 1..17
                       mol_type = other DNA
                       organism = synthetic construct
SEQUENCE: 3
ncccagcaaa caagcct                                                    17

SEQ ID NO: 4           moltype = DNA  length = 17
FEATURE                Location/Qualifiers
misc_feature           1..17
                       note = second strand of the double stranded nucleic acid
misc_feature           1
                       note = loop
modified_base          1..6
                       mod_base = OTHER
                       note = 2' modified nucleotide
misc_feature           7..11
                       note = phosphorothioate internucleotide linkages
modified_base          13..15
                       mod_base = OTHER
                       note = 2' modified nucleotide
misc_feature           15..16
                       note = phosphorothioate internucleotide linkage
misc_feature           17
                       note = N is an inverted nucleotide
source                 1..17
                       mol_type = other DNA
                       organism = synthetic construct
SEQUENCE: 4
aggcttgttt gctgggn                                                    17

SEQ ID NO: 5           moltype = DNA  length = 17
FEATURE                Location/Qualifiers
```

-continued

```
misc_feature          1..17
                      note = first strand of the double stranded nucleic acid
misc_feature          1
                      note = N is an inverted nucleotide, present or absent
modified_base         2..7
                      mod_base = OTHER
                      note = 2' modified nucleotide
misc_feature          9..14
                      note = phosphorothioate internucleotide linkages
modified_base         15..17
                      mod_base = OTHER
                      note = 2' modified nucleotide
misc_feature          17
                      note = loop
source                1..17
                      mol_type = other DNA
                      organism = synthetic construct
misc_difference       17
                      note = t is u
SEQUENCE: 5
ncccagcaaa caagcct                                            17

SEQ ID NO: 6          moltype = DNA  length = 17
FEATURE               Location/Qualifiers
misc_feature          1..17
                      note = second strand of the double stranded nucleic acid
misc_feature          1
                      note = loop
modified_base         1..6
                      mod_base = OTHER
                      note = 2' modified nucleotide
misc_feature          7..11
                      note = phosphorothioate internucleotide linkages
modified_base         13..15
                      mod_base = OTHER
                      note = 2' modified nucleotide
misc_feature          15..16
                      note = phosphorothioate internucleotide linkage
misc_feature          17
                      note = N is an inverted nucleotide, present or absent
source                1..17
                      mol_type = other DNA
                      organism = synthetic construct
misc_difference       5..6
                      note = t is u
misc_feature          13
                      note = t is u
SEQUENCE: 6
aggcttgttt gctgggn                                            17

SEQ ID NO: 7          moltype = DNA  length = 16
FEATURE               Location/Qualifiers
misc_feature          1..16
                      note = first strand of the double stranded nucleic acid
modified_base         1..6
                      mod_base = OTHER
                      note = 2' OMe nucleotide
misc_feature          8..13
                      note = phosphorothioate internucleotide linkages
modified_base         14..16
                      mod_base = OTHER
                      note = 2' OMe nucleotide
misc_feature          16
                      note = loop
source                1..16
                      mol_type = other DNA
                      organism = synthetic construct
misc_difference       16
                      note = t is u
SEQUENCE: 7
cccagcaaac aagcct                                             16

SEQ ID NO: 8          moltype = DNA  length = 16
FEATURE               Location/Qualifiers
misc_feature          1..16
                      note = second strand of the double stranded nucleic acid
misc_feature          1
                      note = loop
modified_base         1..6
```

```
                        mod_base = OTHER
                        note = 2'-OMe nucleotide
misc_feature            7..11
                        note = phosphorothioate internucleotide linkages
modified_base           13..15
                        mod_base = OTHER
                        note = 2'-OMe nucleotide
misc_feature            15..16
                        note = phosphorothioate internucleotide linkage
source                  1..16
                        mol_type = other DNA
                        organism = synthetic construct
misc_difference         5..6
                        note = t is u
misc_difference         13
                        note = t is u
SEQUENCE: 8
aggcttgttt gctggg                                                   16

SEQ ID NO: 9            moltype = DNA  length = 17
FEATURE                 Location/Qualifiers
misc_feature            1..17
                        note = first strand of the double stranded nucleic acid
misc_feature            1
                        note = inverted T
modified_base           2..7
                        mod_base = OTHER
                        note = F-ANA nucleotide
misc_feature            9..14
                        note = phosphorothioate internucleotide linkages
modified_base           15..17
                        mod_base = OTHER
                        note = F-ANA nucleotide
misc_feature            17
                        note = loop
source                  1..17
                        mol_type = other DNA
                        organism = synthetic construct
SEQUENCE: 9
tcccagcaaa caagcct                                                  17

SEQ ID NO: 10           moltype = DNA  length = 17
FEATURE                 Location/Qualifiers
misc_feature            1..17
                        note = second strand of the double stranded nucleic acid
misc_feature            1
                        note = loop
modified_base           1..6
                        mod_base = OTHER
                        note = F-ANA nucleotide
misc_feature            7..11
                        note = phosphorothioate internucleotide linkages
modified_base           13..15
                        mod_base = OTHER
                        note = F-ANA nucleotide
misc_feature            15..16
                        note = phosphorothioate internucleotide linkage
misc_feature            17
                        note = inverted T
source                  1..17
                        mol_type = other DNA
                        organism = synthetic construct
SEQUENCE: 10
aggcttgttt gctgggt                                                  17

SEQ ID NO: 11           moltype = DNA  length = 17
FEATURE                 Location/Qualifiers
misc_feature            1..17
                        note = first strand of the double stranded nucleic acid
misc_feature            1
                        note = inverted T
modified_base           2..7
                        mod_base = OTHER
                        note = 2'-OMe nucleotide
misc_feature            9..14
                        note = phosphorothioate internucleotide linkages
modified_base           15..17
                        mod_base = OTHER
                        note = 2'-OMe nucleotide
```

-continued

```
misc_feature          17
                      note = loop
source                1..17
                      mol_type = other DNA
                      organism = synthetic construct
misc_difference       17
                      note = t is u
SEQUENCE: 11
tcccagcaaa caagcct                                            17

SEQ ID NO: 12         moltype = DNA  length = 17
FEATURE               Location/Qualifiers
misc_feature          1..17
                      note = second strand of the double stranded nucleic acid
misc_feature          1
                      note = loop
modified_base         1..6
                      mod_base = OTHER
                      note = 2'-OMe nucleotide
misc_feature          7..11
                      note = phosphorothioate internucleotide linkages
modified_base         13..15
                      mod_base = OTHER
                      note = 2'-OMe nucleotide
misc_feature          15..16
                      note = phosphorothioate internucleotide linkage
misc_feature          17
                      note = inverted T
source                1..17
                      mol_type = other DNA
                      organism = synthetic construct
misc_difference       5..6
                      note = t is u
misc_difference       13
                      note = t is u
SEQUENCE: 12
aggcttgttt gctgggt                                            17

SEQ ID NO: 13         moltype = DNA  length = 16
FEATURE               Location/Qualifiers
misc_feature          1..16
                      note = first strand of the double stranded nucleic acid
modified_base         1..6
                      mod_base = OTHER
                      note = F-ANA nucleotide
misc_feature          8..13
                      note = phosphorothioate internucleotide linkages
modified_base         14..16
                      mod_base = OTHER
                      note = F-ANA nucleotide
misc_feature          16
                      note = loop
source                1..16
                      mol_type = other DNA
                      organism = synthetic construct
SEQUENCE: 13
cccagcaaac aagcct                                             16

SEQ ID NO: 14         moltype = DNA  length = 16
FEATURE               Location/Qualifiers
misc_feature          1..16
                      note = second strand of the double stranded nucleic acid
misc_feature          1
                      note = loop
modified_base         1..6
                      mod_base = OTHER
                      note = F-ANA nucleotide
misc_feature          7..11
                      note = phosphorothioate internucleotide linkages
modified_base         13..15
                      mod_base = OTHER
                      note = F-ANA nucleotide
misc_feature          15..16
                      note = phosphorothioate internucleotide linkage
source                1..16
                      mol_type = other DNA
                      organism = synthetic construct
SEQUENCE: 14
aggcttgttt gctggg                                             16
```

```
SEQ ID NO: 15           moltype = DNA  length = 16
FEATURE                 Location/Qualifiers
misc_feature            1..16
                        note = first strand of the double stranded nucleic acid
misc_feature            1..4
                        note = phosphorothioate internucleotide linkages
misc_feature            16
                        note = loop
source                  1..16
                        mol_type = other DNA
                        organism = synthetic construct
SEQUENCE: 15
cccagcaaac aagcct                                                   16

SEQ ID NO: 16           moltype = DNA  length = 16
FEATURE                 Location/Qualifiers
misc_feature            1..16
                        note = second strand of the double stranded nucleic acid
misc_feature            1
                        note = loop
misc_feature            13..16
                        note = phosphorothioate internucleotide linkages
source                  1..16
                        mol_type = other DNA
                        organism = synthetic construct
SEQUENCE: 16
aggcttgttt gctggg                                                   16

SEQ ID NO: 17           moltype = DNA  length = 16
FEATURE                 Location/Qualifiers
misc_feature            1..16
                        note = first strand of the double stranded nucleic acid
modified_base           1..6
                        mod_base = OTHER
                        note = 2' modified nucleotide
misc_feature            8..13
                        note = phosphorothioate internucleotide linkages
modified_base           14..16
                        mod_base = OTHER
                        note = 2' modified nucleotide
misc_feature            16
                        note = loop
source                  1..16
                        mol_type = other DNA
                        organism = synthetic construct
misc_difference         16
                        note = t is u
SEQUENCE: 17
cccagcaaac aagcct                                                   16

SEQ ID NO: 18           moltype = DNA  length = 16
FEATURE                 Location/Qualifiers
misc_feature            1..16
                        note = second strand of the double stranded nucleic acid
misc_feature            1
                        note = loop
modified_base           1..6
                        mod_base = OTHER
                        note = 2' modified nucleotide
misc_feature            7..11
                        note = phosphorothioate internucleotide linkages
modified_base           13..15
                        mod_base = OTHER
                        note = 2' modified nucleotide
misc_feature            15..16
                        note = phosphorothioate internucleotide linkage
source                  1..16
                        mol_type = other DNA
                        organism = synthetic construct
misc_difference         5..6
                        note = t is u
misc_difference         13
                        note = t is u
SEQUENCE: 18
aggcttgttt gctggg                                                   16

SEQ ID NO: 19           moltype = DNA  length = 16
FEATURE                 Location/Qualifiers
```

-continued

| | |
|---|---|
| source | 1..16 |
| | mol_type = other DNA |
| | organism = synthetic construct |
| misc_feature | 1..16 |
| | note = first strand of the double stranded nucleic acid |
| misc_feature | 16 |
| | note = loop |
| misc_feature | 8..13 |
| | note = phosphorothioate internucleotide linkages |
| modified_base | 1..6 |
| | mod_base = OTHER |
| | note = F-ANA nucleotide |
| modified_base | 14..16 |
| | mod_base = OTHER |
| | note = F-ANA nucleotide |
| SEQUENCE: 19 | |
| cccagcaaac aagcct | 16 |
| SEQ ID NO: 20 | moltype = DNA length = 16 |
| FEATURE | Location/Qualifiers |
| source | 1..16 |
| | mol_type = other DNA |
| | organism = synthetic construct |
| misc_feature | 1..16 |
| | note = second strand of the double stranded nucleic acid |
| misc_feature | 1 |
| | note = loop |
| modified_base | 1..6 |
| | mod_base = OTHER |
| | note = F-ANA nucleotide |
| modified_base | 13..15 |
| | mod_base = OTHER |
| | note = F-ANA nucleotide |
| misc_feature | 7..11 |
| | note = phosphorothioate internucleotide linkages |
| misc_feature | 15..16 |
| | note = phosphorothioate internucleotide linkages |
| SEQUENCE: 20 | |
| aggcttgttt gctggg | 16 |